US012247257B2

(12) United States Patent
Timsit et al.

(10) Patent No.: US 12,247,257 B2
(45) Date of Patent: Mar. 11, 2025

(54) BLOOD BIOMARKERS OF STROKE

(71) Applicants: CENTRE HOSPITALIER RÉGIONAL ET UNIVERSITAIRE DE BREST, Brest (FR); ÉTABLISSEMENT FRANÇAIS DU SANG, Saint-Denis (FR); INSERM (INSTITUT NATIONAL DE LA SANTÉ ET DE LA RECHERCHE MÉDICALE), Paris (FR); UNIVERSITÉ DE BRETAGNE OCCIDENTALE, Brest (FR)

(72) Inventors: Serge Timsit, Brest (FR); Emmanuelle Genin, Plougastel-Daoulas (FR)

(73) Assignees: CENTRE HOSPITALIER RÉGIONAL ET UNIVERSITAIRE DE BREST, Brest Cedex (FR); ÉTABLISSSEMENT FRANÇAIS DU SANG, Saint-Denis (FR); INSERM (INSTITUT NATIONAL DE LA SANTÉET DE LA RECHERCHE MÉDICALE), Paris Cedex 13 (FR); UNIVERSITÉ DE BRETAGNE OCCIDENTALE, Brest (FR)

( * ) Notice: Subject to any disclaimer, the term of this patent is extended or adjusted under 35 U.S.C. 154(b) by 908 days.

(21) Appl. No.: 17/054,820

(22) PCT Filed: May 16, 2019

(86) PCT No.: PCT/EP2019/062653
§ 371 (c)(1),
(2) Date: Nov. 12, 2020

(87) PCT Pub. No.: WO2019/219831
PCT Pub. Date: Nov. 21, 2019

(65) Prior Publication Data
US 2021/0214793 A1 Jul. 15, 2021

(30) Foreign Application Priority Data

May 16, 2018 (EP) .................................... 18305600

(51) Int. Cl.
G01N 33/53 (2006.01)
C12Q 1/6883 (2018.01)
(52) U.S. Cl.
CPC ..... *C12Q 1/6883* (2013.01); *C12Q 2600/106* (2013.01); *C12Q 2600/158* (2013.01)
(58) Field of Classification Search
None
See application file for complete search history.

(56) References Cited

U.S. PATENT DOCUMENTS

2003/0104393 A1 6/2003 Sharp et al.
2015/0274815 A1* 10/2015 Geller ................... A61P 25/00
424/152.1

FOREIGN PATENT DOCUMENTS

| WO | 2013103781 A1 | 7/2013 |
| WO | 2014120731 A1 | 8/2014 |
| WO | 2015054700 A2 | 4/2015 |
| WO | 2017011329 A1 | 1/2017 |
| WO | 2018067571 A2 | 4/2018 |

OTHER PUBLICATIONS

Torzewski et al., Animal Models of C-Reactive Protein, Hindawl Publishing Corporation, Mediators of Inflammation, vol. 2014, 2014, pp. 1-7. (Year: 2014).*
Strongin, Laboratory Diagnosis of Viral INfections, Sensitivity, Specificity, and Predictive Value of Diagnostic Tests: Definitions and Clinical Applications, Lennette, ed. Marcel Dekker, Inc. New York, pp. 211-219, 1992. (Year: 1992).*
Van Der Vekiens et al., Human and equine cardiovascular endocrinology: beware to compare, Cardiovascular Endocrinology 2013, vol. 2, No. 4, pp. 67-76. (Year: 2013).*
Kamtchum-Tatuene et al., Blood Biomarkers for stroke diagnosis and managment, Neuromolecular Med. 2019, (published online Mar. 4, 2019) 21(4), pp. 1-36 (Year: 2019).*
Adamski et al., "Expression profile based gene clusters for ischemic stroke detection", Genomics, Sep. 2014;104(3):163-9.
Astrup et al., "Cortical evoked potential and extracellular K+ and H+ at critical levels of brain ischemia", Stroke, Jan.-Feb. 1977; 8(1):51-7.
Broughton et al., "Apoptotic mechanisms after cerebral ischemia", Stroke, May 2009;40(5):e331-9.
Büttner et al., "Genomic response of the rat brain to global ischemia and reperfusion", Brain Res, Feb. 3, 2009;1252:1-14.
Chaisinanunkul et al., "Adopting a Patient-Centered Approach to Primary Outcome Analysis of Acute Stroke Trials Using a Utility-Weighted Modified Rankin Scale", Stroke, Aug. 2015;46(8):2238-43.
Chen et al., "Oxidative stress in ischemic brain damage: mechanisms of cell death and potential molecular targets for neuroprotection", Antioxid Redox Signal, Apr. 15, 2011;14(8):1505-17.
Chen et al., "Transient global ischemia triggers expression of the DNA damage-inducible gene GADD45 in the rat brain", J Cereb Blood Flow Metab, Jun. 1998; 18(6):646-57.

(Continued)

*Primary Examiner* — Gary Counts
(74) *Attorney, Agent, or Firm* — LATHROP GPM LLP; James H. Velema, Esq.; Judith L. Stone-Hulslander

(57) ABSTRACT

A method of diagnosing a stroke, a method of determining whether a subject suffering from a stroke will achieve a response with a therapy, a method of determining whether a subject is at risk of having a stroke, and a method for treating a stroke in a subject, by determining a signature in a sample obtained from the subject by measuring the expression levels of at least two biomarkers selected from the group consisting of PTGS2, HMOX1, LDLR, HSPA1B, G0S2, BAG3, TM4SF1, DUSP1 and ADM are provided.

6 Claims, 4 Drawing Sheets

Specification includes a Sequence Listing.

(56) References Cited

OTHER PUBLICATIONS

Choy et al., "The Role of the Neuroprotective Factor Npas4 in Cerebral Ischemia", Int J Mol Sci, Dec. 4, 2015;16(12):29011-28.
Cook & Tymianski, "Nonhuman primate models of stroke for translational neuroprotection research", Neurotherapeutics, Apr. 2012;9(2):371-9.
Cook et al., "Treatment of stroke with a PSD-95 inhibitor in the gyrencephalic primate brain", Nature, Feb. 29, 2012;483(7388):213-7.
Cox-Limpens et al., "Endogenous brain protection: what the cerebral transcriptome teaches us", Brain Res, May 20, 2014;1564:85-100.
Dai & Grant, "Cyclin-dependent kinase inhibitors", Curr Opin Pharmacol, Aug. 2003;3(4):362-70.
Demyanenko et al., "Profiling of Signaling Proteins in Penumbra After Focal Photothrombotic Infarct in the Rat Brain Cortex", Mol Neurobiol, Nov. 2017;54(9):6839-6856.
Donnan et al., "Penumbral selection of patients for trials of acute stroke therapy", Lancet Neurol, Mar. 2009;8(3):261-9.
Easton et al., "Definition and evaluation of transient ischemic attack: a scientific statement for healthcare professionals from the American Heart Association/American Stroke Association Stroke Council; Council on Cardiovascular Surgery and Anesthesia; Council on Cardiovascular Radiology and Intervention; Council on Cardiovascular Nursing; and the Interdisciplinary Council on Peripheral Vascular Disease. The American Academy of Neurology affirms the value of this statement as an educational tool for neurologists", Stroke, Jun. 2009;40(6):2276-93.
Eikelboom et al., "Aspirin-resistant thromboxane biosynthesis and the risk of myocardial infarction, stroke, or cardiovascular death in patients at high risk for cardiovascular events", Circulation, Apr. 9, 2002; 105(14):1650-5.
Emberson et al., "Effect of treatment delay, age, and stroke severity on the effects of intravenous thrombolysis with alteplase for acute ischaemic stroke: a meta-analysis of individual patient data from randomised trials", Lancet, Nov. 29, 2014;384(9958):1929-35.
Filgueira de Azevedo et al., "Molecular model of cyclin-dependent kinase 5 complexed with roscovitine", Biochem Biophys Res Commun, Oct. 11, 2002;297(5):1154-8.
Fisher et al., "Update of the stroke therapy academic industry roundtable preclinical recommendations", Stroke, Jun. 2009;40(6):2244-50.
Gauberti et al., "Thrombotic stroke in the anesthetized monkey (*Macaca mulatta*): characterization by MRI—a pilot study", Cerebrovasc Dis, 2012;33(4):329-39.
Gutiérrez-Vargas et al., "Targeting CDK5 post-stroke provides long-term neuroprotection and rescues synaptic plasticity", J Cereb Blood Flow Metab, Jun. 2017;37(6):2208-2223.
Hillis & Baron, "Editorial: the ischemic penumbra: still the target for stroke therapies?", Front Neurol, Apr. 22, 2015;6:85.
Hori et al., "Unraveling the ischemic brain transcriptome in a permanent middle cerebral artery occlusion mouse model by DNA microarray analysis", Dis Model Mech, Mar. 2012;5(2):270-83.
Jovin et al., "Diffusion-weighted imaging or computerized tomography perfusion assessment with clinical mismatch in the triage of wake up and late presenting strokes undergoing neurointervention with Trevo (DAWN) trial methods", Int J Stroke, Aug. 2017;12(6):641-652.
Kawahara et al., "Genome-wide gene expression analysis for induced ischemic tolerance and delayed neuronal death following transient global ischemia in rats", J Cereb Blood Flow Metab, Feb. 2004;24(2):212-23.
Khaitovich et al., "Regional patterns of gene expression in human and chimpanzee brains", Genome Res, Aug. 2004;14(8):1462-73.
Kim et al., "Biomarkers for stroke", J Stroke, Jan. 2013;15(1):27-37.
Kim et al., "Deletion of the inducible 70-kDa heat shock protein genes in mice impairs cardiac contractile function and calcium handling associated with hypertrophy", Circulation, Jun. 6, 2006;113(22):2589-97.
Knockaert et al., "Pharmacological inhibitors of cyclin-dependent kinases", Trends Pharmacol Sci, Sep. 2002; 23 (9):417-25.
Kurisu & Yenari, "Therapeutic hypothermia for ischemic stroke; pathophysiology and future promise", Neuropharmacology, May 15, 2018;134(Pt B):302-309.
Lee et al., "Effects of hsp70.1 gene knockout on the mitochondrial apoptotic pathway after focal cerebral ischemia", Stroke, Sep. 2004;35(9):2195-9.
Lipton, "Ischemic cell death in brain neurons", Physiol Rev, Oct. 1999;79(4):1431-568.
Liu et al., "Correlation of adrenomedullin gene expression in peripheral blood leukocytes with severity of ischemic stroke", Int J Neurosci, Apr. 2014;124(4):271-80.
Llovera et al., "Results of a preclinical randomized controlled multicenter trial (pRCT): Anti-CD49d treatment for acute brain ischemia", Sci Transl Med, Aug. 5, 2015;7(299):299ra121.
Lu et al., "Microarray analysis of acute and delayed gene expression profile in rats after focal ischemic brain injury and reperfusion", J Neurosci Res, Sep. 15, 2004;77(6):843-5.
Mick et al., "Stroke and Circulating Extracellular RNAs", Stroke, Apr. 2017;48(4):828-834.
Moore et al. "Using peripheral blood mononuclear cells to determine a gene expression profile of acute ischemic stroke: a pilot investigation", Circulation, Jan. 18, 2005;111(2):212-21.
Moretti et al., "Neuroprotection for ischaemic stroke: current status and challenges", Pharmacol Ther, Feb. 2015;146:23-34.
Nadarajan et al., "Transient ischaemic attacks: mimics and chameleons", Pract Neurol, Feb. 2014;14(1):23-31.
Nogueira et al., "Thrombectomy 6 to 24 Hours after Stroke with a Mismatch between Deficit and Infarct", N Engl J Med, Jan. 4, 2018;378(1):11-21.
O'Hare et al., "Cyclin-dependent kinases as potential targets to improve stroke outcome", Pharmacol Ther, Feb.-Mar. 2002;93(2-3):135-43.
Ramamoorthi et al., "Npas4 regulates a transcriptional program in CA3 required for contextual memory formation", Science, Dec. 23, 2011;334(6063):1669-75.
Rothstein & Jickling, "Ischemic stroke biomarkers in blood", Biomark Med, Feb. 2013;7(1):37-47.
Sacco et al., "An updated definition of stroke for the 21st century: a statement for healthcare professionals from the American Heart Association/American Stroke Association", Stroke, Jul. 2013;44(7):2064-89.
Schmidt-Kastner et al., "DNA microarray analysis of cortical gene expression during early recirculation after focal brain ischemia in rat", Brain Res Mol Brain Res, Dec. 2002;108(1-2):81-93.
Sedaghat & Notopoulos, "S100 protein family and its application in clinical practice", Hippokratia, 2008;12(4):198-204.
Stamova et al., "Gene expression profiling of blood for the prediction of ischemic stroke", Stroke, Oct. 2010;41(10):2171-7.
Street et al., "Single nucleotide polymorphisms (SNPs) are highly conserved in rhesus (*Macaca mulatta*) and cynomolgus (*Macaca fascicularis*) macaques", BMC Genomics, Dec. 31, 2007;8:480.
Stroke Therapy Academic Industry Roundtable (STAIR), "Recommendations for standards regarding preclinical neuroprotective and restorative drug development", Stroke, Dec. 1999;30(12):2752-8.
Takano et al., "Induction of CL100 protein tyrosine phosphatase following transient forebrain ischemia in the rat brain", J Cereb Blood Flow Metab, Jan. 1995;15(1):33-41.
Tang et al., "Gene expression in blood changes rapidly in neutrophils and monocytes after ischemic stroke in humans: a microarray study", J Cereb Blood Flow Metab, Aug. 2006;26(8):1089-102.
Tang et al., "Genomic responses of the brain to ischemic stroke, intracerebral haemorrhage, kainate seizures, hypoglycemia, and hypoxia", Eur J Neurosci, Jun. 2002;15(12):1937-52.
Timsit & Menn, "Cyclin-dependent kinase inhibition with roscovitine: neuroprotection in acute ischemic stroke", Clin Pharmacol Ther, Feb. 2012;91(2):327-32.

(56) References Cited

OTHER PUBLICATIONS

Tohgi et al., "Effects of low-to-high doses of aspirin on platelet aggregability and metabolites of thromboxane A2 and prostacyclin", Stroke, Oct. 1992;23(10):1400-3.
Ueda et al., "Dual-specificity phosphatase 5 (DUSP5) as a direct transcriptional target of tumor suppressor p532003", Oncogene, Aug. 28, 2003;22(36):5586-91.
Vanacker et al., "Eligibility and Predictors for Acute Revascularization Procedures in a Stroke Center", Stroke, Jul. 2016;47(7):1844-9.
Wang et al., "Dynamic variation of genes profiles and pathways in the hippocampus of ischemic mice: a genomic study", Brain Res, Feb. 4, 2011;1372:13-21.
Wang et al., "Increased inflammation and brain injury after transient focal cerebral ischemia in activating transcription factor 3 knockout mice", Neuroscience, Sep. 18, 2012;220:100-8.
Zhang et al., "Neuronal activation of NF-kappaB contributes to cell death in cerebral ischemia", J Cereb Blood Flow Metab, Jan. 2005;25(1):30-40.
Zhao et al., "Biomarkers in Pharmaceutical Research", Clin Chem, Nov. 2015;61(11):1343-53.
Zhao et al., "Global Transcriptomic Profiling of Cortex and Striatum: Cerebral Injury after Ischemia/Reperfusion in a Mouse Model", J Stroke Cerebrovasc Dis, Jul. 2017;26(7):1622-1634.
Zheng et al., "Anti-inflammatory effects of the 70 kDa heat shock protein in experimental stroke", J Cereb Blood Flow Metab, Jan. 2008;28(1):53-63.
European Search Report (ESR) of EP18305600.1.
International Search Report (ISR) of PCT/EP2019/062653, 2020.
Adamski et al. "Expression profile based gene clusters for ischemic stroke detection", Genomics, 2014, vol. 104, pp. 163-169.

* cited by examiner

*GADD45G*

*CDKN1A*

SEQUENCE LISTING

<160> NUMBER OF SEQ ID NOS: 18

<210> SEQ ID NO 1
<211> LENGTH: 604
<212> TYPE: PRT
<213> ORGANISM: Homo sapiens
<220> FEATURE:
<221> NAME/KEY: MISC_FEATURE
<223> OTHER INFORMATION: PTGS2 Accession number NP_000954.1

<400> SEQUENCE: 1

Met Leu Ala Arg Ala Leu Leu Leu Cys Ala Val Leu Ala Leu Ser His
1               5                   10                  15

Thr Ala Asn Pro Cys Cys Ser His Pro Cys Gln Asn Arg Gly Val Cys
            20                  25                  30

Met Ser Val Gly Phe Asp Gln Tyr Lys Cys Asp Cys Thr Arg Thr Gly
        35                  40                  45

Phe Tyr Gly Glu Asn Cys Ser Thr Pro Glu Phe Leu Thr Arg Ile Lys
    50                  55                  60

Leu Phe Leu Lys Pro Thr Pro Asn Thr Val His Tyr Ile Leu Thr His
65                  70                  75                  80

Phe Lys Gly Phe Trp Asn Val Val Asn Asn Ile Pro Phe Leu Arg Asn
                85                  90                  95

Ala Ile Met Ser Tyr Val Leu Thr Ser Arg Ser His Leu Ile Asp Ser
            100                 105                 110

Pro Pro Thr Tyr Asn Ala Asp Tyr Gly Tyr Lys Ser Trp Glu Ala Phe
        115                 120                 125

Ser Asn Leu Ser Tyr Tyr Thr Arg Ala Leu Pro Pro Val Pro Asp Asp
    130                 135                 140

Cys Pro Thr Pro Leu Gly Val Lys Gly Lys Lys Gln Leu Pro Asp Ser
145                 150                 155                 160

Asn Glu Ile Val Glu Lys Leu Leu Leu Arg Arg Lys Phe Ile Pro Asp
                165                 170                 175

Pro Gln Gly Ser Asn Met Met Phe Ala Phe Phe Ala Gln His Phe Thr
            180                 185                 190

His Gln Phe Phe Lys Thr Asp His Lys Arg Gly Pro Ala Phe Thr Asn
        195                 200                 205

Gly Leu Gly His Gly Val Asp Leu Asn His Ile Tyr Gly Glu Thr Leu
    210                 215                 220

Ala Arg Gln Arg Lys Leu Arg Leu Phe Lys Asp Gly Lys Met Lys Tyr
225                 230                 235                 240

Gln Ile Ile Asp Gly Glu Met Tyr Pro Pro Thr Val Lys Asp Thr Gln
                245                 250                 255

Ala Glu Met Ile Tyr Pro Pro Gln Val Pro Glu His Leu Arg Phe Ala

|  |  |  |  |  |  |  |  |  |  |
|---|---|---|---|---|---|---|---|---|---|
|  |  | 260 |  |  | 265 |  |  | 270 |  |
| Val | Gly | Gln | Glu | Val | Phe | Gly | Leu | Val | Pro | Gly | Leu | Met | Met | Tyr | Ala |
|  |  | 275 |  |  |  | 280 |  |  | 285 |

Val Gly Gln Glu Val Phe Gly Leu Val Pro Gly Leu Met Met Tyr Ala
              275                 280                 285
Thr Ile Trp Leu Arg Glu His Asn Arg Val Cys Asp Val Leu Lys Gln
              290                 295                 300
Glu His Pro Glu Trp Gly Asp Glu Gln Leu Phe Gln Thr Ser Arg Leu
305                 310                 315                 320
Ile Leu Ile Gly Glu Thr Ile Lys Ile Val Ile Glu Asp Tyr Val Gln
              325                 330                 335
His Leu Ser Gly Tyr His Phe Lys Leu Lys Phe Asp Pro Glu Leu Leu
              340                 345                 350
Phe Asn Lys Gln Phe Gln Tyr Gln Asn Arg Ile Ala Ala Glu Phe Asn
              355                 360                 365
Thr Leu Tyr His Trp His Pro Leu Leu Pro Asp Thr Phe Gln Ile His
              370                 375                 380
Asp Gln Lys Tyr Asn Tyr Gln Gln Phe Ile Tyr Asn Asn Ser Ile Leu
385                 390                 395                 400
Leu Glu His Gly Ile Thr Gln Phe Val Glu Ser Phe Thr Arg Gln Ile
              405                 410                 415
Ala Gly Arg Val Ala Gly Gly Arg Asn Val Pro Ala Val Gln Lys
              420                 425                 430
Val Ser Gln Ala Ser Ile Asp Gln Ser Arg Gln Met Lys Tyr Gln Ser
              435                 440                 445
Phe Asn Glu Tyr Arg Lys Arg Phe Met Leu Lys Pro Tyr Glu Ser Phe
450                 455                 460
Glu Glu Leu Thr Gly Glu Lys Glu Met Ser Ala Glu Leu Glu Ala Leu
465                 470                 475                 480
Tyr Gly Asp Ile Asp Ala Val Glu Leu Tyr Pro Ala Leu Leu Val Glu
              485                 490                 495
Lys Pro Arg Pro Asp Ala Ile Phe Gly Glu Thr Met Val Glu Val Gly
              500                 505                 510
Ala Pro Phe Ser Leu Lys Gly Leu Met Gly Asn Val Ile Cys Ser Pro
              515                 520                 525
Ala Tyr Trp Lys Pro Ser Thr Phe Gly Gly Glu Val Gly Phe Gln Ile
              530                 535                 540
Ile Asn Thr Ala Ser Ile Gln Ser Leu Ile Cys Asn Asn Val Lys Gly
545                 550                 555                 560
Cys Pro Phe Thr Ser Phe Ser Val Pro Asp Pro Glu Leu Ile Lys Thr
              565                 570                 575
Val Thr Ile Asn Ala Ser Ser Ser Arg Ser Gly Leu Asp Asp Ile Asn
              580                 585                 590
Pro Thr Val Leu Leu Lys Glu Arg Ser Thr Glu Leu
              595                 600

<210> SEQ ID NO 2
<211> LENGTH: 4510
<212> TYPE: DNA
<213> ORGANISM: Homo sapiens
<220> FEATURE:
<221> NAME/KEY: misc_feature
<223> OTHER INFORMATION: PTGS2 Accession number NM_000963.4

<400> SEQUENCE: 2
aattgtcata cgacttgcag tgagcgtcag gagcacgtcc aggaactcct cagcagcgcc      60
tccttcagct ccacagccag acgccctcag acagcaaagc ctaccccgc gccgcgccct     120

```
gcccgccgct gcgatgctcg cccgcgccct gctgctgtgc gcggtcctgg cgctcagcca      180
tacagcaaat ccttgctgtt cccacccatg tcaaaaccga ggtgtatgta tgagtgtggg      240
atttgaccag tataagtgcg attgtacccg gacaggattc tatggagaaa actgctcaac      300
accggaattt ttgacaagaa taaaattatt tctgaaaccc actccaaaca cagtgcacta      360
catacttacc cacttcaagg gattttggaa cgttgtgaat aacattccct tccttcgaaa      420
tgcaattatg agttatgtgt tgacatccag atcacatttg attgacagtc caccaactta      480
caatgctgac tatggctaca aaagctggga agccttctct aacctctcct attatactag      540
agcccttcct cctgtgcctg atgattgccc gactcccttg ggtgtcaaag gtaaaaagca      600
gcttcctgat tcaaatgaga ttgtggaaaa attgcttcta agaagaaagt tcatccctga      660
tccccagggc tcaaacatga tgtttgcatt ctttgcccag cacttcacgc atcagttttt      720
caagacagat cataagcgag ggccagcttt caccaacggg ctgggccatg gggtggactt      780
aaatcatatt tacggtgaaa ctctggctag acagcgtaaa ctgcgccttt caaggatgg      840 aaaaatgaaa tatcagataa ttgatggaga gatgtatcct cccacagtca aagatactca      900
ggcagagatg atctaccctc tcaagtccc tgagcatcta cggtttgctg tggggcagga      960
ggtctttggt ctggtgcctg gtctgatgat gtatgccaca atctggctgc gggaacacaa     1020
cagagtatgc gatgtgctta acaggagca tcctgaatgg ggtgatgagc agttgttcca     1080
gacaagcagg ctaatactga taggagagac tattaagatt gtgattgaag attatgtgca     1140
acacttgagt ggctatcact tcaaactgaa atttgaccca gaactacttt tcaacaaaca     1200
attccagtac caaaatcgta ttgctgctga atttaacacc ctctatcact ggcatcccct     1260
tctgcctgac acctttcaaa ttcatgacca gaaatacaac tatcaacagt ttatctacaa     1320
caactctata ttgctggaac atggaattac ccagtttgtt gaatcattca ccaggcaaat     1380
tgctggcagg gttgctggtg gtaggaatgt tccacccgca gtacagaaag tatcacaggc     1440
ttccattgac cagagcaggc agatgaaata ccagtctttt aatgagtacc gcaaacgctt     1500
tatgctgaag ccctatgaat catttgaaga acttacagga gaaaggaaa tgtctgcaga     1560 gttggaagca ctctatggtg acatcgatgc tgtggagctg tatcctgccc ttctggtaga     1620
aaagcctcgg ccagatgcca tctttggtga accatggta gaagttggag caccattctc     1680
cttgaaagga cttatgggta atgttatatg ttctcctgcc tactgaaagc caagcacttt     1740
tggtggagaa gtgggtttc aaatcatcaa cactgcctca attcagtctc tcatctgcaa     1800
taacgtgaag ggctgtccct ttacttcatt cagtgttcca gatccagagc tcattaaaac     1860
agtcaccatc aatgcaagtt cttcccgctc cggactagat gatatcaatc ccacagtact     1920
actaaaagaa cgttcgactg aactgtagaa gtctaatgat catatttatt tatttatatg     1980
aaccatgtct attaatttaa ttatttaata atatttatat taaactcctt atgttactta     2040
acatcttctg taacagaagt cagtactcct gttgcggaga aaggagtcat acttgtgaag     2100
acttttatgt cactactcta aagattttgc tgttgctgtt aagtttggaa acagttttt     2160 attctgtttt ataaaccaga gagaaatgag ttttgacgtc tttttacttg aatttcaact     2220
tatattataa gaacgaaagt aaagatgttt gaatacttaa acactgtcac aagatggcaa     2280
aatgctgaaa gttttacac tgtcgatgtt tccaatgcat cttccatgat gcattagaag     2340
taactaatgt ttgaaatttt aaagtacttt tggttatttt tctgtcatca aacaaaaaca     2400
ggtatcagtg cattattaaa tgaatattta aattagacat taccagtaat ttcatgtcta     2460
```

-continued

| | |
|---|---|
| cttttttaaaa tcagcaatga acaataatt tgaaatttct aaattcatag ggtagaatca | 2520 |
| cctgtaaaag cttgtttgat ttcttaaagt tattaaactt gtacatatac caaaaagaag | 2580 |
| ctgtcttgga tttaaatctg taaaatcagt agaaatttta ctacaattgc ttgttaaaat | 2640 |
| attttataag tgatgttcct ttttcaccaa gagtataaac cttttagtg tgactgttaa | 2700 |
| aacttccttt taaatcaaaa tgccaaattt attaaggtgg tggagccact gcagtgttat | 2760 |
| cttaaaataa gaatattttg ttgagatatt ccagaatttg tttatatggc tggtaacatg | 2820 |
| taaaatctat atcagcaaaa gggtctacct ttaaaataag caataacaaa gaagaaaacc | 2880 |
| aaattattgt tcaaatttag gtttaaactt tgaagcaaa ctttttttta tccttgtgca | 2940 |
| ctgcaggcct ggtactcaga ttttgctatg aggttaatga agtaccaagc tgtgcttgaa | 3000 |
| taatgatatg ttttctcaga tttttctgttg tacagtttaa tttagcagtc catatcacat | 3060 |
| tgcaaaagta gcaatgacct cataaaatac ctcttcaaaa tgcttaaatt catttcacac | 3120 |
| attaatttta tctcagtctt gaagccaatt cagtaggtgc attggaatca agcctggcta | 3180 |
| cctgcatgct gttccttttc ttttcttctt ttagccattt tgctaagaga cacagtcttc | 3240 |
| tcatcacttc gtttctccta ttttgttttta ctagttttaa gatcagagtt cactttcttt | 3300 |
| ggactctgcc tatattttct tacctgaact tttgcaagtt ttcaggtaaa cctcagctca | 3360 |
| ggactgctat ttagctcctc ttaagaagat taaagagaa aaaaaaaggc cctttttaaaa | 3420 |
| atagtataca cttattttaa gtgaaaagca gagaatttta tttatagcta attttagcta | 3480 |
| tctgtaacca agatggatgc aaagaggcta gtgcctcaga gagaactgta cggggtttgt | 3540 |
| gactggaaaa agttacgttc ccattctaat taatgccctt tcttatttaa aaacaaaacc | 3600 |
| aaatgatatc taagtagttc tcagcaataa taataatgac gataatactt cttttccaca | 3660 |
| tctcattgtc actgacattt aatggtactg tatattactt aatttattga agattattat | 3720 |
| ttatgtctta ttaggacact atggttataa actgtgttta agcctacaat cattgatttt | 3780 |
| tttttgttat gtcacaatca gtatatttttc tttggggtta cctctctgaa tattatgtaa | 3840 |
| acaatccaaa gaatgattg tattaagatt tgtgaataaa ttttagaaa tctgattggc | 3900 |
| atattgagat atttaaggtt gaatgttttgt ccttaggata ggcctatgtg ctagcccaca | 3960 |
| aagaatattg tctcattagc ctgaatgtgc cataagactg acctttaaaa atgttttgag | 4020 |
| ggatctgtgg atgcttcgtt aatttgttca gccacaattt attgagaaaa tattctgtgt | 4080 |
| caagcactgt gggttttaat atttttaaat caaacgctga ttacagataa tagtatttat | 4140 |
| ataaataatt gaaaaaaatt ttcttttggg aagagggaga aaatgaaata aatatcatta | 4200 |
| aagataactc aggagaatct tctttacaat tttacgttta gaatgtttaa ggttaagaaa | 4260 |
| gaaatagtca atatgcttgt ataaaacact gttcactgtt tttttttaaaa aaaaaacttg | 4320 |
| atttgttatt aacattgatc tgctgacaaa acctgggaat ttgggttgtg tatgcgaatg | 4380 |
| tttcagtgcc tcagacaaat gtgtatttaa cttatgtaaa agataagtct ggaaataaat | 4440 |
| gtctgtttat ttttgtacta tttaaaaatt gacagatctt ttctgaagat aaactttgat | 4500 |
| tgtttctata | 4510 |

<210> SEQ ID NO 3
<211> LENGTH: 288
<212> TYPE: PRT
<213> ORGANISM: Homo sapiens
<220> FEATURE:
<221> NAME/KEY: MISC_FEATURE
<223> OTHER INFORMATION: HMOX1 Accession number NP_002124.1

<400> SEQUENCE: 3

Met Glu Arg Pro Gln Pro Asp Ser Met Pro Gln Asp Leu Ser Glu Ala
1               5                   10                  15

Leu Lys Glu Ala Thr Lys Glu Val His Thr Gln Ala Glu Asn Ala Glu
            20                  25                  30

Phe Met Arg Asn Phe Gln Lys Gly Gln Val Thr Arg Asp Gly Phe Lys
        35                  40                  45

Leu Val Met Ala Ser Leu Tyr His Ile Tyr Val Ala Leu Glu Glu Glu
    50                  55                  60

Ile Glu Arg Asn Lys Glu Ser Pro Val Phe Ala Pro Val Tyr Phe Pro
65                  70                  75                  80

Glu Glu Leu His Arg Lys Ala Ala Leu Glu Gln Asp Leu Ala Phe Trp
                85                  90                  95

Tyr Gly Pro Arg Trp Gln Glu Val Ile Pro Tyr Thr Pro Ala Met Gln
            100                 105                 110

Arg Tyr Val Lys Arg Leu His Glu Val Gly Arg Thr Glu Pro Glu Leu
        115                 120                 125

Leu Val Ala His Ala Tyr Thr Arg Tyr Leu Gly Asp Leu Ser Gly Gly
    130                 135                 140

Gln Val Leu Lys Lys Ile Ala Gln Lys Ala Leu Asp Leu Pro Ser Ser
145                 150                 155                 160

Gly Glu Gly Leu Ala Phe Phe Thr Phe Pro Asn Ile Ala Ser Ala Thr
                165                 170                 175

Lys Phe Lys Gln Leu Tyr Arg Ser Arg Met Asn Ser Leu Glu Met Thr
            180                 185                 190

Pro Ala Val Arg Gln Arg Val Ile Glu Glu Ala Lys Thr Ala Phe Leu
        195                 200                 205

Leu Asn Ile Gln Leu Phe Glu Glu Leu Gln Glu Leu Leu Thr His Asp
    210                 215                 220

Thr Lys Asp Gln Ser Pro Ser Arg Ala Pro Gly Leu Arg Gln Arg Ala
225                 230                 235                 240

Ser Asn Lys Val Gln Asp Ser Ala Pro Val Glu Thr Pro Arg Gly Lys
                245                 250                 255

Pro Pro Leu Asn Thr Arg Ser Gln Ala Pro Leu Leu Arg Trp Val Leu
            260                 265                 270

Thr Leu Ser Phe Leu Val Ala Thr Val Ala Val Gly Leu Tyr Ala Met
    275                 280                 285

<210> SEQ ID NO 4
<211> LENGTH: 1554
<212> TYPE: DNA
<213> ORGANISM: Homo sapiens
<220> FEATURE:
<221> NAME/KEY: misc_feature
<223> OTHER INFORMATION: HMOX1 Accession number NM_002133.3

<400> SEQUENCE: 4
aacgcctgcc tcctctcgag cgtcctcagc gcagccgccg cccgcggagc cagcacgaac      60
gagcccagca ccggccggat ggagcgtccg caacccgaca gcatgcccca ggatttgtca     120
gaggccctga aggaggccac caaggaggtg cacacccagg cagagaatgc tgagttcatg     180
aggaactttc agaagggcca ggtgacccga gacggcttca gctggtgat ggcctccctg      240 taccacatct atgtggccct ggaggaggag attgagcgca acaaggagag cccagtcttc     300
gcccctgtct acttcccaga gagctgcac cgcaaggctg ccctggagca ggacctggcc     360

-continued

```
ttctggtacg ggccccgctg gcaggaggtc atcccctaca caccagccat gcagcgctat      420
gtgaagcggc tccacgaggt ggggcgcaca gagcccgagc tgctggtggc ccacgcctac      480
acccgctacc tgggtgacct gtctgggggc caggtgctca aaaagattgc ccagaaagcc      540
ctggacctgc ccagctctgg cgagggcctg gccttcttca ccttcccaa cattgccagt       600
gccaccaagt tcaagcagct ctaccgctcc cgcatgaact ccctggagat gactcccgca      660
gtcaggcaga gggtgataga agaggccaag actgcgttcc tgctcaacat ccagctcttt     720
gaggagttgc aggagctgct gacccatgac accaaggacc agagcccctc acgggcacca      780
gggcttcgcc agcgggccag caacaaagtg caagattctg ccccgtgga gactcccaga      840
gggaagcccc cactcaacac ccgctcccag gctccgcttc tccgatgggt ccttacactc      900
agctttctgg tggcgacagt tgctgtaggg ctttatgcca tgtgaatgca ggcatgctgg      960
ctcccagggc catgaacttt gtccggtgga aggccttctt tctagagagg gaattctctt      1020
ggctggcttc cttaccgtgg gcactgaagg cttttcaggg c ctccagcct ctcactgtgt    1080
ccctctctct ggaaaggagg aaggagccta tggcatcttc cccaacgaaa agcacatcca      1140
ggcaatggcc taaacttcag aggggggcgaa gggatcagcc ctgcccttca gcatcctcag    1200
ttcctgcagc agagcctgga agacacccta atgtggcagc tgtctcaaac ctccaaaagc      1260
cctgagtttc aagtatcctt gttgacacgg ccatgaccac tttccccgtg gccatggca     1320
atttttacac aaacctgaaa agatgttgtg tcttgtgttt ttgtcttatt tttgttggag     1380
ccactctgtt cctggctcag cctcaaatgc agtatttttg ttgtgttctg ttgttttttat  1440
agcagggttg gggtggtttt tgagccatgc gtgggtgggg agggaggtgt ttaacggcac     1500
tgtggccttg gtctaacttt tgtgtgaaat aataaacaac attgtctgat agta           1554
```

<210> SEQ ID NO 5
<211> LENGTH: 860
<212> TYPE: PRT
<213> ORGANISM: Homo sapiens
<220> FEATURE:
<221> NAME/KEY: MISC_FEATURE
<223> OTHER INFORMATION: LDLR Accession number NP_000518.1

<400> SEQUENCE: 5

```
Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
                20                  25                  30

Gln Cys Gln Asp Gly Lys Cys Ile Ser Tyr Lys Trp Val Cys Asp Gly
            35                  40                  45

Ser Ala Glu Cys Gln Asp Gly Ser Asp Glu Ser Gln Glu Thr Cys Leu
        50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
```

-continued

```
            145                 150                 155                 160
        Ile Pro Gln Leu Trp Ala Cys Asp Asn Asp Pro Asp Cys Glu Asp Gly
                        165                 170                 175

Ser Asp Glu Trp Pro Gln Arg Cys Arg Gly Leu Tyr Val Phe Gln Gly
                        180                 185                 190

Asp Ser Ser Pro Cys Ser Ala Phe Glu Phe His Cys Leu Ser Gly Glu
                        195                 200                 205

Cys Ile His Ser Ser Trp Arg Cys Asp Gly Pro Asp Cys Lys Asp
                        210                 215                 220

Lys Ser Asp Glu Glu Asn Cys Ala Val Ala Thr Cys Arg Pro Asp Glu
        225                 230                 235                 240

Phe Gln Cys Ser Asp Gly Asn Cys Ile His Gly Ser Arg Gln Cys Asp
                        245                 250                 255

Arg Glu Tyr Asp Cys Lys Asp Met Ser Asp Glu Val Gly Cys Val Asn
                        260                 265                 270

Val Thr Leu Cys Glu Gly Pro Asn Lys Phe Lys Cys His Ser Gly Glu
                        275                 280                 285

Cys Ile Thr Leu Asp Lys Val Cys Asn Met Ala Arg Asp Cys Arg Asp
                        290                 295                 300

Trp Ser Asp Glu Pro Ile Lys Glu Cys Gly Thr Asn Glu Cys Leu Asp
        305                 310                 315                 320

Asn Asn Gly Gly Cys Ser His Val Cys Asn Asp Leu Lys Ile Gly Tyr
                        325                 330                 335

Glu Cys Leu Cys Pro Asp Gly Phe Gln Leu Val Ala Gln Arg Arg Cys
                        340                 345                 350

Glu Asp Ile Asp Glu Cys Gln Asp Pro Asp Thr Cys Ser Gln Leu Cys
                        355                 360                 365

Val Asn Leu Glu Gly Gly Tyr Lys Cys Gln Cys Glu Glu Gly Phe Gln
                        370                 375                 380

Leu Asp Pro His Thr Lys Ala Cys Lys Ala Val Gly Ser Ile Ala Tyr
        385                 390                 395                 400

Leu Phe Phe Thr Asn Arg His Glu Val Arg Lys Met Thr Leu Asp Arg
                        405                 410                 415

Ser Glu Tyr Thr Ser Leu Ile Pro Asn Leu Arg Asn Val Val Ala Leu
                        420                 425                 430

Asp Thr Glu Val Ala Ser Asn Arg Ile Tyr Trp Ser Asp Leu Ser Gln
                        435                 440                 445

Arg Met Ile Cys Ser Thr Gln Leu Asp Arg Ala His Gly Val Ser Ser
        450                 455                 460

Tyr Asp Thr Val Ile Ser Arg Asp Ile Gln Ala Pro Asp Gly Leu Ala
        465                 470                 475                 480

Val Asp Trp Ile His Ser Asn Ile Tyr Trp Thr Asp Ser Val Leu Gly
                        485                 490                 495

Thr Val Ser Val Ala Asp Thr Lys Gly Val Lys Arg Lys Thr Leu Phe
                        500                 505                 510

Arg Glu Asn Gly Ser Lys Pro Arg Ala Ile Val Val Asp Pro Val His
                        515                 520                 525

Gly Phe Met Tyr Trp Thr Asp Trp Gly Thr Pro Ala Lys Ile Lys Lys
                        530                 535                 540

Gly Gly Leu Asn Gly Val Asp Ile Tyr Ser Leu Val Thr Glu Asn Ile
        545                 550                 555                 560

Gln Trp Pro Asn Gly Ile Thr Leu Asp Leu Leu Ser Gly Arg Leu Tyr
                        565                 570                 575
```

```
Trp Val Asp Ser Lys Leu His Ser Ile Ser Ile Asp Val Asn Gly
        580                 585                 590

Gly Asn Arg Lys Thr Ile Leu Glu Asp Glu Lys Arg Leu Ala His Pro
    595                 600                 605

Phe Ser Leu Ala Val Phe Glu Asp Lys Val Phe Trp Thr Asp Ile Ile
610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670

Ser Asn Gly Gly Cys Gln Tyr Leu Cys Leu Pro Ala Pro Gln Ile Asn
        675                 680                 685

Pro His Ser Pro Lys Phe Thr Cys Ala Cys Pro Asp Gly Met Leu Leu
    690                 695                 700

Ala Arg Asp Met Arg Ser Cys Leu Thr Glu Ala Glu Ala Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
            740                 745                 750

Pro Gly Ala Thr Pro Gly Leu Thr Thr Val Glu Ile Val Thr Met Ser
        755                 760                 765

His Gln Ala Leu Gly Asp Val Ala Gly Arg Gly Asn Glu Lys Lys Pro
    770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Lys Thr Thr
            820                 825                 830

Glu Asp Glu Val His Ile Cys His Asn Gln Asp Gly Tyr Ser Tyr Pro
        835                 840                 845

Ser Arg Gln Met Val Ser Leu Glu Asp Asp Val Ala
    850                 855                 860

<210> SEQ ID NO 6
<211> LENGTH: 5292
<212> TYPE: DNA
<213> ORGANISM: Homo sapiens
<220> FEATURE:
<221> NAME/KEY: misc_feature
<223> OTHER INFORMATION: LDLR Accession number NM_000527.4

<400> SEQUENCE: 6
ctcttgcagt gaggtgaaga catttgaaaa tcaccccact gcaaactcct cccctgcta      60 gaaacctcac attgaaatgc tgtaaatgac gtgggccccg agtgcaatcg cggaagcca    120 gggtttccag ctaggacaca gcaggtcgtg atccgggtcg gacactgcc tggcagaggc    180 tgcgagcatg gggccctggg gctggaaatt gcgctggacc gtcgccttgc tcctcgccgc   240
ggcggggact gcagtgggcg acagatgcga agaaacgag ttccagtgcc aagacgggaa   300
atgcatctcc tacaagtggg tctgcgatgg cagcgctgag tgccaggatg gctctgatga   360
gtcccaggag acgtgcttgt ctgtcacctg caaatccggg gacttcagct gtggggccg   420
```

```
tgtcaaccgc tgcattcctc agttctggag gtgcgatggc caagtggact gcgacaacgg    480
ctcagacgag caaggctgtc cccccaagac gtgctcccag gacgagtttc gctgccacga    540
tgggaagtgc atctctcggc agttcgtctg tgactcagac cgggactgct tggacggctc    600
agacgaggcc tcctgcccgg tgctcacctg tggtcccgcc agcttccagt gcaacagctc    660
cacctgcatc ccccagctgt gggcctgcga caacgacccc gactgcgaag atggctcgga    720
tgagtggccg cagcgctgta ggggtcttta cgtgttccaa ggggacagta gcccctgctc    780
ggccttcgag ttccactgcc taagtggcga gtgcatccac tccagctggc gctgtgatgg    840 tggcccccgac tgcaaggaca aatcgacga ggaaaactgc gctgtggcca cctgtcgccc    900
tgacgaattc cagtgctctg atggaaactg catccatggc agccggcagt gtgaccggga    960
atatgactgc aaggacatga gcgatgaagt tggctgcgtt aatgtgacac tctgcgaggg   1020
acccaacaag ttcaagtgtc acagcggcga atgcatcacc ctggacaaag tctgcaacat   1080
ggctagagac tgccgggact ggtcagatga acccatcaaa gagtgcggga ccaacgaatg   1140
cttggacaac aacggcggct gttcccacgt ctgcaatgac cttaagatcg gctacgagtg   1200
cctgtgcccc gacggcttcc agctggtggc ccagcgaaga tgcgaagata tcgatgagtg   1260
tcaggatccc gacacctgca gccagctctg cgtgaacctg gagggtggct acaagtgcca   1320
gtgtgaggaa ggcttccagc tggaccccca cacgaaggcc tgcaaggctg tgggctccat   1380
cgcctacctc ttcttcacca accggcacga ggtcaggaag atgacgctgg accggagcga   1440
gtacaccagc ctcatcccca acctgaggaa cgtggtcgct ctggacacgg aggtggccag   1500
caatagaatc tactggtctg acctgtccca gagaatgatc tgcagcaccc agcttgacag   1560
agcccacggc gtctcttcct atgacaccgt catcagcaga gacatccagg cccccgacgg   1620
gctggctgtg gactggatcc acagcaacat ctactggacc gactctgtcc tgggcactgt   1680
ctctgttgcg gataccaagg gcgtgaagag gaaaacgtta ttcagggaga acggctccaa   1740
gccaagggcc atcgtggtgg atcctgttca tggcttcatg tactggactg actggggaac   1800
tcccgccaag atcaagaaag ggggcctgaa tggtgtggac atctactcgc tggtgactga   1860
aaacattcag tgcccaatg gcatcaccct agatctcctc agtggccgcc tctactgggt   1920
tgactccaaa cttcactcca tctcaagcat cgatgtcaac gggggcaacc ggaagaccat   1980
cttggaggat gaaaagaggc tggcccaccc cttctccttg gccgtctttg aggacaaagt   2040
attttggaca gatatcatca acgaagccat tttcagtgcc aaccgcctca caggttccga   2100
tgtcaacttg ttggctgaaa acctactgtc cccagaggat atggttctct tccacaacct   2160
cacccagcca agaggagtga actggtgtga gaggaccacc ctgagcaatg gcggctgcca   2220
gtatctgtgc ctccctgccc cgcagatcaa ccccactcg cccaagttta cctgcgcctg   2280
cccggacggc atgctgctgg ccagggacat gaggagctgc ctcacagagg ctgaggctgc   2340
agtggccacc caggagacat ccaccgtcag gctaaaggtc agctccacag ccgtaaggac   2400
acagcacaca accacccgac tgttcccga cacctcccgg ctgcctgggg ccacccctgg   2460
gctcaccacg gtggagatag tgacaatgtc tcaccaagct ctgggcgacg ttgctggcag   2520
aggaaatgag aagaagccca gtagcgtgag ggctctgtcc attgtcctcc ccatcgtgct   2580
cctcgtcttc ctttgcctgg gggtcttcct tctatggaag aactggcggc ttaagaacat   2640
caacagcatc aactttgaca cccccgtcta tcagaagacc acagaggatg aggtccacat   2700
ttgccacaac caggacggct acagctaccc ctcgagacag atggtcagtc tggaggatga   2760
```

```
cgtggcgtga acatctgcct ggagtcccgt ccctgcccag aacccttcct gagacctcgc   2820
cggccttgtt ttattcaaag acagagaaga ccaaagcatt gcctgccaga gctttgtttt   2880
atatatttat tcatctggga ggcagaacag gcttcggaca gtgcccatgc aatggcttgg   2940
gttgggattt tggtttcttc ctttcctcgt gaaggataag agaaacaggc ccgggggggac  3000 caggatgaca cctccatttc tctccaggaa gttttgagtt tctctccacc gtgacacaat   3060
cctcaaacat ggaagatgaa agggggggg atgtcaggcc cagagaagca agtggctttc   3120
aacacacaac agcagatggc accaacggga cccccctggcc ctgcctcatc caccaatctc   3180
taagccaaac ccctaaactc aggagtcaac gtgtttacct cttctatgca agccttgcta   3240
gacagccagg ttagccttg ccctgtcacc cccgaatcat gacccaccca gtgtctttcg   3300
aggtgggttt gtaccttcct taagccagga aagggattca tggcgtcgga atgatctgg   3360 ctgaatccgt ggtggcaccg agaccaaact cattcaccaa atgatgccac ttcccagagg   3420
cagagcctga gtcactggtc acccttaata tttattaagt gcctgagaca cccggttacc   3480
ttggccgtga ggacacgtgg cctgcaccca ggtgtggctg tcaggacacc agcctggtgc   3540
ccatcctccc gaccctacc cacttccatt cccgtggtct ccttgcactt tctcagttca   3600
gagttgtaca ctgtgtacat ttggcatttg tgttattatt ttgcactgtt ttctgtcgtg   3660
tgtgttggga tgggatccca ggccagggaa agcccgtgtc aatgaatgcc ggggacagag   3720
aggggcaggt tgaccgggac ttcaaagccg tgatcgtgaa tatcgagaac tgccattgtc   3780
gtctttatgt ccgcccacct agtgcttcca cttctatgca aatgcctcca agccattcac   3840
ttccccaatc ttgtcgttga tgggtatgtg tttaaaacat gcacggtgag gccgggcgca   3900
gtggctcacg cctgtaatcc cagcactttg ggaggccgag gcgggtggat catgaggtca   3960
ggagatcgag accatcctgg ctaacacgtg aaacccccgtc tctactaaaa atacaaaaaa   4020
ttagccgggc gtggtggcgg gcacctgtag tcccagctac tcgggaggct gaggcaggag   4080
aatggtgtga acccgggaag cggagcttgc agtgagccga gattgcgcca ctgcagtccg   4140
cagtctggcc tgggcgacag agcgagactc cgtctcaaaa aaaaaaaaca aaaaaaaacc   4200
atgcatggtg catcagcagc ccatggcctc tggccaggca tggcgaggct gaggtgggag   4260
gatggtttga gctcaggcat ttgaggctgt cgtgagctat gattatgcca ctgcttttcca   4320 gcctgggcaa catagtaaga ccccatctct taaaaaatga atttggccag acacaggtgc   4380
ctcacgcctg taatcccagc actttgggag gctgagctgg atcacttgag ttcaggagtt   4440
ggagaccagg cctgagcaac aaagcgagat cccatctcta caaaaccaa aaagttaaaa   4500 atcagctggg tacggtggca cgtgcctgtg atcccagcta cttgggaggc tgaggcagga   4560
ggatcgcctg agcccaggag gtggaggttg cagtgagcca tgatcgagcc actgcactcc   4620
agcctgggca acagatgaag accctatttc agaaatacaa ctataaaaaa ataaataaat   4680
cctccagtct ggatcgtttg acgggacttc aggttctttc tgaaatcgcc gtgttactgt   4740
tgcactgatg tccggagaga cagtgacagc ctccgtcaga ctcccgcgtg aagatgtcac   4800
aagggattgg caattgtccc cagggacaaa acactgtgtc cccccagtg cagggaaccg   4860 tgataagcct ttctggtttc ggagcacgta atgcgtccc tgtacagata gtggggattt   4920
tttgttatgt ttgcactttg tatattggtt gaaactgtta tcacttatat atatatatat   4980
acacacatat ataaaaatc tatttatttt tgcaaaccct ggttgctgta tttgttcagt   5040
gactattctc ggggccctgt gtaggggggtt attgcctctg aaatgcctct tctttatgta   5100
caaagattat ttgcacgaac tggactgtgt gcaacgcttt ttgggagaat gatgtccccg   5160
```

-continued

```
ttgtatgtat gagtggcttc tgggagatgg gtgtcacttt ttaaaccact gtatagaagg    5220
tttttgtagc ctgaatgtct tactgtgatc aattaaattt cttaaatgaa ccaatttgtc    5280
taaaaaaaaa aa                                                        5292
```

<210> SEQ ID NO 7
<211> LENGTH: 641
<212> TYPE: PRT
<213> ORGANISM: Homo sapiens
<220> FEATURE:
<221> NAME/KEY: MISC_FEATURE
<223> OTHER INFORMATION: HSPA1B Accession number NP_005337.2

<400> SEQUENCE: 7

```
Met Ala Lys Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
                20                  25                  30

Gln Gly Asn Arg Thr Thr Pro Ser Tyr Val Ala Phe Thr Asp Thr Glu
            35                  40                  45

Arg Leu Ile Gly Asp Ala Ala Lys Asn Gln Val Ala Leu Asn Pro Gln
        50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
```

```
              325                 330                 335
   Val Gly Gly Ser Thr Arg Ile Pro Lys Val Gln Lys Leu Leu Gln Asp
           340                 345                 350

Phe Phe Asn Gly Arg Asp Leu Asn Lys Ser Ile Asn Pro Asp Glu Ala
       355                 360                 365

Val Ala Tyr Gly Ala Ala Val Gln Ala Ala Ile Leu Met Gly Asp Lys
   370                 375                 380

Ser Glu Asn Val Gln Asp Leu Leu Leu Leu Asp Val Ala Pro Leu Ser
   385                 390                 395                 400

Leu Gly Leu Glu Thr Ala Gly Gly Val Met Thr Ala Leu Ile Lys Arg
                   405                 410                 415

Asn Ser Thr Ile Pro Thr Lys Gln Thr Gln Ile Phe Thr Thr Tyr Ser
                   420                 425                 430

Asp Asn Gln Pro Gly Val Leu Ile Gln Val Tyr Glu Gly Glu Arg Ala
                   435                 440                 445

Met Thr Lys Asp Asn Asn Leu Leu Gly Arg Phe Glu Leu Ser Gly Ile
   450                 455                 460

Pro Pro Ala Pro Arg Gly Val Pro Gln Ile Glu Val Thr Phe Asp Ile
   465                 470                 475                 480

Asp Ala Asn Gly Ile Leu Asn Val Thr Ala Thr Asp Lys Ser Thr Gly
                       485                 490                 495

Lys Ala Asn Lys Ile Thr Ile Thr Asn Asp Lys Gly Arg Leu Ser Lys
                   500                 505                 510

Glu Glu Ile Glu Arg Met Val Gln Glu Ala Glu Lys Tyr Lys Ala Glu
               515                 520                 525

Asp Glu Val Gln Arg Glu Arg Val Ser Ala Lys Asn Ala Leu Glu Ser
   530                 535                 540

Tyr Ala Phe Asn Met Lys Ser Ala Val Glu Asp Glu Gly Leu Lys Gly
   545                 550                 555                 560

Lys Ile Ser Glu Ala Asp Lys Lys Lys Val Leu Asp Lys Cys Gln Glu
                   565                 570                 575

Val Ile Ser Trp Leu Asp Ala Asn Thr Leu Ala Glu Lys Asp Glu Phe
                   580                 585                 590

Glu His Lys Arg Lys Glu Leu Glu Gln Val Cys Asn Pro Ile Ile Ser
                   595                 600                 605

Gly Leu Tyr Gln Gly Ala Gly Gly Pro Gly Pro Gly Gly Phe Gly Ala
               610                 615                 620

Gln Gly Pro Lys Gly Gly Ser Gly Ser Gly Pro Thr Ile Glu Glu Val
   625                 630                 635                 640

Asp

<210> SEQ ID NO 8
<211> LENGTH: 2517
<212> TYPE: DNA
<213> ORGANISM: Homo sapiens
<220> FEATURE:
<221> NAME/KEY: misc_feature
<223> OTHER INFORMATION: HSPA1B Accession number NM_005346.5

<400> SEQUENCE: 8
aaacggccag cctgaggagc tgctgcgagg gtccgcttcg tctttcgaga gtgactcccg      60
cggtcccaag gctttccaga gcgaacctgt gcggctgcag gcaccggcgt gttgagtttc     120
cggcgttccg aaggactgag ctcttgtcgc ggatcccgtc cgccgtttcc agcccccagt     180
ctcagagcgg agcccacaga gcagggcacc ggcatggcca agccgcggc gatcggcatc     240
```

```
gacctgggca ccacctactc ctgcgtgggg gtgttccaac acggcaaggt ggagatcatc    300
gccaacgacc agggcaaccg caccaccccc agctacgtgg ccttcacgga caccgagcgg    360
ctcatcgggg atgcggccaa gaaccaggtg gcgctgaacc cgcagaacac cgtgtttgac    420
gcgaagcggc tgatcggccg caagttcggc gacccggtgg tgcagtcgga catgaagcac    480
tggcctttcc aggtgatcaa cgacggagac aagcccaagg tgcaggtgag ctacaagggg    540
gagaccaagg cattctaccc cgaggagatc tcgtccatgg tgctgaccaa gatgaaggag    600
atcgccgagg cgtacctggg ctacccggtg accaacgcgg tgatcaccgt gccggcctac    660
ttcaacgact cgcagcgcca ggccaccaag gatgcgggtg tgatcgcggg gctcaacgtg    720
ctgcggatca tcaacgagcc cacggccgcc gccatcgcct acggcctgga cagaacgggc    780
aagggggagc gcaacgtgct catctttgac ctgggcgggg gcaccttcga cgtgtccatc    840
ctgacgatcg acgacggcat cttcgaggtg aaggccacgg ccggggacac ccacctgggt    900
ggggaggact ttgacaacag gctggtgaac cacttcgtgg aggagttcaa gagaaaacac    960
aagaaggaca tcagccagaa caagcgagcc gtgaggcggc tgcgcaccgc ctgcgagagg   1020 gccaaggagga ccctgtcgtc cagcacccag gccagcctgg agatcgactc cctgtttgag   1080
ggcatcgact tctacacgtc catcaccagg gcgaggttcg aggagctgtg ctccgacctg   1140
ttccgaagca ccctggagcc cgtggagaag gctctgcgcg acgccaagct ggacaaggcc   1200
cagattcacg acctggtcct ggtcgggggc tccacccgca tccccaaggt gcagaagctg   1260
ctgcaggact tcttcaacgg gcgcgacctg aacaagagca tcaaccccga cgaggctgtg   1320
gcctacgggg cggcggtgca ggcggccatc ctgatggggg acaagtccga gaacgtgcag   1380
gacctgctgc tgctggacgt ggctcccctg tcgctggggc tggagacggc cggaggcgtg   1440
atgactgccc tgatcaagcg caactccacc atccccacca gcagacgca gatcttcacc    1500 acctactccg acaaccaacc cggggtgctg atccaggtgt acgagggcga gagggccatg   1560
acgaaagaca acaatctgtt ggggcgcttc gagctgagcg gcatccctcc ggccccccagg  1620 ggcgtgcccc agatcgaggt gaccttcgac atcgatgcca acggcatcct gaacgtcacg   1680
gccacggaca agagcaccgg caaggccaac aagatcacca tcaccaacga caagggccgc   1740
ctgagcaagg aggagatcga gcgcatggtg caggaggcgg agaagtacaa agcggaggac   1800
gaggtgcagc gcgagagggt gtcagccaag aacgccctgg agtcctacgc cttcaacatg   1860
aagagcgccg tggaggatga ggggctcaag ggcaagatca gcgaggcgga caagaagaag   1920
gttctggaca agtgtcaaga ggtcatctcg tggctgacg ccaacacctt ggccgagaag    1980
gacgagtttg agcacaagag gaaggagctg agcaggtgt gtaacccat catcagcgga     2040 ctgtaccagg gtgccggtgg tcccgggcct ggcggcttcg gggctcaggg tcccaaggga   2100
gggtctgggt caggccctac cattgaggag gtggattagg ggcctttgtt ctttagtatg   2160
tttgtctttg aggtggactg ttgggactca aggactttgc tgctgttttc ctatgtcatt   2220
tctgcttcag ctctttgctg cttcacttct ttgtaaagtt gtaacctgat ggtaattagc   2280
tggcttcatt atttttgtag tacaaccgat atgttcatta gaattctttg catttaatgt   2340
tgatactgta agggtgtttc gttcccttta atgaatcaa cactgccacc ttctgtacga    2400
gtttgtttgt ttttttttttt tttttttttt tttgcttggc gaaaacacta caaaggctgg   2460
gaatgtatgt ttttataatt tgtttattta aatatgaaaa ataaaatgtt aaacttt       2517
```

<210> SEQ ID NO 9

<211> LENGTH: 103
<212> TYPE: PRT
<213> ORGANISM: Homo sapiens
<220> FEATURE:
<221> NAME/KEY: MISC_FEATURE
<223> OTHER INFORMATION: G0S2 Accession number NP_056529.1

<400> SEQUENCE: 9

Met Glu Thr Val Gln Glu Leu Ile Pro Leu Ala Lys Glu Met Met Ala
1               5                   10                  15

Gln Lys Arg Lys Gly Lys Met Val Lys Leu Tyr Val Leu Gly Ser Val
            20                  25                  30

Leu Ala Leu Phe Gly Val Val Leu Gly Leu Met Glu Thr Val Cys Ser
        35                  40                  45

Pro Phe Thr Ala Ala Arg Arg Leu Arg Asp Gln Glu Ala Ala Val Ala
    50                  55                  60

Glu Leu Gln Ala Ala Leu Glu Arg Gln Ala Leu Gln Lys Gln Ala Leu
65                  70                  75                  80

Gln Glu Lys Gly Lys Gln Gln Asp Thr Val Leu Gly Gly Arg Ala Leu
                85                  90                  95

Ser Asn Arg Gln His Ala Ser
            100

<210> SEQ ID NO 10
<211> LENGTH: 876
<212> TYPE: DNA
<213> ORGANISM: Homo sapiens
<220> FEATURE:
<221> NAME/KEY: misc_feature
<223> OTHER INFORMATION: G0S2 Accession number NM_015714.4

<400> SEQUENCE: 10
tgccagcggc ggagtctcca actgggagag ctgcagctgc cgagaggagg agaacgctga      60
ggtcggtcgg accaacggac gcgctgaccg ctgccaactg cagctcgcgc tgcctcctgc     120
tcgcgccgtg ccactaaggt cattcccgcc tccgagagcc cagagccgag atggaaacgg     180
tccaggagct gatcccsctg gccaaggaga tgatggccca aaagcgcaag ggaagatgg     240 tgaagctgta cgtgctgggc agcgtgctgg ccctcttcgg cgtggtgctc ggcctgatgg     300
agactgtgtg cagccccttc acggccgcca gacgtctgcg ggaccaggag gcagccgtgg     360
cggagctgca ggccgccctg gagcgacagg ctctccagaa gcaagccctg caggagaaag     420
gcaagcagca ggacacggtc ctcggcggcc gggccctgtc caaccggcag cacgcctcct     480
aggaactgtg ggagaccagc ggagtgggag ggagacgcag tagacagaga cagaccgaga     540
gaggaatgga gagacagagg gggcgcgcgc acaggagcct gactccgctg ggagagtgca     600
ggagcacgtg ctgtttttta tttggactta acttcagaga aaccgctgac atctagaact     660
gacctaccac aagcatccac caaaggagtt tgggattgag ttttgctgct gtgcagcact     720
gcattgtcat gacattttcca acactgtgtg aattatctaa atgcgtctac cattttgcac     780
tagggaggaa ggataaatgc ttttatgtt attattatta attattacaa tgaccaccat     840
tttgcatttt gaaataaaaa aactttttat accata                               876

<210> SEQ ID NO 11
<211> LENGTH: 575
<212> TYPE: PRT
<213> ORGANISM: Homo sapiens
<220> FEATURE:
<221> NAME/KEY: MISC_FEATURE
<223> OTHER INFORMATION: BAG3 Accession number NP_004272.2

<400> SEQUENCE: 11

| | | | | | | | | | | | | | | |
|---|---|---|---|---|---|---|---|---|---|---|---|---|---|---|
|Met|Ser|Ala|Ala|Thr|His|Ser|Pro|Met|Met|Gln|Val|Ala|Ser|Gly|Asn|
|1| | | |5| | | | |10| | | | |15| |

Gly Asp Arg Asp Pro Leu Pro Pro Gly Trp Glu Ile Lys Ile Asp Pro
            20             25             30

Gln Thr Gly Trp Pro Phe Phe Val Asp His Asn Ser Arg Thr Thr Thr
       35            40            45

Trp Asn Asp Pro Arg Val Pro Ser Glu Gly Pro Lys Glu Thr Pro Ser
50              55             60

Ser Ala Asn Gly Pro Ser Arg Glu Gly Ser Arg Leu Pro Pro Ala Arg
65              70           75         80

Glu Gly His Pro Val Tyr Pro Gln Leu Arg Pro Gly Tyr Ile Pro Ile
           85            90          95

Pro Val Leu His Glu Gly Ala Glu Asn Arg Gln Val His Pro Phe His
        100          105         110

Val Tyr Pro Gln Pro Gly Met Gln Arg Phe Arg Thr Glu Ala Ala Ala
      115          120         125

Ala Ala Pro Gln Arg Ser Gln Ser Pro Leu Arg Gly Met Pro Glu Thr
130             135          140

Thr Gln Pro Asp Lys Gln Cys Gly Gln Val Ala Ala Ala Ala Ala Ala
145             150         155       160

Gln Pro Pro Ala Ser His Gly Pro Glu Arg Ser Gln Ser Pro Ala Ala
        165          170         175

Ser Asp Cys Ser Ser Ser Ser Ser Ala Ser Leu Pro Ser Ser Gly
      180          185         190

Arg Ser Ser Leu Gly Ser His Gln Leu Pro Arg Gly Tyr Ile Ser Ile
      195          200         205

Pro Val Ile His Glu Gln Asn Val Thr Arg Pro Ala Ala Gln Pro Ser
      210          215         220

Phe His Gln Ala Gln Lys Thr His Tyr Pro Ala Gln Gln Gly Glu Tyr
225             230         235       240

Gln Thr His Gln Pro Val Tyr His Lys Ile Gln Gly Asp Asp Trp Glu
        245          250         255

Pro Arg Pro Leu Arg Ala Ala Ser Pro Phe Arg Ser Ser Val Gln Gly
        260          265         270

Ala Ser Ser Arg Glu Gly Ser Pro Ala Arg Ser Ser Thr Pro Leu His
      275          280         285

Ser Pro Ser Pro Ile Arg Val His Thr Val Val Asp Arg Pro Gln Gln
290             295         300

Pro Met Thr His Arg Glu Thr Ala Pro Val Ser Gln Pro Glu Asn Lys
305             310         315       320

Pro Glu Ser Lys Pro Gly Pro Val Gly Pro Glu Leu Pro Pro Gly His
        325          330         335

Ile Pro Ile Gln Val Ile Arg Lys Glu Val Asp Ser Lys Pro Val Ser
      340          345         350

Gln Lys Pro Pro Pro Ser Glu Lys Val Glu Val Lys Val Pro Pro
      355          360         365

Ala Pro Val Pro Cys Pro Pro Pro Ser Pro Gly Pro Ser Ala Val Pro
      370          375         380

Ser Ser Pro Lys Ser Val Ala Thr Glu Glu Arg Ala Ala Pro Ser Thr
385             390         395       400

Ala Pro Ala Glu Ala Thr Pro Pro Lys Pro Gly Glu Ala Glu Ala Pro

```
                    405                 410                 415
Pro Lys His Pro Gly Val Leu Lys Val Glu Ala Ile Leu Glu Lys Val
            420                 425                 430
Gln Gly Leu Glu Gln Ala Val Asp Asn Phe Glu Gly Lys Lys Thr Asp
        435                 440                 445
Lys Lys Tyr Leu Met Ile Glu Glu Tyr Leu Thr Lys Glu Leu Leu Ala
    450                 455                 460
Leu Asp Ser Val Asp Pro Glu Gly Arg Ala Asp Val Arg Gln Ala Arg
465                 470                 475                 480
Arg Asp Gly Val Arg Lys Val Gln Thr Ile Leu Glu Lys Leu Glu Gln
                485                 490                 495
Lys Ala Ile Asp Val Pro Gly Gln Val Gln Val Tyr Glu Leu Gln Pro
            500                 505                 510
Ser Asn Leu Glu Ala Asp Gln Pro Leu Gln Ala Ile Met Glu Met Gly
        515                 520                 525
Ala Val Ala Ala Asp Lys Gly Lys Lys Asn Ala Gly Asn Ala Glu Asp
    530                 535                 540
Pro His Thr Glu Thr Gln Gln Pro Glu Ala Thr Ala Ala Ala Thr Ser
545                 550                 555                 560
Asn Pro Ser Ser Met Thr Asp Thr Pro Gly Asn Pro Ala Ala Pro
                565                 570                 575

<210> SEQ ID NO 12
<211> LENGTH: 2608
<212> TYPE: DNA
<213> ORGANISM: Homo sapiens
<220> FEATURE:
<221> NAME/KEY: misc_feature
<223> OTHER INFORMATION: BAG3 Accession number NM_004281.3

<400> SEQUENCE: 12
gcggagctcc gcatccaacc ccgggccgcg gccaacttct ctggactgga ccagaagttt      60
ctagccggcc agttgctacc tccctttatc tcctccttcc cctctggcag cgaggaggct     120
atttccagac acttccaccc ctctctggcc acgtcacccc cgcctttaat tcataaaggt     180
gccccggcgcc ggcttcccgg acacgtcggc ggcggagagg ggcccacggc ggcggcccgg    240
ccagagactc ggcgcccgga gccagcgccc cgcacccgcg ccccagcggg cagaccccaa     300
cccagcatga gcgccgccac ccactcgccc atgatgcagt ggcgtccgg caacggtgac     360
cgcgacccttt gcccccccgg atgggagatc aagatcgacc gcagaccgg ctggcccttc     420
ttcgtggacc acaacagccg caccactacg tggaacgacc cgcgcgtgcc ctctgagggc     480
cccaaggaga ctccatcctc tgccaatggc ccttcccggg agggctctag gctgccgcct     540
gctagggaag gccaccctgt gtaccccag ctccgaccag gctacattcc cattcctgtg     600
ctccatgaag gcgctgagaa ccggcaggtg cacccttttcc atgtctatcc ccagcctggg     660
atgcagcgat tccgaactga gcggcagca gcggctcctc agaggtccca gtcacctctg     720
cggggcatgc agaaaccac tcagccagat aaacagtgtg acaggtggc agcggcggcg     780
gcagcccagc cccagcctc ccacggacct gagcggtccc agtctccagc tgcctctgac     840
tgctcatcct catcctcctc ggccagcctg ccttcctccg gcaggagcag cctgggcagt     900
caccagctcc gcggggggta catctccatt ccggtgatac acgagcagaa cgttacccgg     960
ccagcagccc agccctcctt ccaccaagcc cagaagacgc actacccagc gcagcagggg    1020
gagtaccaga cccaccagcc tgtgtaccac aagatccagg gggatgactg ggagccccgg    1080
```

| | |
|---|---:|
| cccctgcggg cggcatcccc gttcaggtca tctgtccagg gtgcatcgag ccgggagggc | 1140 |
| tcaccagcca ggagcagcac gccactccac tcccctcgc ccatccgtgt gcacaccgtg | 1200 |
| gtcgacaggc ctcagcagcc catgacccat cgagaaactg cacctgtttc ccagcctgaa | 1260 |
| aacaaaccag aaagtaagcc aggcccagtt ggaccagaac tccctcctgg acacatccca | 1320 |
| attcaagtga tccgcaaaga ggtggattct aaacctgttt cccagaagcc cccacctccc | 1380 |
| tctgagaagg tagaggtgaa agttccccct gctccagttc cttgtcctcc tcccagccct | 1440 |
| ggcccttctg ctgtcccctc ttccccaag agtgtggcta cagaagagag ggcagccccc | 1500 |
| agcactgccc ctgcagaagc tacacctcca aaaccaggag aagccgaggc tcccccaaaa | 1560 |
| catccaggag tgctgaaagt ggaagccatc ctggagaagg tacaggggct ggagcaggct | 1620 |
| gtagacaact tgaaggcaa aagactgac aaaaagtacc tgatgatcga agagtatttg | 1680 |
| accaaagagc tgctggccct ggattcagtg accccgagg gacgagccga tgtgcgtcag | 1740 |
| gccaggagag acggtgtcag gaaggttcag accatcttgg aaaaacttga acagaaagcc | 1800 |
| attgatgtcc caggtcaagt ccaggtctat gaactccagc ccagcaacct tgaagcagat | 1860 |
| cagccactgc aggcaatcat ggagatgggt gccgtggcag cagacaaggg caagaaaaat | 1920 |
| gctggaaatg cagaagatcc ccacacagaa acccagcagc cagaagccac agcagcagcg | 1980 |
| acttcaaacc ccagcagcat gacagacacc cctggtaacc cagcagcacc gtagcctctg | 2040 |
| ccctgtaaaa atcagactcg gaaccgatgt gtgcttagg gaattttaag ttgcatgcat | 2100 |
| ttcagagact ttaagtcagt tggtttttat tagctgcttg gtatgcagta acttgggtgg | 2160 |
| aggcaaaaca ctaataaaag ggctaaaaag gaaaatgatg cttttcttct atattcttac | 2220 |
| tctgtacaaa taagaagtt gcttgttgtt tgagaagttt aaccccgttg cttgttgttc | 2280 |
| tgcagccctg tctacttggg cacccccacc acctgttagc tgtggttgtg cactgtcttt | 2340 |
| tgtagctctg gactggaggg gtagatgggg agtcaattac ccatcacata aatatgaaac | 2400 |
| atttatcaga aatgttgcca tttaatgag atgattttct tcatctcata attaaaatac | 2460 |
| ctgactttag agagagtaaa atgtgccagg agccatagga atatctgtat gttggatgac | 2520 |
| tttaatgcta cattttaaaa aaagaaaata aagtaataat ataactcaaa aaaaaaaaa | 2580 |
| aaaaaaaaaa aaaaaaaaaa aaaaaaaa | 2608 |

<210> SEQ ID NO 13
<211> LENGTH: 239
<212> TYPE: PRT
<213> ORGANISM: Homo sapiens
<220> FEATURE:
<221> NAME/KEY: MISC_FEATURE
<223> OTHER INFORMATION: TM4SF1 Accession number XP_016861874.1

<400> SEQUENCE: 13

Met Cys Tyr Gly Lys Cys Ala Arg Cys Ile Gly His Ser Leu Val Gly
1               5                   10                  15

Leu Ala Leu Leu Cys Ile Ala Ala Asn Ile Leu Leu Tyr Phe Pro Asn
            20                  25                  30

Gly Glu Thr Lys Tyr Ala Ser Glu Asn His Leu Ser Arg Phe Val Trp
        35                  40                  45

Phe Phe Ser Gly Ile Val Gly Gly Gly Leu Leu Met Leu Leu Pro Ala
    50                  55                  60

Phe Val Phe Ile Gly Leu Glu Gln Asp Asp Cys Cys Gly Cys Cys Gly
65                  70                  75                  80

His Glu Asn Cys Gly Lys Arg Cys Ala Met Leu Ser Ser Val Leu Ala

```
            85              90              95
Ala Leu Ile Gly Ile Ala Gly Ser Gly Tyr Cys Val Ile Val Ala Ala
            100             105             110

Leu Gly Leu Ala Glu Gly Pro Leu Cys Leu Asp Ser Leu Gly Gln Trp
            115             120             125

Asn Tyr Thr Phe Ala Ser Thr Glu Gly Gln Tyr Leu Leu Asp Thr Ser
            130             135             140

Thr Trp Ser Glu Cys Thr Glu Pro Lys His Ile Val Glu Trp Asn Val
145             150             155             160

Ser Leu Phe Ser Ile Leu Ala Leu Gly Gly Ile Glu Phe Ile Leu
                165             170             175

Cys Leu Ile Gln Val Ile Asn Gly Val Leu Gly Gly Ile Cys Gly Phe
            180             185             190

Cys Cys Ser His Gln Gln Val Arg Thr Cys Met Lys Ile Asn Met Thr
            195             200             205

Ala Lys Arg Thr Asn Pro Gly Gln Ser His Asn Leu Pro Leu Phe His
            210             215             220

Cys Asn Leu Tyr Ile Ser Leu Val Phe Ile Cys Lys Thr Leu Tyr
225             230             235
```

<210> SEQ ID NO 14
<211> LENGTH: 972
<212> TYPE: DNA
<213> ORGANISM: Homo sapiens
<220> FEATURE:
<221> NAME/KEY: misc_feature
<223> OTHER INFORMATION: TM4SF1 Accession number XM_017006385.2

<400> SEQUENCE: 14

```
aagggcggga cattcccccct gcctcttcgc accacagcca gagcctgcca ttaggaccaa      60
tgaaagcaaa gtacctcatc ccctcagtga ctaagaatcg cagtatttaa gaggtagcag     120
gaatgggctg agagtggtgt ttgctttctc caccagaagg gcacactttc atctaatttg     180
gggtatcact gagctgaaga caaagagaag ggggagaaaa cctagcagac caccatgtgc     240
tatgggaagt gtgcacgatg catcggacat tctctggtgg ggctcgccct cctgtgcatc     300
gcggctaata ttttgcttta cttttcccaat ggggaaacaa agtatgcctc cgaaaaccac     360
ctcagccgct tcgtgtggtt cttttctggc atcgtaggag gtggcctgct gatgctcctg     420
ccagcatttg tcttcattgg gctggaacag gatgactgct gtggctgctg tggccatgaa     480
aactgtggca acgatgtgc gatgctttct tctgtattgg ctgctctcat ggaattgca     540
ggatctggct actgtgtcat tgtggcagcc cttggcttag cagaaggacc actatgtctt     600
gattccctcg gccagtggaa ctacaccttt gccagcactg agggccagta ccttctggat     660
acctccacat ggtccgagtg cactgaaccc aagcacattg tggaatggaa tgtatctctg     720
ttttctatcc tcttggctct tggtggaatt gaattcatct tgtgtcttat tcaagtaata     780
aatggagtgc ttggaggcat atgtggcttt tgctgctctc accaacaggt aagaacctgc     840
atgaaaatca atatgactgc taaaagaacc aacccaggac agagccacaa tcttcctcta     900
tttcattgta atttatatat ttcacttgta ttcatttgta aaactttgta ttagtgtaac     960
atactcccca ca                                                          972
```

<210> SEQ ID NO 15
<211> LENGTH: 367
<212> TYPE: PRT
<213> ORGANISM: Homo sapiens
<220> FEATURE:
<221> NAME/KEY: MISC_FEATURE
<223> OTHER INFORMATION: DUSP1 Accession number NP_004408.1

<400> SEQUENCE: 15

```
Met Val Met Glu Val Gly Thr Leu Asp Ala Gly Gly Leu Arg Ala Leu
1               5                   10                  15

Leu Gly Glu Arg Ala Ala Gln Cys Leu Leu Leu Asp Cys Arg Ser Phe
            20                  25                  30

Phe Ala Phe Asn Ala Gly His Ile Ala Gly Ser Val Asn Val Arg Phe
        35                  40                  45

Ser Thr Ile Val Arg Arg Ala Lys Gly Ala Met Gly Leu Glu His
    50                  55                  60

Ile Val Pro Asn Ala Glu Leu Arg Gly Arg Leu Leu Ala Gly Ala Tyr
65                  70                  75                  80

His Ala Val Val Leu Leu Asp Glu Arg Ser Ala Ala Leu Asp Gly Ala
                85                  90                  95

Lys Arg Asp Gly Thr Leu Ala Leu Ala Ala Gly Ala Leu Cys Arg Glu
            100                 105                 110

Ala Arg Ala Ala Gln Val Phe Phe Leu Lys Gly Gly Tyr Glu Ala Phe
        115                 120                 125

Ser Ala Ser Cys Pro Glu Leu Cys Ser Lys Gln Ser Thr Pro Met Gly
    130                 135                 140

Leu Ser Leu Pro Leu Ser Thr Ser Val Pro Asp Ser Ala Glu Ser Gly
145                 150                 155                 160

Cys Ser Ser Cys Ser Thr Pro Leu Tyr Asp Gln Gly Gly Pro Val Glu
                165                 170                 175

Ile Leu Pro Phe Leu Tyr Leu Gly Ser Ala Tyr His Ala Ser Arg Lys
            180                 185                 190

Asp Met Leu Asp Ala Leu Gly Ile Thr Ala Leu Ile Asn Val Ser Ala
        195                 200                 205

Asn Cys Pro Asn His Phe Glu Gly His Tyr Gln Tyr Lys Ser Ile Pro
    210                 215                 220

Val Glu Asp Asn His Lys Ala Asp Ile Ser Ser Trp Phe Asn Glu Ala
225                 230                 235                 240

Ile Asp Phe Ile Asp Ser Ile Lys Asn Ala Gly Gly Arg Val Phe Val
                245                 250                 255

His Cys Gln Ala Gly Ile Ser Arg Ser Ala Thr Ile Cys Leu Ala Tyr
            260                 265                 270

Leu Met Arg Thr Asn Arg Val Lys Leu Asp Glu Ala Phe Glu Phe Val
        275                 280                 285

Lys Gln Arg Arg Ser Ile Ile Ser Pro Asn Phe Ser Phe Met Gly Gln
    290                 295                 300

Leu Leu Gln Phe Glu Ser Gln Val Leu Ala Pro His Cys Ser Ala Glu
305                 310                 315                 320

Ala Gly Ser Pro Ala Met Ala Val Leu Asp Arg Gly Thr Ser Thr Thr
                325                 330                 335

Thr Val Phe Asn Phe Pro Val Ser Ile Pro Val His Ser Thr Asn Ser
            340                 345                 350

Ala Leu Ser Tyr Leu Gln Ser Pro Ile Thr Thr Ser Pro Ser Cys
        355                 360                 365
```

<210> SEQ ID NO 16
<211> LENGTH: 2013
<212> TYPE: DNA

<213> ORGANISM: Homo sapiens
<220> FEATURE:
<221> NAME/KEY: misc_feature
<223> OTHER INFORMATION: DUSP1 Accession number NM_004417.4

<400> SEQUENCE: 16

```
gcgaaggaca tttgggctgt gtgtgcgacg cgggtcggag gggcagtcgg gggaaccgcg      60
aagaagccga ggagcccgga gccccgcgtg acgctcctct ctcagtccaa aagcggcttt     120
tggttcggcg cagagagacc cggggggtcta gcttttcctc gaaaagcgcc gccctgccct    180
tggccccgag aacagacaaa gagcaccgca gggccgatca cgctgggggc gctgaggccg     240
gccatggtca tggaagtggg caccctggac gctggaggcc tgcgggcgct gctgggggag     300
cgagcggcgc aatgcctgct gctggactgc cgctccttct tcgctttcaa cgccggccac     360
atcgccggct ctgtcaacgt gcgcttcagc accatcgtgc ggcgccgggc caagggcgcc     420
atgggcctgg agcacatcgt gcccaacgcc gagctccgcg gccgcctgct ggccggcgcc     480
taccacgccg tggtgttgct ggacgagcgc agcgccgccc tggacggcgc caagcgcgac     540
ggcaccctgg ccctggcggc cggcgcgctc tgccgcgagg cgcgcgccgc gcaagtcttc     600
ttcctcaaag gaggatacga agcgttttcg gcttcctgcc cggagctgtg cagcaaacag     660
tcgacccca tggggctcag ccttcccctg agtactagcg tccctgacag cgcggaatct      720
gggtgcagtt cctgcagtac cccactctac gatcagggtg gccgtgga aatcctgccc       780
tttctgtacc tgggcagtgc gtatcacgct cccgcaagg acatgctgga tgccttgggc      840
atcactgcct tgatcaacgt ctcagccaat tgtcccaacc attttgaggg tcactaccag     900
tacaagagca tccctgtgga ggacaaccac aaggcagaca tcagctcctg gttcaacgag    960
gccattgact tcatagactc catcaagaat gctggaggaa gggtgttttgt ccactgccag   1020
gcaggcattt cccggtcagc caccatctgc cttgcttacc ttatgaggac taatcgagtc   1080
aagctggacg aggcctttga gtttgtgaag cagaggcgaa gcatcatctc tcccaacttc   1140
agcttcatgg ccagctgct gcagtttgag tcccaggtgc tggctccgca ctgttcggca    1200
gaggctggga ccccgccat ggctgtgctc gaccgaggca cctccaccac caccgtgttc    1260
aacttccccg tctccatccc tgtccactcc acgaacagtg cgctgagcta ccttcagagc   1320
cccattacga cctctcccag ctgctgaaag gccacgggag gtgaggctct tcacatccca   1380
ttgggactcc atgctccttg agaggagaaa tgcaataact ctgggagggg ctcgagaggg   1440
ctggtcctta tttatttaac ttcacccgag ttcctctggg tttctaagca gttatggtga   1500
tgacttagcg tcaagacatt tgctgaactc agcacattcg ggaccaatat atagtgggta   1560
catcaagtcc atctgacaaa atggggcaga agagaaagga ctcagtgtgt gatccggttt   1620
cttttttgctc gcccctgttt tttgtagaat ctcttcatgc ttgacatacc taccagtatt   1680
attcccgacg acacatatac atatgagaat ataccttatt tattttttgtg taggtgtctg   1740
ccttcacaaa tgtcattgtc tactcctaga agaaccaaat acctcaattt ttgttttttga   1800
gtactgtact atcctgtaaa tatatcttaa gcaggtttgt tttcagcact gatggaaaat   1860
accagtgttg ggtttttttt tagttgccaa cagttgtatg tttgctgatt atttatgacc    1920
tgaaataata tatttcttct tctaagaaga cattttgtta cataaggatg acttttttat   1980
acaatggaat aaattatggc atttctattg aaa                                 2013
```

<210> SEQ ID NO 17
<211> LENGTH: 185
<212> TYPE: PRT

-continued

<213> ORGANISM: Homo sapiens
<220> FEATURE:
<221> NAME/KEY: MISC_FEATURE
<223> OTHER INFORMATION: ADM Accession number NP_001115.1

<400> SEQUENCE: 17

```
Met Lys Leu Val Ser Val Ala Leu Met Tyr Leu Gly Ser Leu Ala Phe
1               5                   10                  15

Leu Gly Ala Asp Thr Ala Arg Leu Asp Val Ala Ser Glu Phe Arg Lys
            20                  25                  30

Lys Trp Asn Lys Trp Ala Leu Ser Arg Gly Lys Arg Glu Leu Arg Met
        35                  40                  45

Ser Ser Ser Tyr Pro Thr Gly Leu Ala Asp Val Lys Ala Gly Pro Ala
    50                  55                  60

Gln Thr Leu Ile Arg Pro Gln Asp Met Lys Gly Ala Ser Arg Ser Pro
65                  70                  75                  80

Glu Asp Ser Ser Pro Asp Ala Ala Arg Ile Arg Val Lys Arg Tyr Arg
                85                  90                  95

Gln Ser Met Asn Asn Phe Gln Gly Leu Arg Ser Phe Gly Cys Arg Phe
            100                 105                 110

Gly Thr Cys Thr Val Gln Lys Leu Ala His Gln Ile Tyr Gln Phe Thr
        115                 120                 125

Asp Lys Asp Lys Asp Asn Val Ala Pro Arg Ser Lys Ile Ser Pro Gln
130                 135                 140

Gly Tyr Gly Arg Arg Arg Arg Ser Leu Pro Glu Ala Gly Pro Gly
145                 150                 155                 160

Arg Thr Leu Val Ser Ser Lys Pro Gln Ala His Gly Ala Pro Ala Pro
                165                 170                 175

Pro Ser Gly Ser Ala Pro His Phe Leu
            180                 185
```

<210> SEQ ID NO 18
<211> LENGTH: 1492
<212> TYPE: DNA
<213> ORGANISM: Homo sapiens
<220> FEATURE:
<221> NAME/KEY: misc_feature
<223> OTHER INFORMATION: ADM Accession number NM_001124.3

<400> SEQUENCE: 18

```
actcagtggt tcttggtga cactggatag aacagctcaa gccttgccac ttcgggcttc      60
tcactgcagc tgggcttgga cttcggagtt ttgccattgc cagtgggacg tctgagactt    120
tctccttcaa gtacttggca gatcactctc ttagcagggt ctgcgcttcg cagccgggat    180
gaagctggtt tccgtcgccc tgatgtacct gggttcgctc gccttcctag gcgctgacac    240
cgctcggttg gatgtcgcgt cggagtttcg aaagaagtgg aataagtggg ctctgagtcg    300
tgggaagagg gaactgcgga tgtccagcag ctaccccacc gggctcgctg acgtgaaggc    360
cgggcctgcc cagaccctta ttcggcccca ggacatgaag ggtgcctctc gaagcccga    420 agacagcagt ccggatgccg cccgcatccg agtcaagcgc taccgccaga gcatgaacaa    480
cttccagggc ctccggagct ttggctgccg cttcggacg tgcacggtgc agaagctggc    540
acaccagatc taccagttca cagataagga caaggacaac gtcgccccca ggagcaagat    600
cagcccccag ggctacggcc gccgcgcgcg cgctccctg cccgaggccg gcccgggtcg    660
gactctggtg tcttctaagc cacaagcaca cggggctcca gcccccccga gtggaagtgc    720
tccccacttt ctttaggatt taggcgccca tggtacaagg aatagtcgcg caagcatccc    780
```

```
gctggtgcct cccgggacga aggacttccc gagcggtgtg gggaccgggc tctgacagcc      840
ctgcggagac cctgagtccg ggaggcaccg tccggcggcg agctctggct ttgcaagggc      900
ccctccttct gggggcttcg cttccttagc cttgctcagg tgcaagtgcc ccaggggcg       960 gggtgcagaa gaatccgagt gtttgccagg cttaaggaga ggagaaactg agaaatgaat    1020
gctgagaccc ccggagcagg ggtctgagcc acagccgtgc tcgcccacaa actgatttct    1080
cacggcgtgt cacccacca gggcgcaagc ctcactatta cttgaacttt ccaaaaccta     1140
aagaggaaaa gtgcaatgcg tgttgtacat acagaggtaa ctatcaatat ttaagtttgt     1200
tgctgtcaag attttttttg taacttcaaa tatagagata tttttgtacg ttatatattg     1260
tattaagggc attttaaaag caattatatt gtcctcccct attttaagac gtgaatgtct    1320
cagcgaggtg taaagttgtt cgccgcgtgg aatgtgagtg tgtttgtgtg catgaaagag    1380
aaagactgat tacctcctgt gtggaagaag gaaacaccga gtctctgtat aatctattta    1440
cataaaatgg gtgatatgcg aacagcaaac caataaactg tctcaatgct ga           1492
```

BLOOD BIOMARKERS OF STROKE

RELATED APPLICATIONS

This application is a 35 U.S.C. § 371 filing of International Patent Application No. PCT/EP2019/062653, filed May 16, 2019, which claims priority to European Patent Application No. 18305600.1, filed May 16, 2018, the entire disclosures of which are hereby incorporated herein by reference.

FIELD OF INVENTION

The present invention relates to blood biomarkers of stroke and uses thereof in particular for monitoring the efficiency of therapies in ischemic stroke, for diagnosing purposes, short- and long-term prognosis as well as for risk assessment.

BACKGROUND OF INVENTION

Stroke is the second leading cause of death worldwide and the third leading cause of disability (McKay & Mensah, 2005. The atlas of heart disease and stroke ($1^{st}$ ed.). Geneva: World Health Organization). Cerebral focal ischemia, i.e., ischemic stroke, leads to severe and rapid tissue injury at the core of the infarction. After initial injury, brain cell death progresses slowly, extending to a heterogeneous area surrounding the core called the penumbra (Astrup et al., 1977. Stroke. 8(1):51-7). Salvaging the ischemic penumbra improves outcomes in terms of disability (Emberson et al., 2014. Lancet. 384(9958):1929-35).

To date, the only emergency therapeutic solution is recanalization through thrombolysis and/or thrombectomy. However, due to the short intervention window (<6 hours for recanalization and 4 h30 for thrombolysis) and haemorrhagic transformation risk, only a small percentage of acute ischemic stroke patients are eligible for this treatment. For example, it is estimated that among all patients arriving within 6 hours at a comprehensive stroke centre, only 10.5% are endovascular-eligible for thrombectomy according to AHA/ASA criteria (Vanacker et al., 2016. Stroke. 47(7): 1844-9).

Therefore, developing a new therapeutic strategy that widens the therapeutic window is a major public health issue. While numerous clinical trials failed before, since the advent of recanalization, neuroprotection associated to recanalization remains a potentially promising strategy to widen the therapeutic window. Increasing evidences suggest that peripheral proteins, nucleic acids, or lipids can be used to confirm diagnosis of ischemic stroke and to monitor disease progression. To date, however, none has been implemented in clinical practice (Kim et al., 2013. J Stroke. 15(1):27-37).

Biomarker tests refer to imaging, chemical, or other biological tests that can be used to qualitatively assess or quantitatively measure the presence or absence of one or several markers, indicative of the presence, progress or severity of a disease, or of the effects of a treatment. Central nervous system (CNS) imaging has made tremendous progresses, but identification of peripheral biological markers, on the other hand, is less advanced. Identifying blood biomarkers to be applied as robust biomarkers for CNS diseases and treatment is one of the most important challenges in modern neurology, as blood lacks direct contact with the brain.

The use of RNA in the blood as a diagnostic marker is an emerging field that is supported by its clinical application in the diagnosis of breast cancer, coronary artery disease and infectious disease (Rothstein & Jickling, 2013. Biomark Med. 7(1):37-47). Furthermore, RNA in the blood could be used as a companion diagnostic to assess the effect of a neuroprotective agent in early clinical trials. Studies of RNA as a diagnostic biomarker in acute ischemic stroke are rare, including only a small number of patients, among which only few patients at the acute phase of infarction (Tang et al., 2006. J Cereb Blood Flow Metab. 26(8):1089-102; Stamova et al., 2010. Stroke. 41(10):2171-7) for coding RNA. Recently, there has been burgeoning specific interest in non-coding RNA as potential biomarkers in stroke as a risk factor, but not at the acute phase of stroke infarction (Mick et al., 2017. Stroke. 48(4):828-834).

Transcriptome analysis has been used in many experimental studies with cerebral ischemia to measure gene expression changes. Most experimental transcriptomic studies were performed in rat and mouse on focal or global ischemia models (for a review, see Cox-Limpens et al., 2014. Brain Res. 1564:85-100). Besides ischemia, preconditioning has also been used as a tool to study endogenous brain protection in rodents. Results of microarray studies examining the transcriptome in these rodents have shown that immediate early genes, stress response genes, apoptosis genes, signal transduction genes, neurotransmission genes, ion channels genes, inflammation genes, cytoskeleton genes, ribosomal genes, and neurotrophic factors genes undergo expression changes during cerebral ischemia (Schmidt-Kastner et al., 2002. Brain Res Mol Brain Res. 108(1-2): 81-93; Buttner et al., 2009. Brain Res. 1252:1-14; Wang et al., 2011. Brain Res. 1372:13-21; Wang et al., 2012. Neuroscience. 220:100-8; Lu et al., 2004. J Neurosci Res. 77(6):843-57). However, to our knowledge, only few experiments were performed in primates (Cook et al., 2012. Nature. 483(7388):213-7; Cook & Tymianski, 2012. Neurotherapeutics. 9(2):371-9). Primates represent unique models to study brain ischemia since they have a highly similar genomes to human, as well as anatomical homology. For example, both primates and humans have non-lissencephalic brains (i.e., which exhibit convolutions in the cortex; gyrencephalic) as opposed to rodents, which do not. Furthermore, the transcriptomes of the cerebral cortex, in both human and chimpanzee, are very similar to each other and differ more between individuals than among regions within an individual (Khaitovich et al., 2004. Genome Res. 14(8):1462-73).

Four main reasons for the lack of success in translating neuroprotective therapies from animal studies to application in human have been identified (Moretti et al., 2015. Pharmacol Ther. 146:23-34; Timsit & Menn, 2012. Clin Pharmacol Ther. 91(2):327-32):

i) the poor quality of preclinical studies:
    for preclinical studies, the challenge in this field is being progressively overcome through the development of quality score criteria in preclinical studies, e.g., the STAIR criteria (Stroke Therapy Academic Industry Roundtable (STAIR), 1999. Stroke. 30(12): 2752-8; Fisher et al., 2009. Stroke. 40(6):2244-50); and of randomized blind studies in human (Llovera et al., 2015. Sci Transl Med. 7(299):299ra121).

ii) the absence of biologic companion pharmacodynamics biomarkers in early clinical development:
    companion biomarkers to develop drug is now more and more used. To gain confidence as to whether efficacy can be achieved in diseased patients with safe doses, prior to the big investments required in later stages, relatively short duration phase Ib clinical studies are conducted in small numbers of patients having the relevant disease. This is the most important application of some of the pharmacodynamic biomarkers (Zhao et al., 2015. *Clin Chem.* 61(11):1343-53).

iii) the absence of predictive imaging biomarkers in phase II human studies to estimate the penumbra:

selection of patients based on cerebral imaging to identify patients suitable to thrombectomy is now instrumental, as shown in the DAWN study to save the penumbra in selected patients (Jovin et al., 2017. *Int J Stroke.* 12(6):641-652; Chaisinanunkul et al., 2015. *Stroke.* 46(8): 2238-43; Nogueira et al., 2018. *N Engl J Med.* 378(1):11-21). Only a few studies in neuroprotection have carried out selection on the basis of penumbral characteristics (for a review, see Donnan et al., 2009. *Lancet Neurol.* 8(3):261-9). Today, this novel concept may offer a useful avenue for therapeutic intervention (Hillis & Baron, 2015. *Front Neurol.* 6:85) while waiting for recanalization or reperfusion.

iv) the absence of recanalization in fine:

thrombectomy is becoming the standard treatment at the acute phase of ischemic stroke, although its use will need to be spread. It is estimated that among all patients arriving within 6 hours at a comprehensive stroke centre, only 10.5% are "endovascular-eligible" for thrombectomy according to AHA/ASA criteria (Vanacker et al., 2016. *Stroke.* 47(7):1844-9).

A better understanding of gene expression patterns in tissue undergoing cerebral ischemia can improve diagnostic techniques. Here, the Inventors have explored the expression of genes after the onset of cerebral ischemia in the brain and blood. The study of macaque microarray expression data from brain and blood revealed that ischemic and non-ischemic samples can be distinguished based on their expression profiles, and the majority of highly differentially expressed genes are up-regulated in the ischemic scenario 6 hours after ischemia. A comparison of genes differentially expressed in the brain and the blood revealed a significant overlap of gene expression patterns. Surprisingly, the data showed that there is a common coding signature between the ischemic brain and the blood, which supports the development of blood transcriptomics as a tool for biopsy transcriptome expression profiling to characterize patients with ischemic stroke, to develop a companion biomarker for the assessment of neuroprotection drugs in patients.

SUMMARY

The present invention relates to a method of diagnosing a stoke in a subject, comprising:

i) determining a signature in a sample obtained from the subject by measuring the expression levels of at least two biomarkers selected from the group consisting of PTGS2, HMOX1, LDLR, HSPA1B, G0S2, BAG3, TM4SF1, DUSP1 and ADM,
preferably with the proviso that the at least two biomarkers do not consist in DUSP1 and ADM;

ii) comparing the signature determined in step i) with a reference signature; and iii) diagnosing the subject as being affected with a stroke when the expression levels of the at least two biomarkers in the signature are higher than the expression levels of the same at least two biomarkers in the reference signature.

In one embodiment, step i) of the method of diagnosing a stoke in a subject comprises measuring the expression levels of at least three biomarkers selected from the group consisting of PTGS2, HMOX1, LDLR, HSPA1B, G0S2, BAG3, TM4SF1, DUSP1 and ADM.

In one embodiment, step i) of the method of diagnosing a stoke in a subject comprises measuring the expression levels of PTGS2, HMOX1, LDLR, HSPA1B, G0S2, BAG3, TM4SF1, DUSP1 and ADM.

In one embodiment, the reference signature is obtained by measuring the expression levels of the biomarkers in a reference population of substantially healthy subjects.

In one embodiment, the method of diagnosing a stoke in a subject according to the present invention aims at distinguishing a stroke from a stroke mimic.

The present invention further relates to a method of determining whether a subject suffering from a stroke will achieve a response with a therapy, comprising:

i) determining a signature in a sample obtained from the subject by measuring the expression levels of at least two biomarkers selected from the group consisting of PTGS2, HMOX1, LDLR, HSPA1B, G0S2, BAG3, TM4SF1, DUSP1 and ADM;
preferably with the proviso that the at least two biomarkers do not consist in DUSP1 and ADM ii) comparing the signature determined in step i) with a reference signature; and iii) concluding that the subject achieves a response when the expression levels of the at least two biomarkers in the signature are lower than the expression levels of the same at least two biomarkers in the reference signature.

In one embodiment, step i) of the method of determining whether a subject suffering from a stroke will achieve a response with a therapy comprises measuring the expression levels of nine biomarkers selected from PTGS2, HMOX1, LDLR, HSPA1B, G0S2, BAG3, TM4SF1, DUSP1 and ADM.

In one embodiment, the reference signature is obtained by measuring the expression levels of the biomarkers in a sample obtained from the same subject before the start of said therapy.

The present invention relates to a method of determining whether a subject is at risk of having a stroke, comprising:

i) determining a signature in a sample obtained from the subject by measuring the expression levels of at least two biomarkers selected from the group consisting of PTGS2, HMOX1, LDLR, HSPA1B, G0S2, BAG3, TM4SF1, DUSP1 and ADM;
preferably with the proviso that the at least two biomarkers do not consist in DUSP1 and ADM ii) comparing the signature determined in step i) with a reference signature; and iii) concluding that the subject is at risk of having stroke when the expression levels of the at least three biomarkers in the signature are higher than the expression levels of the same at least three biomarkers in the reference signature.

In one embodiment, step i) of the method of determining whether a subject is at risk of having a stroke comprises measuring the expression levels of nine biomarkers selected from PTGS2, HMOX1, LDLR, HSPA1B, G0S2, BAG3, TM4SF1, DUSP1 and ADM.

In one embodiment, the reference signature is obtained by measuring the expression levels of the biomarkers in a reference population of substantially healthy subjects.

In one embodiment, the subject has experienced a stroke and the method of determining whether a subject is at risk of having a stroke is for determining if the subject is at risk of having a recurrent stroke.

In one embodiment pertaining to any of the methods of the invention, stroke is ischemic stroke, transient ischemic attack or a haemorrhagic stroke.

In one embodiment pertaining to any of the methods of the invention, the sample is a blood sample, plasma sample or serum sample.

In one embodiment pertaining to any of the methods of the invention, the sample is not a brain sample.

Definitions

In the present invention, the following terms have the following meanings:

"Stroke", as used herein, refers to any condition arising from a disruption, decrease, or stoppage of blood or oxygen flow to any part of the brain. In particular, the term "stroke" encompasses, without limitation, ischemic stroke, transient ischemic attack (TIA) and haemorrhagic stroke.

"Ischemic stroke" (or "IS") is an episode of neurological dysfunction caused by focal brain, spinal cord, or retina ischemia with evidence of acute infarction (Easton et al., 2009. Stroke. 40(6):2276-2293). There are at least four different causes of blood flow interruption:

(1) a blood clot in a blood vessel;
(2) a blood clot in the dural venous sinuses, which drain blood from the brain;
(3) an embolus clogging a blood vessel; and/or
(4) a sudden drop in blood pressure.

Stroke symptoms can, and frequently do, persist beyond 24 hours if the patient survives the initial damage.

"Transient ischemic attack" or "TIA", also called a mini-stroke, is a transient episode of neurological dysfunction caused by focal brain, spinal cord, or retinal ischemia without evidence of acute infarction. TIA symptoms can initially be the same as a stroke, except that the symptoms only last a short time, typically less than one hour, or at most 24 hours. Even though a TIA is temporary and usually does not cause brain tissue damages, a patient experiencing TIA is advised to seek professional help immediately because of the similarity in symptoms and because TIA is a risk factor for subsequent ischemic strokes.

"Haemorrhagic stroke" refers to a stroke resulting from any rupture in any of the vasculature of the brain.

Examples of acute neurological disorders that include stroke or involve aetiology or symptoms such as those observed with stroke are listed above, and include, without limitation, cerebral ischemia or infarction (including embolic occlusion and thrombotic occlusion), reperfusion following acute ischemia, perinatal hypoxic-ischemic injury, cardiac arrest, as well as intracranial haemorrhages of any type (such as, e.g., epidural, subdural, subarachnoid and intracerebral).

"Subject", as used herein, refers to an individual to be diagnosed or treated according to the methods of the present invention. Subjects include, but are not limited to, mammals (e.g., murines, simians, equines, bovines, porcines, canines, felines, and the like), preferably to primates, and most preferably to humans. In the context of the invention, the term "patient" generally refers to an individual seeking or having sought a diagnosis or treatment according to the methods of the present invention.

"Treating" or "treatment", as used herein, refers to alleviating a specified condition (such as a stroke), eliminating or reducing the symptoms of a condition (such as a stroke), slowing or eliminating the progression of a condition (such as a stroke), and preventing or delaying the initial occurrence of a condition (such as a stroke) in a subject, or preventing or delaying the reoccurrence of a condition (such as a stroke) in a previously afflicted subject.

"Diagnosing" or "diagnosis", as used herein, refers to assessing the development or progression of a condition (such as a stroke). As is known to a person skilled in the art, the assessment can be accurately performed for a statistically significant subject, although it is intended to be accurate for 100% of the subjects to be diagnosed. Statistical significance can be easily determined by a person skilled in the art using methods widely known in the art, e.g., confidence interval determination, p-value determination, t-test, Mann-Whitney test, and the like. Preferred confidence intervals are 90% or higher, 95% or higher, 97% or higher, 98% or higher, and 99%. A preferred p-value is 0.1, 0.05, 0.01, 0.005 or 0.0001. Preferably, diagnosis results according to the present invention will be accurate for 60% or more, 70% or more, 80% or more, or 90% or more of a group of subjects.

"Prognosing" or "prognosis", as used herein, refers to predicating the outcome for a subject with a condition (such as a stroke), after a particular treatment or intervention.

"Blood sample", as used herein, means any blood sample derived or obtained from a subject. Collections of blood samples can be performed by methods well known to those skilled in the art. In some embodiments, the blood sample is a whole blood sample, a serum sample or a plasma sample.

"Biomarker", as used herein, refers to a set of products of gene expression (e.g., mRNA and/or protein) that is associated with brain tissue or neural cells injury, and which can be correlated with stroke, but is preferably not correlated with other types of injury. Such specific biomarkers of stroke identified in the blood by the Inventors include PTGS2, HMOX1, LDLR, HSPA1B, G0S2, BAG3, TM4SF1, DUSP1 and ADM. These specific biomarkers are described in detail hereinafter.

In the present specification, the name of each of the genes of interest refers to the internationally recognised name of the corresponding gene, as found in internationally recognised gene sequences and protein sequences databases, in particular in the database from the HUGO Gene Nomenclature Committee, that is available at the following Internet address: gene.ucl.ac.uk/nomenclature/index.html. In the present specification, the name of each of the various biomarkers of interest may also refer to the internationally recognised name of the corresponding gene, as found in the internationally recognised gene sequences and protein sequences databases ENTRE ID, Genbank, TrEMBL or ENSEMBL. Through these internationally recognised sequence databases, the nucleic acid sequences corresponding to each of the gene of interest described herein may be retrieved by the one skilled in the art.

"PTGS2", as used herein, has its general meaning in the art and refers to prostaglandin-endoperoxide synthase 2 gene (Gene ID: 5743). An exemplary human amino acid sequence encoded by the "PTGS2" gene is represented by the NCBI reference sequence NP_000954.1 (SEQ ID NO: 1). An exemplary human mRNA sequence of the "PTGS2" gene is represented by the NCBI reference sequence NM 000963.4 (SEQ ID NO: 2), with the coding sequence (CDS) ranging from residue 134 to residue 1948 of SEQ ID NO: 2.

"HMOX1", as used herein, has its general meaning in the art and refers to heme oxygenase 1 gene (Gene ID: 3162). An exemplary human amino acid sequence encoded by the "HMOX1" gene is represented by the NCBI reference sequence NP_002124.1 (SEQ ID NO: 3). An exemplary human mRNA sequence of the "HMOX1" gene is represented by the NCBI reference sequence NM 002133.3 (SEQ ID NO: 4), with the coding sequence (CDS) ranging from residue 79 to residue 945 of SEQ ID NO: 4.

"LDLR", as used herein, has its general meaning in the art and refers to low density lipoprotein receptor gene (Gene ID: 3949). An exemplary human amino acid sequence encoded by the "LDLR" gene is represented by the NCBI reference sequence NP_000518.1 (SEQ ID NO: 5). An exemplary human mRNA sequence of the "LDLR" gene is represented by the NCBI reference sequence NM_000527.4 (SEQ ID NO: 6), with the coding sequence (CDS) ranging from residue 188 to residue 2770 of SEQ ID NO: 6.

"HSPA1B", as used herein, has its general meaning in the art and refers to heat shock protein family A (Hsp70) member 1B gene (Gene ID: 3304). An exemplary human amino acid sequence encoded by the "HSPA1B" gene is represented by the NCBI reference sequence NP_005337.2 (SEQ ID NO: 7). An exemplary human mRNA sequence of the "HSPA1B" gene is represented by the NCBI reference sequence NM_005346.5 (SEQ ID NO: 8), with the coding sequence (CDS) ranging from residue 214 to residue 2139 of SEQ ID NO: 8.

"G0S2", as used herein, has its general meaning in the art and refers to G0/G1 switch 2 gene (Gene ID: 50486). An exemplary human amino acid sequence encoded by the "G0S2" gene is represented by the NCBI reference sequence NP_056529.1 (SEQ ID NO: 9). An exemplary human mRNA sequence of the "G0S2" gene is represented by the NCBI reference sequence NM_015714.4 (SEQ ID NO: 10), with the coding sequence (CDS) ranging from residue 171 to residue 482 of SEQ ID NO: 10.

"BAG3", as used herein, has its general meaning in the art and refers to BCL2 associated athanogene 3 gene (Gene ID: 9531). An exemplary human amino acid sequence encoded by the "BAG3" gene is represented by the NCBI reference sequence NP_004272.2 (SEQ ID NO: 11). An exemplary human mRNA sequence of the "BAG3" gene is represented by the NCBI reference sequence NM_004281.3 (SEQ ID NO: 12), with the coding sequence (CDS) ranging from residue 307 to residue 2034 of SEQ ID NO: 12.

"TM4SF1", as used herein, has its general meaning in the art and refers to transmembrane 4 L six family member 1 gene (Gene ID: 4071). An exemplary human amino acid sequence encoded by the "TM4SF1" gene is represented by the NCBI reference sequence XP_016861874.1 (SEQ ID NO: 13). An exemplary human mRNA sequence of the "TM4SF1" gene is represented by the NCBI reference sequence XM_017006385.2 (SEQ ID NO: 14), with the coding sequence (CDS) ranging from residue 235 to residue 954 of SEQ ID NO: 14.

"DUSP1", as used herein, has its general meaning in the art and refers to dual specificity phosphatase 1 gene (Gene ID: 1843). An exemplary human amino acid sequence encoded by the "DUSP1" gene is represented by the NCBI reference sequence NP_004408.1 (SEQ ID NO: 15). An exemplary human mRNA sequence of the "DUSP1" gene is represented by the NCBI reference sequence NM_004417.4 (SEQ ID NO: 16), with the coding sequence (CDS) ranging from residue 244 to residue 1347 of SEQ ID NO: 16.

"ADM", as used herein, has its general meaning in the art and refers to adrenomedullin gene (Gene ID: 133). An exemplary human amino acid sequence encoded by the "ADM" gene is represented by the NCBI reference sequence NP_001115.1 (SEQ ID NO: 17). An exemplary human mRNA sequence of the "ADM" gene is represented by the NCBI reference sequence NM_001124.3 (SEQ ID NO: 18), with the coding sequence (CDS) ranging from residue 179 to residue 736 of SEQ ID NO: 18.

DETAILED DESCRIPTION

The present invention relates to a signature of stroke, wherein said signature comprises biomarkers whose expression levels are specific or indicative of a stroke. Such biomarkers will be hereinafter referred to as a "stroke biomarker".

In one embodiment, the signature of the invention is specific or indicative of stroke. In one embodiment, the signature of the invention is specific or indicative of ischemic stroke, mini-stroke (also known as transient ischemic attack, TIA) and/or haemorrhagic stroke (in particular, haemorrhagic stroke caused by intracerebral haemorrhage). In one embodiment, the signature of the invention is specific or indicative of ischemic stroke. In one embodiment, the signature of the invention is specific or indicative of transient ischemic attack. In one embodiment, the signature of the invention is specific or indicative of haemorrhagic stroke (in particular, haemorrhagic stroke caused by intracerebral haemorrhage).

In one embodiment, the signature of the invention comprises or consists of at least one stroke biomarker. In one embodiment, the signature of the invention comprises or consists of at least two stroke biomarkers. In one embodiment, the signature of the invention comprises or consists of at least three stroke biomarkers. In one embodiment, the signature of the invention comprises or consists of at least four stroke biomarkers. In one embodiment, the signature of the invention comprises or consists of at least five stroke biomarkers. In one embodiment, the signature of the invention comprises or consists of at least six stroke biomarkers. In one embodiment, the signature of the invention comprises or consists of at least seven stroke biomarkers. In one embodiment, the signature of the invention comprises or consists of at least eight stroke biomarkers. In one embodiment, the signature of the invention comprises or consists of at least nine stroke biomarkers.

In one embodiment, stroke biomarkers are selected from the group comprising or consisting of HSPA1B, NPAS4, DNAJB1, ATF3, HSPB1, RRAD, NR4A1, CYR61, C-FOS, GADD45G, RGS1, ARC, EGR4, PTGS2, RGS2, CCL3, BAG3, EGR2, HSPA4L, ADM, TM4SF1, EGR1, DUSP1, BTG2, LOC715456, HMOX1, LDLR, DNAJA4, MCL1, HSPA6, GADD45B, IL6, ADFP, HES4, DUSP5, GEM and G0S2.

In one embodiment, stroke biomarkers are selected from the group comprising or consisting of PTGS2, HMOX1, LDLR, HSPA1B, G0S2, BAG3, TM4SF1, DUSP1 and ADM.

In one embodiment, stroke biomarkers are selected from the group comprising or consisting of PTGS2, HMOX1, LDLR, HSPA1B, G0S2, BAG3 and TM4SF1.

In one embodiment, the signature of the invention comprises or consists of at least one stroke biomarker selected from the group comprising or consisting of HSPA1B, NPAS4, DNAJB1, ATF3, HSPB1, RRAD, NR4A1, CYR61, C-FOS, GADD45G, RGS1, ARC, EGR4, PTGS2, RGS2, CCL3, BAG3, EGR2, HSPA4L, ADM, TM4SF1, EGR1, DUSP1, BTG2, LOC715456, HMOX1, LDLR, DNAJA4, MCL1, HSPA6, GADD45B, IL6, ADFP, HES4, DUSP5, GEM and G0S2.

In one embodiment, the signature of the invention comprises or consists of at least one stroke biomarker selected from the group comprising or consisting of PTGS2, HMOX1, LDLR, HSPA1B, G0S2, BAG3, TM4SF1, DUSP1 and ADM.

In one embodiment, the signature of the invention comprises or consists of at least one stroke biomarker selected from the group comprising or consisting of PTGS2, HMOX1, LDLR, HSPA1B, G0S2, BAG3 and TM4SF1.

In one embodiment, the signature of the invention comprises or consists of at least two stroke biomarkers selected from the group comprising or consisting of HSPA1B, NPAS4, DNAJB1, ATF3, HSPB1, RRAD, NR4A1, CYR61, C-FOS, GADD45G, RGS1, ARC, EGR4, PTGS2, RGS2, CCL3, BAG3, EGR2, HSPA4L, ADM, TM4SF1, EGR1, DUSP1, BTG2, LOC715456, HMOX1, LDLR, DNAJA4, MCL1, HSPA6, GADD45B, IL6, ADFP, HES4, DUSP5, GEM and G0S2.

In one embodiment, the signature of the invention comprises or consists of at least two stroke biomarkers selected from the group comprising or consisting of PTGS2, HMOX1, LDLR, HSPA1B, G0S2, BAG3, TM4SF1, DUSP1 and ADM.

In one embodiment, the signature of the invention comprises or consists of at least two stroke biomarkers selected from the group comprising or consisting of PTGS2, HMOX1, LDLR, HSPA1B, G0S2, BAG3 and TM4SF1.

In one embodiment, the signature of the invention comprises or consists of at least two stroke biomarkers selected from the group comprising or consisting of PTGS2, HMOX1, LDLR, HSPA1B, G0S2, BAG3, TM4SF1, DUSP1 and ADM, with the proviso that the at least two biomarkers do not consist in DUSP1 and ADM.

In one embodiment, the signature of the invention comprises or consists of at least three stroke biomarkers selected from the group comprising or consisting of HSPA1B, NPAS4, DNAJB1, ATF3, HSPB1, RRAD, NR4A1, CYR61, C-FOS, GADD45G, RGS1, ARC, EGR4, PTGS2, RGS2, CCL3, BAG3, EGR2, HSPA4L, ADM, TM4SF1, EGR1, DUSP1, BTG2, LOC715456, HMOX1, LDLR, DNAJA4, MCL1, HSPA6, GADD45B, IL6, ADFP, HES4, DUSP5, GEM and G0S2.

In one embodiment, the signature of the invention comprises or consists of at least three stroke biomarkers selected from the group comprising or consisting of, PTGS2, HMOX1, LDLR, HSPA1B, G0S2, BAG3, TM4SF1, DUSP1 and ADM.

In one embodiment, the signature of the invention comprises or consists of at least three stroke biomarkers selected from the group comprising or consisting of, PTGS2, HMOX1, LDLR, HSPA1B, G0S2, BAG3 and TM4SF1.

In one embodiment, the signature of the invention comprises or consists of at least four stroke biomarkers selected from the group comprising or consisting of, HSPA1B, NPAS4, DNAJB1, ATF3, HSPB1, RRAD, NR4A1, CYR61, C-FOS, GADD45G, RGS1, ARC, EGR4, PTGS2, RGS2, CCL3, BAG3, EGR2, HSPA4L, ADM, TM4SF1, EGR1, DUSP1, BTG2, LOC715456, HMOX1, LDLR, DNAJA4, MCL1, HSPA6, GADD45B, IL6, ADFP, HES4, DUSP5, GEM and G0S2.

In one embodiment, the signature of the invention comprises or consists of at least four stroke biomarkers selected from the group comprising or consisting of, PTGS2, HMOX1, LDLR, HSPA1B, G0S2, BAG3, TM4SF1, DUSP1 and ADM.

In one embodiment, the signature of the invention comprises or consists of at least four stroke biomarkers selected from the group comprising or consisting of, PTGS2, HMOX1, LDLR, HSPA1B, G0S2, BAG3 and TM4SF1.

In one embodiment, the signature of the invention comprises or consists of at least five stroke biomarkers selected from the group comprising or consisting of, HSPA1B, NPAS4, DNAJB1, ATF3, HSPB1, RRAD, NR4A1, CYR61, C-FOS, GADD45G, RGS1, ARC, EGR4, PTGS2, RGS2, CCL3, BAG3, EGR2, HSPA4L, ADM, TM4SF1, EGR1, DUSP1, BTG2, LOC715456, HMOX1, LDLR, DNAJA4, MCL1, HSPA6, GADD45B, IL6, ADFP, HES4, DUSP5, GEM and G0S2.

In one embodiment, the signature of the invention comprises or consists of at least five stroke biomarkers selected from the group comprising or consisting of, PTGS2, HMOX1, LDLR, HSPA1B, G0S2, BAG3, TM4SF1, DUSP1 and ADM.

In one embodiment, the signature of the invention comprises or consists of at least five stroke biomarkers selected from the group comprising or consisting of, PTGS2, HMOX1, LDLR, HSPA1B, G0S2, BAG3 and TM4SF1.

In one embodiment, the signature of the invention comprises or consists of at least six stroke biomarkers selected from the group comprising or consisting of, HSPA1B, NPAS4, DNAJB1, ATF3, HSPB1, RRAD, NR4A1, CYR61, C-FOS, GADD45G, RGS1, ARC, EGR4, PTGS2, RGS2, CCL3, BAG3, EGR2, HSPA4L, ADM, TM4SF1, EGR1, DUSP1, BTG2, LOC715456, HMOX1, LDLR, DNAJA4, MCL1, HSPA6, GADD45B, IL6, ADFP, HES4, DUSP5, GEM and G0S2.

In one embodiment, the signature of the invention comprises or consists of at least six stroke biomarkers selected from the group comprising or consisting of, PTGS2, HMOX1, LDLR, HSPA1B, G0S2, BAG3, TM4SF1, DUSP1 and ADM.

In one embodiment, the signature of the invention comprises or consists of at least six stroke biomarkers selected from the group comprising or consisting of, PTGS2, HMOX1, LDLR, HSPA1B, G0S2, BAG3 and TM4SF1.

In one embodiment, the signature of the invention comprises or consists of at least seven stroke biomarkers selected from the group comprising or consisting of, HSPA1B, NPAS4, DNAJB1, ATF3, HSPB1, RRAD, NR4A1, CYR61, C-FOS, GADD45G, RGS1, ARC, EGR4, PTGS2, RGS2, CCL3, BAG3, EGR2, HSPA4L, ADM, TM4SF1, EGR1, DUSP1, BTG2, LOC715456, HMOX1, LDLR, DNAJA4, MCL1, HSPA6, GADD45B, IL6, ADFP, HES4, DUSP5, GEM and G0S2.

In one embodiment, the signature of the invention comprises or consists of at least seven stroke biomarkers selected from the group comprising or consisting of, PTGS2, HMOX1, LDLR, HSPA1B, G0S2, BAG3, TM4SF1, DUSP1 and ADM.

In one embodiment, the signature of the invention comprises or consists of at least seven stroke biomarkers selected from the group comprising or consisting of, PTGS2, HMOX1, LDLR, HSPA1B, G0S2, BAG3 and TM4SF1.

In one embodiment, the signature of the invention comprises or consists of at least eight stroke biomarkers selected from the group comprising or consisting of, HSPA1B, NPAS4, DNAJB1, ATF3, HSPB1, RRAD, NR4A1, CYR61, C-FOS, GADD45G, RGS1, ARC, EGR4, PTGS2, RGS2, CCL3, BAG3, EGR2, HSPA4L, ADM, TM4SF1, EGR1, DUSP1, BTG2, LOC715456, HMOX1, LDLR, DNAJA4, MCL1, HSPA6, GADD45B, IL6, ADFP, HES4, DUSP5, GEM and G0S2.

In one embodiment, the signature of the invention comprises or consists of at least eight stroke biomarkers selected from the group comprising or consisting of, PTGS2, HMOX1, LDLR, HSPA1B, G0S2, BAG3, TM4SF1, DUSP1 and ADM.

In one embodiment, the signature of the invention comprises or consists of at least nine stroke biomarkers selected from the group comprising or consisting of, HSPA1B, NPAS4, DNAJB1, ATF3, HSPB1, RRAD, NR4A1, CYR61, C-FOS, GADD45G, RGS1, ARC, EGR4, PTGS2, RGS2, CCL3, BAG3, EGR2, HSPA4L, ADM, TM4SF1, EGR1, DUSP1, BTG2, LOC715456, HMOX1, LDLR, DNAJA4, MCL1, HSPA6, GADD45B, IL6, ADFP, HES4, DUSP5, GEM and G0S2.

In one embodiment, the signature of the invention comprises or consists of at least nine stroke biomarkers selected from the group comprising or consisting of, PTGS2, HMOX1, LDLR, HSPA1B, G0S2, BAG3, TM4SF1, DUSP1 and ADM.

The present invention thus also relates to a signature of stroke comprising or consisting of one or several biomarker(s) whose expression level(s) is/are different between a subject affected with a stroke and a substantially healthy subject.

In one embodiment, the signature of the invention is specific or indicative of stroke if the expression level of at least one stroke biomarker selected from the group comprising or consisting of, PTGS2, HMOX1, LDLR, HSPA1B, G0S2, BAG3, TM4SF1, DUSP1 and ADM is upregulated, as compared to a reference signature.

In one embodiment, the signature of the invention is specific or indicative of stroke if the expression level of at least one stroke biomarker selected from the group comprising or consisting of, PTGS2, HMOX1, LDLR, HSPA1B, G0S2, BAG3 and TM4SF1 is upregulated, as compared to a reference signature.

In one embodiment, the signature of the invention is specific or indicative of stroke if the expression level of at least two stroke biomarkers selected from the group comprising or consisting of, PTGS2, HMOX1, LDLR, HSPA1B, G0S2, BAG3, TM4SF1, DUSP1 and ADM is upregulated, as compared to a reference signature; preferably with the proviso that the at least two biomarkers do not consist in DUSP1 and ADM In one embodiment, the signature of the invention is specific or indicative of stroke if the expression level of at least two stroke biomarkers selected from the group comprising or consisting of, PTGS2, HMOX1, LDLR, HSPA1B, G0S2, BAG3 and TM4SF1 is upregulated, as compared to a reference signature.

In one embodiment, the signature of the invention is specific or indicative of stroke if the expression level of at least three stroke biomarkers selected from the group comprising or consisting of, PTGS2, HMOX1, LDLR, HSPA1B, G0S2, BAG3, TM4SF1, DUSP1 and ADM is upregulated, as compared to a reference signature.

In one embodiment, the signature of the invention is specific or indicative of stroke if the expression level of at least three stroke biomarkers selected from the group comprising or consisting of, PTGS2, HMOX1, LDLR, HSPA1B, G0S2, BAG3 and TM4SF1 is upregulated, as compared to a reference signature.

In one embodiment, the signature of the invention is specific or indicative of stroke if the expression level of at least four stroke biomarkers selected from the group comprising or consisting of, PTGS2, HMOX1, LDLR, HSPA1B, G0S2, BAG3, TM4SF1, DUSP1 and ADM is upregulated, as compared to a reference signature.

In one embodiment, the signature of the invention is specific or indicative of stroke if the expression level of at least four stroke biomarkers selected from the group comprising or consisting of, PTGS2, HMOX1, LDLR, HSPA1B, G0S2, BAG3 and TM4SF1 is upregulated, as compared to a reference signature.

In one embodiment, the signature of the invention is specific or indicative of stroke if the expression level of at least five stroke biomarkers selected from the group comprising or consisting of, PTGS2, HMOX1, LDLR, HSPA1B, G0S2, BAG3, TM4SF1, DUSP1 and ADM is upregulated, as compared to a reference signature.

In one embodiment, the signature of the invention is specific or indicative of stroke if the expression level of at least five stroke biomarkers selected from the group comprising or consisting of, PTGS2, HMOX1, LDLR, HSPA1B, G0S2, BAG3 and TM4SF1 is upregulated, as compared to a reference signature.

In one embodiment, the signature of the invention is specific or indicative of stroke if the expression level of at least six stroke biomarkers selected from the group comprising or consisting of, PTGS2, HMOX1, LDLR, HSPA1B, G0S2, BAG3, TM4SF1, DUSP1 and ADM is upregulated, as compared to a reference signature.

In one embodiment, the signature of the invention is specific or indicative of stroke if the expression level of at least six stroke biomarkers selected from the group comprising or consisting of, PTGS2, HMOX1, LDLR, HSPA1B, G0S2, BAG3 and TM4SF1 is upregulated, as compared to a reference signature.

In one embodiment, the signature of the invention is specific or indicative of stroke if the expression level of at least seven stroke biomarkers selected from the group comprising or consisting of, PTGS2, HMOX1, LDLR, HSPA1B, G0S2, BAG3, TM4SF1, DUSP1 and ADM is upregulated, as compared to a reference signature.

In one embodiment, the signature of the invention is specific or indicative of stroke if the expression level of at least seven stroke biomarkers selected from the group comprising or consisting of, PTGS2, HMOX1, LDLR, HSPA1B, G0S2, BAG3 and TM4SF1 is upregulated, as compared to a reference signature.

In one embodiment, the signature of the invention is specific or indicative of stroke if the expression level of at least eight stroke biomarkers selected from the group comprising or consisting of, PTGS2, HMOX1, LDLR, HSPA1B, G0S2, BAG3, TM4SF1, DUSP1 and ADM is upregulated, as compared to a reference signature.

In one embodiment, the signature of the invention is specific or indicative of stroke if the expression level of at least nine stroke biomarkers selected from the group comprising or consisting of, PTGS2, HMOX1, LDLR, HSPA1B, G0S2, BAG3, TM4SF1, DUSP1 and ADM is upregulated, as compared to a reference signature.

In one embodiment, the expression level of the stroke biomarkers of the invention in a sample from a subject, preferably a bodily fluid sample, more preferably a blood sample, can be determined using standard protocols known in the art.

In one embodiment, the expression level of the stroke biomarkers of the invention corresponds to their transcription levels (i.e., the expression of the mRNA) or to their translation levels (i.e., expression of the protein).

In one embodiment, the expression level of the stroke biomarkers is assessed at the protein level, i.e., at the translation level, in a sample, preferably a bodily fluid sample, more preferably a blood sample, from a subject. In this embodiment, the signature according to the present invention may be referred to as a proteomic signature.

Methods for determining a protein level in a sample are well known in the art. Examples of such methods include, but are not limited to, immunohistochemistry, multiplex methods (Luminex), western blot, enzyme-linked immunosorbent assay (ELISA), sandwich ELISA, fluorescent-linked immunosorbent assay (FLISA), enzyme immunoassay (EIA), radioimmunoassay (RIA), mass spectrometry (MS), a microarray, and the like, or any combination thereof.

Mass spectrometry (MS) can be used to resolve different forms of a protein because the different forms typically have different masses that can be resolved by mass spectrometry. Accordingly, if one form of a polypeptide or protein is a better biomarker for a disease than another form of the biomarker, mass spectrometry can be used to specifically detect and measure the useful form. MS can include time-of-flight (TOF) MS (e.g., matrix-assisted laser desorption/ionization (MALDI)-TOF MS), surface-enhanced laser desorption/ionization (MELDI) MS, electrospray ionization MS, or Fourier transform ion cyclotron resonance (FT-ICR) MS.

Immunoassays typically comprise contacting the sample with a binding partner capable of selectively interacting with the biomarker in the sample. In some embodiments, the binding partners are antibodies, such as, e.g., monoclonal antibodies or even aptamers. For example, the binding may be detected through use of a competitive immunoassay, a non-competitive assay system using techniques such as western blots, a radioimmunoassay, an ELISA, a "sandwich" immunoassay, an immunoprecipitation assay, a precipitin reaction, a gel diffusion precipitin reaction, an immunodiffusion assay, an agglutination assay, a complement fixation assay, an immunoradiometric assay, a fluorescent immunoassay, a protein A immunoassay, an immunoprecipitation assay, an immunohistochemical assay, a competition or sandwich ELISA, a radioimmunoassay, a Western blot assay, an immunohistological assay, an immunocytochemical assay, a dot blot assay, a fluorescence polarization assay, a scintillation proximity assay, a homogeneous time resolved fluorescence assay, a IAsys analysis, and a BIAcore analysis. The aforementioned assays generally involve the binding of the partner (i.e., antibody or aptamer) to a solid support. Solid supports which can be used in the practice of the invention include substrates such as nitrocellulose (e.g., in membrane or microtiter well form), polyvinylchloride (e.g., sheets or microtiter wells), polystyrene latex (e.g., beads or microtiter plates), polyvinylidene fluoride, diazotized paper, nylon membranes, activated beads, magnetically responsive beads, and the like.

A multiplex assay can include a phage display, an antibody profiling, or an assay using a Luminex platform. A microarray for analysing a profile of polypeptides can include analytical microarrays, functional protein microarrays, or reverse phase protein microarrays. In some cases, a profile of polypeptides or proteins can be measured by a proteomic scan (e.g. a whole proteomic scan) using a proteomic microarray.

In one embodiment, the expression level of the stroke biomarkers is assessed at the nucleic acid level (i.e., RNA), i.e., at the transcription level, in a sample, preferably a bodily fluid sample, more preferably a blood sample, from a subject. In this embodiment, the signature according to the present invention may be referred to as a transcriptomic signature.

Methods for assessing the transcription level of a biomarker are well known in the art. Examples of such methods include, but are not limited to, polymerase chain reaction (PCR), RT-PCR, RT-qPCR, Northern Blot, hybridization techniques such as, for example, use of microarrays, and combination thereof including but not limited to, hybridization of amplicons obtained by RT-PCR, sequencing such as, for example, next-generation DNA sequencing (NGS) or RNA-seq (also known as "whole transcriptome shotgun sequencing") and the like, or any combination thereof.

Conventional methods typically involve polymerase chain reaction (PCR). For instance, U.S. Pat. Nos. 4,683,202, 4,683,195, 4,800,159 and 4,965,188 disclose conventional PCR techniques. PCR typically employs two oligonucleotide primers that bind to a selected target nucleic acid sequence. Primers useful in the present invention include oligonucleotides capable of acting as a point of initiation of nucleic acid synthesis within the target nucleic acid sequence. A primer can be purified from a restriction digest by conventional methods, or it can be produced synthetically. PCR involves the use of a thermostable polymerase. The term "thermostable polymerase" refers to a polymerase enzyme that is heat stable, i.e., the enzyme catalyses the formation of primer extension products complementary to a template and does not irreversibly denature when subjected to the elevated temperatures for the time necessary to effect denaturation of double-stranded template nucleic acids. Thermostable polymerases have been isolated from *Thermus fiavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished. Typically, the polymerase is a Taq polymerase (i.e., *Thermus aquaticus* polymerase).

Quantitative PCR (qPCR) is typically carried out in a thermal cycler with the capacity to illuminate each sample with a beam of light of a specified wavelength and detect the fluorescence emitted by the excited fluorophore. The thermal cycler is also able to rapidly heat and chill samples, thereby taking advantage of the physicochemical properties of the nucleic acids and thermal polymerase. In order to detect and measure the amount of amplicon (i.e., amplified target nucleic acid sequence) in the sample, a measurable signal has to be generated, which is proportional to the amount of amplified product. All current detection systems use fluorescent technologies. Some of them are non-specific techniques, and consequently only allow the detection of one target at a time.

Alternatively, specific detection chemistries can distinguish between non-specific amplification and target amplification. These specific techniques can be used to multiplex the assay, i.e., detecting several different targets in the same assay. For example, SYBR® Green I probes, High Resolution Melting probes, TaqMan® probes, LNA® probes and Molecular Beacon probes can be suitable. TaqMan® probes are the most widely used type of probes. They were developed by Roche (Basel, Switzerland) and ABI (Foster City, USA) from an assay that originally used a radio-labelled probe (Holland et al., 1991. *Proc Natl Acad Sci USA*. 88(16):7276-80), which consisted of a single-stranded probe sequence that was complementary to one of the strands of the amplicon. A fluorophore is attached to the 5' end of the probe and a quencher to the 3' end. The fluorophore is excited by the machine and passes its energy, via FRET (Fluorescence Resonance Energy Transfer) to the quencher. Traditionally, the FRET pair has been conjugated to FAM as the fluorophore and TAMRA as the quencher. In a well-designed probe, FAM does not fluoresce as it passes its energy onto TAMRA. As TAMRA fluorescence is detected at a different wavelength to FAM, the background level of FAM is low. The probe binds to the amplicon during each annealing step of the PCR. When the Taq polymerase extends from the primer which is bound to the amplicon, it displaces the 5' end of the probe, which is then degraded by the 5'-3' exonuclease activity of the Taq polymerase. Cleavage continues until the remaining probe melts off the amplicon. This process releases the fluorophore and quencher into solution, spatially separating them (compared to when they were held together by the probe). This leads to an irreversible increase in fluorescence from the FAM and a decrease in the TAMRA.

In some embodiments, the expression level of the stroke biomarkers at the nucleic acid level (i.e., RNA) is determined by RNA-seq. As used, the term "RNA-seq" or "transcriptome sequencing" refers to sequencing performed on RNA (or cDNA) instead of DNA, where typically, the primary goal is to measure expression levels, detect fusion transcripts, alternative splicing, and other genomic alterations that can be better assessed from RNA. RNA-seq typically includes whole transcriptome sequencing. As used herein, the term "whole transcriptome sequencing" refers to the use of high throughput sequencing technologies to sequence the entire transcriptome in order to get information about a sample's RNA content. Whole transcriptome sequencing can be done with a variety of platforms for example, the Genome Analyzer (Illumina, Inc., San Diego, Calif.) and the SOLiD™ Sequencing System (Life Technologies, Carlsbad, Calif.), However, any platform useful for whole transcriptome sequencing may be used. Typically, the RNA is extracted, and ribosomal RNA may be deleted as described in U.S. Pat. No. 9,005,891. cDNA sequencing libraries may be prepared, that are directional and single or paired-end using commercially available kits such as the ScriptSeg™ M mRNA-Seq Library Preparation Kit (Epicenter Biotechnologies, Madison, Wis.). The libraries may also be barcoded for multiplex sequencing using commercially available barcode primers such as the RNA-Seq Barcode Primers from Epicenter Biotechnologies (Madison, Wis.). PCR is then carried out to generate the second strand of cDNA to incorporate the barcodes and to amplify the libraries. After the libraries are quantified, the sequencing libraries may be sequenced. Nucleic acid sequencing technologies are suitable methods for expression analysis. The principle underlying these methods is that the number of times a DNA sequence is detected in a sample is directly related to the relative RNA levels corresponding to that sequence. These methods are sometimes referred to by the term "Digital Gene Expression" or DOE, to reflect the discrete numeric property of the resulting data. Early methods applying this principle were Serial Analysis of Gene Expression (SAGE) and Massively Parallel Signature Sequencing (MPSS). See, e.g., Brenner et al. (2000. *Nat Biotechnol.* 18(6):630-634). Typically, RNA-seq uses Next Generation Sequencing (or NGS). As used herein, the term "Next Generation Sequencing" or "NGS" refers to a relatively new sequencing technique as compared to the traditional Sanger sequencing technique. For a review, see Shendure et al. (2008. *Nat Biotechol.* 26(10):1135-45), which is hereby incorporated by reference into this disclosure. For the purpose of this disclosure, NGS may include cyclic array sequencing, microelectrophoretic sequencing, sequencing by hybridization, among others. By way of example, in a typical NGS using cyclic-array methods, genomic DNA or cDNA library is first prepared, and common adaptors may then be ligated to the fragmented genomic DNA or cDNA. Different protocols may be used to generate jumping libraries of mate-paired tags with controllable distance distribution. An array of millions of spatially immobilized PCR colonies or "polonies" is generated with each polonies consisting of many copies of a single shotgun library fragment. Because the polonies are tethered to a planar array, a single microliter-scale reagent volume can be applied to manipulate the array features in parallel, e.g., for primer hybridization or for enzymatic extension reactions. Imaging-based detection of fluorescent labels incorporated with each extension may be used to acquire sequencing data on all features in parallel. Successive iterations of enzymatic interrogation and imaging may also be used to build up a contiguous sequencing read for each array feature.

In one embodiment, the decision as to whether the expression level of a certain stroke biomarker in a specific sample, preferably a bodily fluid sample, more preferably a blood sample, is upregulated is taken in comparison to a reference signature and/or a predetermined reference value.

In one embodiment, a reference signature comprises or consists of predetermined reference values for each of the stroke biomarkers of interest, preferably of at least 1, 2, 3, 4, 5, 6, 7, 8, 9 or more stroke biomarkers selected from the group comprising or consisting of HSPA1B, NPAS4, DNAJB1, ATF3, HSPB1, RRAD, NR4A1, CYR61, C-FOS, GADD45G, RGS1, ARC, EGR4, PTGS2, RGS2, CCL3, BAG3, EGR2, HSPA4L, ADM, TM4SF1, EGR1, DUSP1, BTG2, LOC715456, HMOX1, LDLR, DNAJA4, MCL1, HSPA6, GADD45B, IL6, ADFP, HES4, DUSP5, GEM and G0S2, preferably selected from the group comprising or consisting of PTGS2, HMOX1, LDLR, HSPA1B, G0S2, BAG3, TM4SF1, DUSP1 and ADM, preferably with the proviso that the at least one or two stroke biomarkers do not consist in DUSP1 and/or ADM.

Typically, a reference signature may be either implemented in the software or an overall median or other arithmetic mean across measurements may be built.

In one embodiment, the reference signature is derived from a previous measurement of the expression levels of stroke biomarkers according to the invention, in a reference sample derived from the same subject, such as, for example, the expression levels of stroke biomarkers measured one month before the subsequent measurement of the expression levels of stroke biomarkers according to the invention, preferably six months before, more preferably one year before or more; or such as, for example, the expression levels of stroke biomarkers measured before starting a therapy.

In one embodiment, the reference signature is derived from the measurement of the expression levels of stroke biomarkers according to the invention, in a reference population.

In one embodiment, the reference signature can be relative to a signature derived from population studies, including without limitation, such subjects having similar age range, subjects in the same or similar ethnic group, similar cancer history and the like.

In one embodiment, the reference signature is derived from the measurement of the expression levels of stroke biomarkers according to the invention, in a control sample derived from one or more substantially healthy subject(s). As used herein, a "substantially healthy subject" has not been previously diagnosed or identified as having or suffering from a stroke.

In one embodiment, the reference population comprises substantially healthy subjects, preferably at least 50, more preferably at least 100, more preferably at least 200 and even more preferably at least 500 substantially healthy subjects.

By implying a multitude of samples from the reference population, it is conceivable to calculate a median and/or mean expression level for each stroke biomarker respectively. In relation to these results, a stroke biomarker can be monitored as differential expressed. In one embodiment, the reference signature corresponds to the mean expression levels of the stroke biomarkers of the signature of the invention, measured in the reference population. In one embodiment, the reference signature corresponds to the median expression levels of the stroke biomarkers of the signature of the invention, measured in the reference population.

In one embodiment, the reference signature is constructed using algorithms and other methods of statistical and structural classification. Samples from the reference population are used to compute a mean profile (i.e., a reference signature) of the at least one stroke biomarker, preferably at least 2, 3, 4, 5, 6, 7, 8 or 9 stroke biomarkers according to the invention.

In one embodiment, a stroke biomarker is considered as differentially expressed between a subject to be diagnosed as being affected or not with a stroke and a substantially healthy subject if the expression fold change is at least greater than about |1.1|, preferably at least greater than about |1.2|, about |1.3|, about |1.4|, about |1.5|, about |1.6|, about |1.7|, about |1.8|, about |1.9|, about |2.0|, about |2.1|, about |2.2|, about |2.3|, about |2.4|, about |2.5|, about |3.0|, about |4.0|, about |5.0| or more.

In one embodiment, a stroke biomarker is considered as differentially expressed between a subject to be diagnosed as being affected or not with a stroke and a substantially healthy subject if the expression fold change is at least greater than about 1.1, preferably at least greater than about 1.2, about 1.3, about 1.4, about 1.5, about 1.6, about 1.7, about 1.8, about 1.9, about 2.0, about 2.1, about 2.2, about 2.3, about 2.4, about 2.5, about 3.0, about 4.0, about 5.0 or more.

In one embodiment, a stroke biomarker is considered as differentially expressed between a subject to be diagnosed as being affected or not with a stroke and a substantially healthy subject if the $\log_2$ expression fold change is at least greater than about |0.1|, preferably at least greater than about |0.2|, about |0.3|, about |0.4|, about |0.5|, about |0.6|, about |0.7|, about |0.8|, about |0.9|, about |1.0|, about |1.1|, about |1.2|, about |1.3|, about |1.4|, about |1.5|, about |1.6|, about |1.7|, about |1.8|, about |1.9|, about |2.0|, about |2.1|, about |2.2|, about |2.3| or more.

In one embodiment, a stroke biomarker is considered as differentially expressed between a subject to be diagnosed as being affected or not with a stroke and a substantially healthy subject if the $\log_2$ expression fold change is at least greater than about 0.1, preferably at least greater than about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3 or more.

In one embodiment, a stroke biomarker is considered as differentially expressed between a subject to be diagnosed as being affected or not with a stroke and a substantially healthy subject if the expression level of said biomarker is at least about 0.5, about 1, about 1.5, about 2, about 2.5, about 3, about 3.5, about 4, about 5, about 6, about 7, about 8, about 9, about 10, about 15, about 20, about 30, about 40, about 50, or about 100 times higher than the expression level of the same biomarker determined in the substantially healthy subject, preferably in the reference population.

In one embodiment, when the expression level of more than one stroke biomarker is determined in a sample, preferably a bodily fluid sample, more preferably a blood sample, obtained from the subject to be diagnosed as being affected or not with a stroke, a score, which is a composite score of said expression levels, may be calculated and compared with a predetermined reference value. In one embodiment, a score higher than the predetermined reference value indicates that the subject has or has had a stroke.

Typically, the predetermined reference value is a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. For example, retrospective measurement in properly banked historical subject samples may be used in establishing the predetermined reference value. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after determining the expression level of the biomarker of the invention in a reference population, one can use algorithmic analysis for the statistic treatment of the expression levels determined in samples to be tested, and thus obtain a classification standard having significance for sample classification. The full name of ROC curve is receiver operator characteristic curve, which is also known as receiver operation characteristic curve. It is mainly used for clinical biochemical diagnostic tests. ROC curve is a comprehensive indicator that reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When 0.5<AUC<0.7, the accuracy is low. When 0.7<AUC<0.9, the accuracy is moderate. When AUC<0.9, the accuracy is high. This algorithmic method is preferably done with a computer. Existing software or systems in the art may be used for the drawing of the ROC curve, such as: MedCalc 9.2.0.1 medical statistical software, SPSS 9.0, ROCPOWER.SAS, DESIGNROC.FOR, MULTIREADER POWER.SAS, CREATE-ROC.SAS, GB STAT VI0.0 (Dynamic Microsystems, Inc. Silver Spring, Md., USA), etc.

The present invention further relates to a method of diagnosing a stroke in a subject, using the signature of stroke of the invention.

In one embodiment, the method of diagnosing a stroke according to the present invention is particularly suitable for diagnosing an ischemic stroke, a mini-stroke (or transient ischemic attack, TIA) and/or a haemorrhagic stroke (in particular, haemorrhagic stroke caused by intracerebral haemorrhage).

In one embodiment, the method of diagnosing a stroke according to the present invention is particularly suitable for distinguishing a stroke from a stroke mimic, which can exhibit some or all of the same symptoms as a stroke, except that it is not a stroke and it is not a result of brain ischemia. Without wishing to be bound by a theory, because an elevated level of the biomarker is the result of stroke, a subject having a stroke mimic will not have an elevated level of the biomarker (in other words, because the signature of the invention is specific or indicative of a stroke, a subject having a stroke mimic will not exhibit the same signature).

Common stroke mimics include, but are not limited to, migraine, syncope, peripheral vestibular disturbance and BPPV (benign paroxysmal positional vertigo), seizure, functional manifestation/anxiety, transient global amnesia, Bell's palsy, peripheral nerve disease/dysfunction, postural hypotension, tumor, viral illness, cardiac arrhythmia, multiple sclerosis, drug related, hypoglycaemia, Parkinson's disease, retinal/ocular pathology, spinal pathology, trigeminal neuralgia, urinary tract infection, delirium, motor neuron disease, subarachnoid haemorrhage, subdural hematoma and the like (see Nadaraj an et al., 2014. *Pract Neurol.* 14(1): 23-31).

Accordingly, the method of diagnosing a stroke according to the present invention provides the advantage of allowing an early and accurate diagnosis of stroke, which can benefit a subject suspected of having stroke in at least the following related aspects:

(1) it can reduce the rate of misdiagnosis of stroke; and/or
(2) it can limit the extent of tissue death by permitting early and proper treatment in a subject in need of treatment.

In one embodiment, the method of diagnosing a stroke according to the present invention comprises a step of providing a sample from the subject to be diagnosed as being affected or not with a stroke.

The term "sample", as used herein, generally refers to any sample which may be tested for expression levels of a biomarker, preferably of stroke markers according to the present invention.

In one embodiment, the sample is a bodily fluid sample. Examples of bodily fluids include, but are not limited to, blood, plasma, serum, lymph, ascetic fluid, cystic fluid, urine, bile, mucus, serous fluid, sebum, nipple exudate, synovial fluid, bronchoalveolar lavage fluid, sputum, amniotic fluid, peritoneal fluid, cerebrospinal fluid, pleural fluid, pericardial fluid, semen, saliva, tears, rheum, sweat and alveolar macrophages.

In one embodiment, the sample is a blood sample. The term "blood sample", as used herein, encompasses whole blood samples, serum samples and plasma samples.

In one embodiment, the sample is a whole blood, plasma or serum sample.

In one embodiment, the sample is not a body tissue sample. Examples of body tissues include, but are not limited to, brain, muscle, nerve, heart, lung, liver, pancreas, spleen, thymus, oesophagus, stomach, intestine, kidney, prostate, testis, ovary, hair, skin, bone, breast, uterus, bladder and spinal cord.

In one embodiment, the sample is not a brain tissue sample. Therefore, according to this embodiment, the methods of the invention do not comprise a step of providing a brain tissue sample from the subject.

In one embodiment, the sample is not a biopsy sample. In one embodiment, the sample is not a brain biopsy sample.

In one embodiment, the sample, preferably the bodily fluid sample, more preferably the blood sample, was previously taken from the subject, i.e., the method of diagnosing a stroke according to the present invention does not comprise a step of actively taking a sample from the subject. Consequently, according to this embodiment, the method of the invention is a non-invasive method, i.e., an in vitro method.

In one embodiment, the method of diagnosing a stroke according to the present invention comprises a step of determining the signature according to the present invention, in said sample, preferably bodily fluid sample, more preferably blood sample, from the subject.

Means and methods for determining the signature according to the present invention are detailed hereinabove.

In one embodiment, the step of determining the signature comprises a substep of measuring the expression level of at least one stroke biomarker, preferably at least 2, 3, 4, 5, 6, 7, 8 or 9 stroke biomarkers according to the present invention.

In one embodiment, the expression level of the at least one stroke biomarker, preferably at least 2, 3, 4, 5, 6, 7, 8 or 9 stroke biomarkers, is measured using a DNA microarray, so that the expression levels of each of the stroke biomarkers of the signature of the invention are simultaneously measured.

In one embodiment, the expression level of the at least one stroke biomarker, preferably at least 2, 3, 4, 5, 6, 7, 8 or 9 stroke biomarkers, is measured using RNAseq.

In one embodiment, the expression level of the at least one stroke biomarker, preferably at least 2, 3, 4, 5, 6, 7, 8 or 9 stroke biomarkers, is measured using a CodeSet. Custom CodeSets for a given panel of markers (e.g., for the stroke biomarkers disclosed herein) are commercially designable. These include, without limitation, nCounter® Custom CodeSets (NanoString) (Malkov et al., 2009. *BMC Res Notes.* 2:80; Kulkarni, 2011. *Curr Protoc Mol Biol.* Chapter 25: Unit25B.10).

In one embodiment, when the expression level of more than one stroke biomarker is determined in said sample, preferably bodily fluid sample, more preferably blood sample, from the subject to be diagnosed as being affected or not with a stroke, a composite score of said expression levels is calculated.

In one embodiment, the method of diagnosing a stroke according to the present invention comprises a step of comparing the signature determined from the sample, preferably the bodily fluid sample, more preferably the blood sample, of the subject, with a reference signature, as defined hereinabove.

In one embodiment, the method of diagnosing a stroke according to the present invention comprises a step of comparing the signature determined from the sample, preferably the bodily fluid sample, more preferably the blood sample, of the subject, with a predetermined reference value, as defined hereinabove.

In one embodiment, the method of diagnosing a stroke according to the present invention comprises a step of comparing the expression levels of the stroke biomarkers in the signature determined from the sample, preferably the bodily fluid sample, more preferably the blood sample, of the subject, with the expression levels of the stroke biomarkers in a reference signature, as defined hereinabove.

In one embodiment, the method of diagnosing a stroke according to the present invention comprises a step of diagnosing a stroke in the subject based on the correlation of the signature in a sample, preferably a bodily fluid sample, more preferably a blood sample, from said subject compared with the reference signature.

In one embodiment, the subject is diagnosed with a stroke when the signature determined from the sample, preferably the bodily fluid sample, more preferably the blood sample, of the subject is considered different to the reference signature, as defined hereinabove.

In one embodiment, the signature determined from the sample, preferably the bodily fluid sample, more preferably the blood sample, of the subject is considered different to the reference signature if the expression fold change of at least 1, preferably at least 2, 3, 4, 5, 6, 7, 8 or 9 stroke biomarkers as defined herein is at least greater than about |1.1|, preferably at least greater than about |1.2|, about |1.3|, about |1.4|, about |1.5|, about |1.6|, about |1.7|, about |1.8|, about |1.9|, about |2.0|, about |2.1|, about |2.2|, about |2.3|, about |2.4|, about |2.5|, about |3.0|, about |4.0|, about |5.0| or more.

In one embodiment, the signature determined from the sample, preferably the bodily fluid sample, more preferably the blood sample, of the subject is considered different to the reference signature if the expression fold change of at least 1, preferably at least 2, 3, 4, 5, 6, 7, 8 or 9 stroke biomarkers as defined herein is at least greater than about 1.1, preferably at least greater than about 1.2, about 1.3, about 1.4, about 1.5, about 1.6, about 1.7, about 1.8, about 1.9, about 2.0, about 2.1, about 2.2, about 2.3, about 2.4, about 2.5, about 3.0, about 4.0, about 5.0 or more.

In one embodiment, the signature determined from the sample, preferably the bodily fluid sample, more preferably the blood sample, of the subject is considered different to the reference signature if the $\log_2$ expression fold change of at least 1, preferably at least 2, 3, 4, 5, 6, 7, 8 or 9 stroke biomarkers as defined herein is at least greater than about |0.5|, preferably at least greater than about |0.1|, about |0.2|, about |0.3|, about |0.4|, about |0.5|, about |0.6|, about |0.7|, about |0.8|, about |0.9|, about |1.0|, about |1.1|, about |1.2|, about |1.3|, about |1.4|, about |1.5|, about |1.6|, about |1.7|, about |1.8|, about |1.9|, about |2.0|, about |2.1|, about |2.2|, about |2.3| or more.

In one embodiment, the signature determined from the sample, preferably the bodily fluid sample, more preferably the blood sample, of the subject is considered different to the reference signature if the $\log_2$ expression fold change of at least 1, preferably at least 2, 3, 4, 5, 6, 7, 8 or 9 stroke biomarkers as defined herein is at least greater than about 0.5, preferably at least greater than about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3 or more.

In one embodiment, the signature determined from the sample, preferably the bodily fluid sample, more preferably the blood sample, of the subject is considered different to the reference signature if the expression level of at least 1, preferably at least 2, 3, 4, 5, 6, 7, 8 or 9 stroke biomarkers as defined herein is at least about 0.5, about 1, about 1.5, about 2, about 2.5, about 3, about 3.5, about 4, about 5, about 6, about 7, about 8, about 9, about 10, about 15, about 20, about 30, about 40, about 50, or about 100 times higher than the expression level of the same biomarker determined in the substantially healthy subject, preferably in the reference population.

In one embodiment, the subject is diagnosed with a stroke when the expression level of at least one, preferably at least 2, 3, 4, 5, 6, 7, 8, or 9 stroke biomarkers according to the invention is higher than the expression level of the same stroke biomarker in a substantially healthy subject, preferably in a reference population.

In one embodiment, the subject is diagnosed with a stroke when the composite score calculated for the expression levels of more than one, preferably at least 2, 3, 4, 5, 6, 7, 8, or 9 stroke biomarkers according to the invention, is higher than the predetermined reference value, i.e., the composite score calculated for the expression levels of the same biomarkers in a substantially healthy subject, preferably in a reference population.

In one embodiment, the method of diagnosing a stroke according to the present invention comprises the steps of:
  i) providing a sample, preferably a bodily fluid sample, more preferably a blood sample, from a subject to be diagnosed as being affected or not with a stroke;
  ii) determining the signature of the present invention in said sample;
  iii) comparing the signature determined in step ii) with a reference signature; and
  iv) diagnosing the subject as being affected with a stroke based on the correlation of the signature with the reference signature, as detailed hereinabove.

In one embodiment, the method of diagnosing a stroke according to the present invention comprises the steps of:
  i) providing a sample, preferably a bodily fluid sample, more preferably a blood sample, from a subject to be diagnosed as being affected or not with a stroke;
  ii) determining the signature in said sample, preferably by measuring the expression level of at least 1, 2, 3, 4, 5, 6, 7, 8, 9 or more stroke biomarkers selected from the group comprising or consisting of HSPA1B, NPAS4, DNAJB1, ATF3, HSPB1, RRAD, NR4A1, CYR61, C-FOS, GADD45G, RGS1, ARC, EGR4, PTGS2, RGS2, CCL3, BAG3, EGR2, HSPA4L, ADM, TM4SF1, EGR1, DUSP1, BTG2, LOC715456, HMOX1, LDLR, DNAJA4, MCL1, HSPA6, GADD45B, IL6, ADFP, HES4, DUSP5, GEM and G0S2,
  preferably with the proviso that the at least one or two stroke biomarkers do not consist in DUSP1 and/or ADM;
  iii) comparing the signature determined in step ii) with a reference signature; and
  iv) diagnosing the subject as being affected with a stroke based on the correlation of the signature with the reference signature, as detailed hereinabove.

In one embodiment, the method of diagnosing a stroke according to the present invention comprises the steps of:
  i) providing a sample, preferably a bodily fluid sample, more preferably a blood sample, from a subject to be diagnosed as being affected or not with a stroke;
  ii) determining the signature in said sample, preferably by measuring the expression level of at least 1, 2, 3, 4, 5, 6, 7, 8 or 9 stroke biomarkers selected from the group comprising or consisting of PTGS2, HMOX1, LDLR, HSPA1B, G0S2, BAG3, TM4SF1, DUSP1 and ADM,
  preferably with the proviso that the at least one or two stroke biomarkers do not consist in DUSP1 and/or ADM;
  iii) comparing the signature determined in step ii) with a reference signature; and
  iv) diagnosing the subject as being affected with a stroke based on the correlation of the signature with the reference signature, as detailed hereinabove.

In one embodiment, the method of diagnosing a stroke according to the present invention comprises the steps of:

i) providing a sample, preferably a bodily fluid sample, more preferably a blood sample, from a subject to be diagnosed as being affected or not with a stroke;

ii) determining the signature in said sample, preferably by measuring the expression level of at least three stroke biomarkers selected from the group comprising or consisting of PTGS2, HMOX1, LDLR, HSPA1B, G0S2, BAG3, TM4SF1, DUSP1 and ADM;

iii) comparing the signature determined in step ii) with a reference signature; and iv) diagnosing the subject as being affected with a stroke based on the correlation of the signature with the reference signature, as detailed hereinabove.

In one embodiment, the method of diagnosing a stroke according to the present invention comprises the steps of:

i) providing a sample, preferably a bodily fluid sample, more preferably a blood sample, from a subject to be diagnosed as being affected or not with a stroke;

ii) determining the signature in said sample, preferably by measuring the expression level of PTGS2, HMOX1, LDLR, HSPA1B, G0S2, BAG3 and TM4SF1;

iii) comparing the signature determined in step ii) with a reference signature; and iv) diagnosing the subject as being affected with a stroke based on the correlation of the signature with the reference signature, as detailed hereinabove.

In one embodiment, the method of diagnosing a stroke according to the present invention comprises the steps of:

i) providing a sample, preferably a bodily fluid sample, more preferably a blood sample, from a subject to be diagnosed as being affected or not with a stroke;

ii) determining the signature in said sample, preferably by measuring the expression level of PTGS2, HMOX1, LDLR, HSPA1B, G0S2, BAG3, TM4SF1, DUSP1 and ADM;

iii) comparing the signature determined in step ii) with a reference signature; and iv) diagnosing the subject as being affected with a stroke based on the correlation of the signature with the reference signature, as detailed hereinabove.

In one embodiment, the method of diagnosing a stroke according to the present invention comprises the steps of i) determining the expression level of at least one level of biomarker selected from the group consisting of PTGS2, HMOX1, LDLR, HSPA1B, G0S2, BAG3, TM4SF1, DUSP1 and ADM in a sample, preferably a bodily fluid sample, more preferably a blood sample, obtained from the subject ii) comparing the level determined at step i) with its predetermined reference value and iii) diagnosing a stroke when the expression level determined at step is higher than the predetermined reference value.

In one embodiment, the reference signature is derived or obtained from a reference population, preferably a reference comprising at least one substantially healthy subject.

In one embodiment, the method of diagnosing a stroke according to the present invention is applied to a subject who presents symptoms of stroke without having undergone the routine screening to rule out all possible causes for stroke.

In one embodiment, the method of diagnosing a stroke according to the present invention can be part of the routine set of tests performed on a subject who presents symptoms of stroke, such as, without limitation, blindness in one eye, weakness in one arm or leg, weakness in one entire side of the body, dizziness, vertigo, double vision, weakness on both sides of the body, difficulty speaking, slurred speech, or loss of coordination.

In one embodiment, the method of diagnosing a stroke according to the present invention can be carried out in addition of other diagnostic tools that include in particular Computed Tomography (CT) and Magnetic Resonance Imaging (MRI).

The present invention further relates to a method of determining whether a subject suffering from stroke achieves a response with a therapy. The present invention further relates to a method of determining whether a subject suffering from stroke achieves a response during or after completion of a therapy.

In one embodiment, the method of determining whether a subject suffering from stroke achieves a response with a therapy comprises the steps of i) determining the expression level of at least one biomarker of the present invention selected from the group consisting of PTGS2, HMOX1, LDLR, HSPA1B, G0S2, BAG3, TM4SF1, DUSP1 and ADM, ii) comparing the expression level determined at step i) with a predetermined reference value and iii) concluding that the subject achieves a response when the level determined at step i) is lower than the predetermined reference value.

In one embodiment, the method of determining whether a subject suffering from stroke achieves a response with a therapy comprises steps of providing a sample, preferably a bodily fluid sample, more preferably a blood sample, from the subject, determining the signature of the present invention in said sample and comparing said signature with a reference signature. These steps have been detailed hereinabove in the frame of the method of diagnosing a stroke and apply mutatis mutandis to the present method.

In one embodiment, the method of determining whether a subject suffering from stroke achieves a response with a therapy comprises the steps of:

i) providing a sample, preferably a bodily fluid sample, more preferably a blood sample, from the subject;

ii) determining the signature of the present invention in said sample;

iii) comparing the signature determined in step ii) with a reference signature; and iv) concluding that the subject achieves a response based on the correlation of the signature with the reference signature, as detailed hereinabove.

In one embodiment, the method of determining whether a subject suffering from stroke achieves a response with a therapy comprises the steps of:

i) providing a sample, preferably a bodily fluid sample, more preferably a blood sample, from the subject;

ii) determining the signature in said sample, preferably by measuring the expression level of at least 1, 2, 3, 4, 5, 6, 7, 8, 9 or more stroke biomarkers selected from the group comprising or consisting of HSPA1B, NPAS4, DNAJB1, ATF3, HSPB1, RRAD, NR4A1, CYR61, C-FOS, GADD45G, RGS1, ARC, EGR4, PTGS2, RGS2, CCL3, BAG3, EGR2, HSPA4L, ADM, TM4SF1, EGR1, DUSP1, BTG2, LOC715456, HMOX1, LDLR, DNAJA4, MCL1, HSPA6, GADD45B, IL6, ADFP, HES4, DUSP5, GEM and G0S2;

preferably with the proviso that the at least one or two stroke biomarkers do not consist in DUSP1 and/or ADM;

iii) comparing the signature determined in step ii) with a reference signature; and iv) concluding that the subject achieves a response based on the correlation of the signature with the reference signature, as detailed hereinabove.

In one embodiment, the method of determining whether a subject suffering from stroke achieves a response with a therapy comprises the steps of:
i) providing a sample, preferably a bodily fluid sample, more preferably a blood sample, from the subject;
ii) determining the signature in said sample, preferably by measuring the expression level of at least 1, 2, 3, 4, 5, 6, 7, 8 or 9 stroke biomarkers selected from the group comprising or consisting of PTGS2, HMOX1, LDLR, HSPA1B, G0S2, BAG3, TM4SF1, DUSP1 and ADM; preferably with the proviso that the at least one or two stroke biomarkers do not consist in DUSP1 and/or ADM;
iii) comparing the signature determined in step ii) with a reference signature; and
iv) concluding that the subject achieves a response based on the correlation of the signature with the reference signature, as detailed hereinabove.

In one embodiment, the method of determining whether a subject suffering from stroke achieves a response with a therapy comprises the steps of:
i) providing a sample, preferably a bodily fluid sample, more preferably a blood sample, from the subject;
ii) determining the signature in said sample, preferably by measuring the expression level of at least three stroke biomarkers selected from the group comprising or consisting of PTGS2, HMOX1, LDLR, HSPA1B, G0S2, BAG3, TM4SF1, DUSP1 and ADM;
iii) comparing the signature determined in step ii) with a reference signature; and
iv) concluding that the subject achieves a response based on the correlation of the signature with the reference signature, as detailed hereinabove.

In one embodiment, the method of determining whether a subject suffering from stroke achieves a response with a therapy comprises the steps of:
i) providing a sample, preferably a bodily fluid sample, more preferably a blood sample, from the subject;
ii) determining the signature in said sample, preferably by measuring the expression level of PTGS2, HMOX1, LDLR, HSPA1B, G0S2, BAG3 and TM4SF1;
iii) comparing the signature determined in step ii) with a reference signature; and
iv) concluding that the subject achieves a response based on the correlation of the signature with the reference signature, as detailed hereinabove.

In one embodiment, the method of determining whether a subject suffering from stroke achieves a response with a therapy comprises the steps of:
i) providing a sample, preferably a bodily fluid sample, more preferably a blood sample, from the subject;
ii) determining the signature in said sample, preferably by measuring the expression level of PTGS2, HMOX1, LDLR, HSPA1B, G0S2, BAG3, TM4SF1, DUSP1 and ADM;
iii) comparing the signature determined in step ii) with a reference signature; and
iv) concluding that the subject achieves a response based on the correlation of the signature with the reference signature, as detailed hereinabove.

In one embodiment, the reference signature is derived or obtained from a previous measurement of expression levels of stroke biomarkers according to the invention, in a reference sample derived from the same subject, such as, for example, the expression levels of stroke biomarkers measured before the start of a therapy.

In one embodiment, it is concluded that the subject achieves a response when the signature determined from the sample, preferably the bodily fluid sample, more preferably the blood sample, of the subject is considered different to the reference signature, as defined hereinabove.

In one embodiment, the signature determined from the sample, preferably the bodily fluid sample, more preferably the blood sample, of the subject is considered different to the reference signature if the expression fold change of at least 1, preferably at least 2, 3, 4, 5, 6, 7, 8 or 9 stroke biomarkers as defined herein is at least lower than about |1.1|, preferably at least lower than about |1.2|, about |1.3|, about |1.4|, about |1.5|, about |1.6|, about |1.7|, about |1.8|, about |1.9|, about |2.0|, about |2.1|, about |2.2|, about |2.3|, about |2.4|, about |2.5|, about |3.0|, about |4.0|, about |5.0| or more.

In one embodiment, the signature determined from the sample, preferably the bodily fluid sample, more preferably the blood sample, of the subject is considered different to the reference signature if the expression fold change of at least 1, preferably at least 2, 3, 4, 5, 6, 7, 8 or 9 stroke biomarkers as defined herein is at least lower than about 1.1, preferably at least lower than about 1.2, about 1.3, about 1.4, about 1.5, about 1.6, about 1.7, about 1.8, about 1.9, about 2.0, about 2.1, about 2.2, about 2.3, about 2.4, about 2.5, about 3.0, about 4.0, about 5.0 or more.

In one embodiment, the signature determined from the sample, preferably the bodily fluid sample, more preferably the blood sample, of the subject is considered different to the reference signature if the $\log_2$ expression fold change of at least 1, preferably at least 2, 3, 4, 5, 6, 7, 8 or 9 stroke biomarkers as defined herein is at least lower than about |0.1|, preferably at least lower than about |0.2|, about |0.3|, about |0.4|, about |0.5|, about |0.6|, about |0.7|, about |0.8|, about |0.9|, about |1.0|, about |1.1|, about |1.2|, about |1.3|, about |1.4|, about |1.5|, about |1.6|, about |1.7|, about |1.8|, about |1.9|, about |2.0|, about |2.1|, about |2.2|, about |2.3| or more.

In one embodiment, the signature determined from the sample, preferably the bodily fluid sample, more preferably the blood sample, of the subject is considered different to the reference signature if the $\log_2$ expression fold change of at least 1, preferably at least 2, 3, 4, 5, 6, 7, 8 or 9 stroke biomarkers as defined herein is at least lower than about 0.1, preferably at least lower than about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3 or more.

In one embodiment, the signature determined from the sample, preferably the bodily fluid sample, more preferably the blood sample, of the subject is considered different to the reference signature if the expression level of at least 1, preferably at least 2, 3, 4, 5, 6, 7, 8 or 9 stroke biomarkers as defined herein is at least about 0.5, about 1, about 1.5, about 2, about 2.5, about 3, about 3.5, about 4, about 5, about 6, about 7, about 8, about 9, about 10, about 15, about 20, about 30, about 40, about 50, or about 100 times lower than the expression level of the same biomarker determined in the substantially healthy subject, preferably in the reference population.

In one embodiment, the signature determined from the sample, preferably the bodily fluid sample, more preferably the blood sample, of the subject is considered different to the reference signature if the expression level of at least one, preferably at least 2, 3, 4, 5, 6, 7, 8, or 9 stroke biomarkers according to the invention is not higher than the expression level of the same stroke biomarker in a substantially healthy subject, preferably in a reference population.

In one embodiment, the signature determined from the sample, preferably the bodily fluid sample, more preferably the blood sample, of the subject is considered different to the reference signature if the composite score calculated for the expression levels of more than one, preferably at least 2, 3, 4, 5, 6, 7, 8, or 9 stroke biomarkers according to the invention, is not higher than the predetermined reference value, i.e., the composite score calculated for the expression levels of the same biomarkers in a substantially healthy subject, preferably in a reference population.

The method of determining whether a subject suffering from stroke achieves a response with a therapy is thus particularly suitable for discriminating "responders" from "non-responders".

As used herein, the term "responder" refers to a subject or patient that will achieve a therapeutic response, i.e., a subject in whom stroke is reduced, alleviated or cured. According to the invention, the responders have an objective response and therefore the term does not encompass subjects or patients having a stabilized stroke such that the disease is not progressing after the therapy.

As used herein, the term "non-responder" (or refractory) includes subjects or patients for whom stroke does not show reduction or improvement after the therapy. According to the invention, the term "non-responder" also includes subjects or patients having a stabilized stroke.

Typically, the characterization of the subject as being a responder or non-responder can be performed by reference to a standard or a training set. The standard may be the profile of a subject who is known to be a responder or non-responder, or alternatively may be a numerical value. Such predetermined standards may be provided in any suitable form, such as a printed list or diagram, computer software program, or other media. In some embodiments, the predetermined value is the expression level determined before the therapy. When it is concluded that the patient is a non-responder, the physician could take the decision to stop the therapy to avoid any further adverse sides effects.

In one embodiment, for monitoring purposes, expression levels can be measured at multiple time points, for example, twice, 3 times, 4 times, 5 times, 6 times, 7 times, 8 times, 9 times, 10 times or more. In this manner, monitoring of expression levels over time following or during therapy can provide a measure of the success of treatment, as it is to be expected that expression levels will decrease faster in subjects with successful treatment relative to an untreated subject for which expressions levels may decrease, albeit more slowly.

Typically, the therapy consists in any method well known by the skilled artisan. Treatment options include, but are not limited to, endovascular procedures and surgery, such as thrombectomy.

As used, herein the term "thrombectomy" defines any surgical and/or mechanical removal or breakdown of a clot. Typically, three classes of mechanical thrombectomy devices are known: coil retrievers, aspiration devices, and stent retrievers. Other devices and methods, currently under development, are also included in the definition of thrombectomy used herein. Typically, a catheter is sent to the blood flow blockage site to remove the blood clot. Combination of thrombectomy and thrombolysis can be administered to the patient. Additionally, ischemic stroke can also be treated by administering a thrombolytic agent to dissolve the blood clot ("thrombolysis").

Antithrombotic agents are further divided into the following three subtypes: anticoagulants, antiplatelet drugs, and thrombolytic drugs.

Examples of anticoagulants include, but are not limited to, coumarins, heparin, warfarin, acenocoumarol, phenprocoumon, atromentin, phenindione, fondaparinux, idraparinux, direct factor Xa inhibitors, direct thrombin inhibitors, antithrombin protein therapeutics, batroxobin, and hementin.

Examples of antiplatelet drugs include, but are not limited to, irreversible cyclooxygenase inhibitors (e.g., aspirin or triflusal), adenosine diphosphate receptor inhibitors (e.g., clopidogrel, prasugrel, ticagrelor, or ticlopidine), phosphodiesterase inhibitors (e.g., cilostazol), glycoprotein IIB/IIIA inhibitors (e.g., abciximab, eptifibatide, or tirofiban), adenosine reuptake inhibitors (e.g., dipyridamole), and thromboxane inhibitors (e.g., thromboxane synthase inhibitors or thromboxane receptor antagonists).

Examples of thrombolytic drugs include, but are not limited to, tissue plasminogen activator t-PA (alteplase and others (desmoteplase, reteplase, tenecteplase, . . . ), anistreplase, streptokinase, and urokinase. t-PA can be optionally administered during the endovascular procedures.

In one embodiment, the therapy consists in administering a neuroprotective agent.

Examples of neuroprotective agents typically include, without limitation, anti-free radicals, anti-glutamate agents, and CDK inhibitors.

In some embodiments, the neuroprotective agent is a cyclin-dependent kinase (CDK) inhibitor. Known CDK inhibitors may be classified according to their ability to inhibit CDKs in general or according to their selectivity for a specific CDK. Flavopiridol, for example, acts as a "pan" CDK antagonist and is not particularly selective for a specific CDK (Dai & Grant, 2003. *Curr Opin Pharmacol.* 3(4):362-70). Purine-based CDK inhibitors, such as olomoucine, roscovitine, purvanolols and CGP74514A, are known to exhibit a greater selectivity for CDKs 1, 2 and 5, but show no inhibitory activity against CDKs 4 and 6 (Dai & Grant, 2003. *Curr Opin Pharmacol.* 3(4):362-70). Furthermore, it has been demonstrated that purine-based CDK inhibitors such as S-roscovitine can exert anti-apoptotic effects in the nervous system (O'Hare et al., 2002. *Pharmacol Ther.* 93(2-3): 135-43; Timsit & Menn, 2012. *Clin Pharmacol Ther.* 91(2):327-32; Gutierrez-Vargas et al., 2017. *J Cereb Blood Flow Metab.* 37(6):2208-2223) or prevent neuronal death in neurodegenerative diseases, such as Alzheimer's disease (Filgueira de Azevedo et al., 2002. *Biochem Biophys Res Commun.* 297(5):1154-8; Knockaert et al., 2002. *Trends Pharmacol Sci.* 23(9):417-25).

In some embodiments, the therapy consists in hypothermia (e.g., Kurisu & Yenari, 2018. *Neuropharmacology.* 134(Pt B): 302-309).

The present invention further relates to a method of determining whether a subject is at risk of having stroke comprising the steps of i) determining the expression level of at least one level of biomarker selected from the group consisting of PTGS2, HMOX1, LDLR, HSPA1B, G0S2, BAG3, TM4SF1, DUSP1 and ADM in a sample, preferably a bodily fluid sample, more preferably a blood sample, obtained from the subject ii) comparing the level determined at step i) with its predetermined reference value and iii) concluding that the subject is at risk of having stroke when the expression level determined at step is higher than the predetermined reference value.

In one embodiment, the method of determining whether a subject is at risk of having stroke comprises steps of providing a sample, preferably a bodily fluid sample, more preferably a blood sample, from the subject, determining the signature of the present invention in said sample and comparing said signature with a reference signature. These steps have been detailed hereinabove in the frame of the method of diagnosing a stroke and apply mutatis mutandis to the present method.

In one embodiment, the method of determining whether a subject is at risk of having stroke comprises the steps of:
i) providing a sample, preferably a bodily fluid sample, more preferably a blood sample, from the subject;
ii) determining the signature of the present invention in said sample;
iii) comparing the signature determined in step ii) with a reference signature; and
iv) concluding that the subject is at risk of having stroke based on the correlation of the signature with the reference signature, as detailed hereinabove.

In one embodiment, the method of determining whether a subject is at risk of having stroke comprises the steps of:
i) providing a sample, preferably a bodily fluid sample, more preferably a blood sample, from the subject;
ii) determining the signature in said sample, preferably by measuring the expression level of at least 1, 2, 3, 4, 5, 6, 7, 8, 9 or more stroke biomarkers selected from the group comprising or consisting of HSPA1B, NPAS4, DNAJB1, ATF3, HSPB1, RRAD, NR4A1, CYR61, C-FOS, GADD45G, RGS1, ARC, EGR4, PTGS2, RGS2, CCL3, BAG3, EGR2, HSPA4L, ADM, TM4SF1, EGR1, DUSP1, BTG2, LOC715456, HMOX1, LDLR, DNAJA4, MCL1, HSPA6, GADD45B, IL6, ADFP, HES4, DUSP5, GEM and G0S2;
preferably with the proviso that the at least one or two stroke biomarkers do not consist in DUSP1 and/or ADM;
iii) comparing the signature determined in step ii) with a reference signature; and
iv) concluding that the subject is at risk of having stroke based on the correlation of the signature with the reference signature, as detailed hereinabove.

In one embodiment, the method of determining whether a subject is at risk of having stroke comprises the steps of:
i) providing a sample, preferably a bodily fluid sample, more preferably a blood sample, from the subject;
ii) determining the signature in said sample, preferably by measuring the expression level of at least 1, 2, 3, 4, 5, 6, 7, 8 or 9 stroke biomarkers selected from the group comprising or consisting of PTGS2, HMOX1, LDLR, HSPA1B, G0S2, BAG3, TM4SF1, DUSP1 and ADM;
preferably with the proviso that the at least one or two stroke biomarkers do not consist in DUSP1 and/or ADM;
iii) comparing the signature determined in step ii) with a reference signature; and
iv) concluding that the subject is at risk of having stroke based on the correlation of the signature with the reference signature, as detailed hereinabove.

In one embodiment, the method of determining whether a subject is at risk of having stroke comprises the steps of:
i) providing a sample, preferably a bodily fluid sample, more preferably a blood sample, from the subject;
ii) determining the signature in said sample, preferably by measuring the expression level of at least three stroke biomarkers selected from the group comprising or consisting of PTGS2, HMOX1, LDLR, HSPA1B, G0S2, BAG3, TM4SF1, DUSP1 and ADM;
iii) comparing the signature determined in step ii) with a reference signature; and
iv) concluding that the subject is at risk of having stroke based on the correlation of the signature with the reference signature, as detailed hereinabove.

In one embodiment, the method of determining whether a subject is at risk of having stroke comprises the steps of:
i) providing a sample, preferably a bodily fluid sample, more preferably a blood sample, from the subject;
ii) determining the signature in said sample, preferably by measuring the expression level of PTGS2, HMOX1, LDLR, HSPA1B, G0S2, BAG3 and TM4SF1;
iii) comparing the signature determined in step ii) with a reference signature; and
iv) concluding that the subject is at risk of having stroke based on the correlation of the signature with the reference signature, as detailed hereinabove.

In one embodiment, the method of determining whether a subject is at risk of having stroke comprises the steps of:
i) providing a sample, preferably a bodily fluid sample, more preferably a blood sample, from the subject;
ii) determining the signature in said sample, preferably by measuring the expression level of PTGS2, HMOX1, LDLR, HSPA1B, G0S2, BAG3, TM4SF1, DUSP1 and ADM;
iii) comparing the signature determined in step ii) with a reference signature; and
iv) concluding that the subject is at risk of having stroke based on the correlation of the signature with the reference signature, as detailed hereinabove.

In one embodiment, the reference signature is derived or obtained from a reference population, preferably a reference comprising at least one substantially healthy subject.

In one embodiment, the subject suffers from or has suffered from or has been diagnosed with a cardiovascular disease (e.g., atherosclerosis, hypertension . . . ) that can lead to stroke.

In one embodiment, the subject has experienced a stroke and the method of the present invention of the present invention is particularly suitable for predicting a recurrent stroke.

The method of determining whether a subject is at risk of having stroke is thus particularly suitable for providing a prognosis and thus identifying subjects at risk and then take all therapeutic interventions for preventing stroke.

As used herein, the term "risk" relates to the probability that an event will occur over a specific time period and can mean a subject's "absolute risk" or "relative risk".

"Absolute risk" can be measured with reference to either actual observation post-measurement for the relevant time cohort, or with reference to index values developed from statistically valid historical cohorts that have been followed for the relevant time period.

"Relative risk" refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula $p/(1-p)$ where p is the probability of event and $(1-p)$ is the probability of no event) to no-conversion.

"Risk evaluation" or "evaluation of risk" in the context of the present invention encompasses making a prediction of the probability, odds, or likelihood that an event or disease state may occur, the rate of occurrence of the event or conversion from one disease state to another. Risk evaluation can also comprise prediction of future clinical parameters, traditional laboratory risk factor values, or other indices of relapse, either in absolute or relative terms in reference to a previously measured population.

The determining whether a subject is at risk of having stroke may be used to make continuous or categorical measurements of the risk of conversion, thus diagnosing and defining the risk spectrum of a category of subjects defined as being at risk of conversion. In the categorical scenario, the invention can be used to discriminate between normal and other subject cohorts at higher risk. In one embodiment, the present invention may be used so as to discriminate those at risk from normal.

The present invention further relates to a method of determining the prognosis of a subject suffering from stroke comprising i) determining the expression level of at least one level of biomarker selected from the group consisting of DUSP1, PTGS2, HMOX1, LDLR, HSPA1B, G0S2, BAG3, ADM, and TM4SF1 in a sample, preferably a bodily fluid sample, more preferably a blood sample, obtained from the subject ii) comparing the level determined at step i) with its predetermined reference value and iii) concluding that the patient has a good prognosis when the level determined at step i) is lower than the predetermined reference value or concluding that the patient has a poor prognosis when the level determined at step i) is higher than the predetermined reference value.

In one embodiment, the method of determining the prognosis of a subject suffering from stroke comprises steps of providing a sample, preferably a bodily fluid sample, more preferably a blood sample, from the subject, determining the signature of the present invention in said sample and comparing said signature with a reference signature. These steps have been detailed hereinabove in the frame of the method of diagnosing a stroke and apply mutatis mutandis to the present method.

In one embodiment, the method of determining the prognosis of a subject suffering from stroke comprises the steps of:
 i) providing a sample, preferably a bodily fluid sample, more preferably a blood sample, from the subject;
 ii) determining the signature of the present invention in said sample;
 iii) comparing the signature determined in step ii) with a reference signature; and
 iv) concluding that the subject the patient has a good prognosis based on the correlation of the signature with the reference signature, as detailed hereinabove.

In one embodiment, the method of determining the prognosis of a subject suffering from stroke comprises the steps of:
 i) providing a sample, preferably a bodily fluid sample, more preferably a blood sample, from the subject;
 ii) determining the signature in said sample, preferably by measuring the expression level of at least 1, 2, 3, 4, 5, 6, 7, 8, 9 or more stroke biomarkers selected from the group comprising or consisting of HSPA1B, NPAS4, DNAJB1, ATF3, HSPB1, RRAD, NR4A1, CYR61, C-FOS, GADD45G, RGS1, ARC, EGR4, PTGS2, RGS2, CCL3, BAG3, EGR2, HSPA4L, ADM, TM4SF1, EGR1, DUSP1, BTG2, LOC715456, HMOX1, LDLR, DNAJA4, MCL1, HSPA6, GADD45B, IL6, ADFP, HES4, DUSP5, GEM and G0S2;
  preferably with the proviso that the at least one or two stroke biomarkers do not consist in DUSP1 and/or ADM;
 iii) comparing the signature determined in step ii) with a reference signature; and
 iv) concluding that the subject the patient has a good prognosis based on the correlation of the signature with the reference signature, as detailed hereinabove.

In one embodiment, the method of determining the prognosis of a subject suffering from stroke comprises the steps of:
 i) providing a sample, preferably a bodily fluid sample, more preferably a blood sample, from the subject;
 ii) determining the signature in said sample, preferably by measuring the expression level of at least 1, 2, 3, 4, 5, 6, 7, 8 or 9 stroke biomarkers selected from the group comprising or consisting of PTGS2, HMOX1, LDLR, HSPA1B, G0S2, BAG3, TM4SF1, DUSP1 and ADM;
  preferably with the proviso that the at least one or two stroke biomarkers do not consist in DUSP1 and/or ADM;
 iii) comparing the signature determined in step ii) with a reference signature; and
 iv) concluding that the subject the patient has a good prognosis based on the correlation of the signature with the reference signature, as detailed hereinabove.

In one embodiment, the method of determining the prognosis of a subject suffering from stroke comprises the steps of:
 i) providing a sample, preferably a bodily fluid sample, more preferably a blood sample, from the subject;
 ii) determining the signature in said sample, preferably by measuring the expression level of at least three stroke biomarkers selected from the group comprising or consisting of PTGS2, HMOX1, LDLR, HSPA1B, G0S2, BAG3, TM4SF1, DUSP1 and ADM;
 iii) comparing the signature determined in step ii) with a reference signature; and
 iv) concluding that the subject the patient has a good prognosis based on the correlation of the signature with the reference signature, as detailed hereinabove.

In one embodiment, the method of determining the prognosis of a subject suffering from stroke comprises the steps of:
 i) providing a sample, preferably a bodily fluid sample, more preferably a blood sample, from the subject;
 ii) determining the signature in said sample, preferably by measuring the expression level of PTGS2, HMOX1, LDLR, HSPA1B, G0S2, BAG3 and TM4SF1;
 iii) comparing the signature determined in step ii) with a reference signature; and
 iv) concluding that the subject the patient has a good prognosis based on the correlation of the signature with the reference signature, as detailed hereinabove.

In one embodiment, the method of determining the prognosis of a subject suffering from stroke comprises the steps of:
 i) providing a sample, preferably a bodily fluid sample, more preferably a blood sample, from the subject;
 ii) determining the signature in said sample, preferably by measuring the expression level of PTGS2, HMOX1, LDLR, HSPA1B, G0S2, BAG3, TM4SF1, DUSP1 and ADM;
 iii) comparing the signature determined in step ii) with a reference signature; and
 iv) concluding that the subject the patient has a good prognosis based on the correlation of the signature with the reference signature, as detailed hereinabove.

In one embodiment, the reference signature is derived or obtained from a reference population, preferably a reference comprising at least one substantially healthy subject.

In one embodiment, the reference signature is derived or obtained from a previous measurement of expression levels of stroke biomarkers according to the invention, in a reference sample derived from the same subject, such as, for example, the expression levels of stroke biomarkers measured after a stroke, preferably no less than 6 hours, 12 hours, 18 hours, 24 hours, 36 hours, 48 hours, 60 hours, 72 hours, 84 hours or 96 hours after a stroke.

As used herein, the term "prognosis" refers to a prediction of the probable outcome of stroke, i.e., the course of stroke or survival time the patient.

The term "good prognosis", as used herein, refers to greater than average likelihood of survival for a patient suffering from stroke as compared to other members of the same gender suffering from the same condition.

The term "poor prognosis" as used herein, refers to a less than average likelihood of survival for a patient suffering from stroke as compared to other members of the same gender suffering from the same condition.

The present invention further relates to a method of treating a subject affected with a stroke.

In one embodiment, the method of treating a subject affected with a stroke comprises steps of providing a sample, preferably a bodily fluid sample, more preferably a blood sample, from the subject, determining the signature of the present invention in said sample and comparing said signature with a reference signature. These steps have been detailed hereinabove in the frame of the method of diagnosing a stroke and apply mutatis mutandis to the present method.

In one embodiment, the method of treating a subject affected with a stroke comprises the steps of:
 i) providing a sample, preferably a bodily fluid sample, more preferably a blood sample, from said subject;
 ii) determining the signature of the present invention in said sample;
 iii) comparing the signature determined in step ii) with a reference signature;
 iv) diagnosing the subject as being affected with a stroke based on the correlation of the signature with the reference signature, as detailed hereinabove; and
 v) treating the subject if said subject was diagnosed as being affected with a stroke in step iv).

In one embodiment, the method of treating a subject affected with a stroke comprises the steps of:
 i) providing a sample, preferably a bodily fluid sample, more preferably a blood sample, from said subject;
 ii) determining the signature in said sample, preferably by measuring the expression level of at least 1, 2, 3, 4, 5, 6, 7, 8, 9 or more stroke biomarkers selected from the group comprising or consisting of HSPA1B, NPAS4, DNAJB1, ATF3, HSPB1, RRAD, NR4A1, CYR61, C-FOS, GADD45G, RGS1, ARC, EGR4, PTGS2, RGS2, CCL3, BAG3, EGR2, HSPA4L, ADM, TM4SF1, EGR1, DUSP1, BTG2, LOC715456, HMOX1, LDLR, DNAJA4, MCL1, HSPA6, GADD45B, IL6, ADFP, HES4, DUSP5, GEM and G0S2;
  preferably with the proviso that the at least one or two stroke biomarkers do not consist in DUSP1 and/or ADM;
 iii) comparing the signature determined in step ii) with a reference signature;
 iv) diagnosing the subject as being affected with a stroke based on the correlation of the signature with the reference signature, as detailed hereinabove; and
 v) treating the subject if said subject was diagnosed as being affected with a stroke in step iv).

In one embodiment, the method of treating a subject affected with a stroke comprises the steps of:
 i) providing a sample, preferably a bodily fluid sample, more preferably a blood sample, from said subject;
 ii) determining the signature in said sample, preferably by measuring the expression level of at least 1, 2, 3, 4, 5, 6, 7, 8 or 9 stroke biomarkers selected from the group comprising or consisting of PTGS2, HMOX1, LDLR, HSPA1B, G0S2, BAG3, TM4SF1, DUSP1 and ADM;
  preferably with the proviso that the at least one or two stroke biomarkers do not consist in DUSP1 and/or ADM;
 iii) comparing the signature determined in step ii) with a reference signature;
 iv) diagnosing the subject as being affected with a stroke based on the correlation of the signature with the reference signature, as detailed hereinabove; and
 v) treating the subject if said subject was diagnosed as being affected with a stroke in step iv).

In one embodiment, the method of treating a subject affected with a stroke comprises the steps of:
 i) providing a sample, preferably a bodily fluid sample, more preferably a blood sample, from said subject;
 ii) determining the signature in said sample, preferably by measuring the expression level of at least three stroke biomarkers selected from the group comprising or consisting of PTGS2, HMOX1, LDLR, HSPA1B, G0S2, BAG3, TM4SF1, DUSP1 and ADM;
 iii) comparing the signature determined in step ii) with a reference signature;
 iv) diagnosing the subject as being affected with a stroke based on the correlation of the signature with the reference signature, as detailed hereinabove; and
 v) treating the subject if said subject was diagnosed as being affected with a stroke in step iv).

In one embodiment, the method of treating a subject affected with a stroke comprises the steps of:
 i) providing a sample, preferably a bodily fluid sample, more preferably a blood sample, from said subject;
 ii) determining the signature in said sample, preferably by measuring the expression level of PTGS2, HMOX1, LDLR, HSPA1B, G0S2, BAG3 and TM4SF1;
 iii) comparing the signature determined in step ii) with a reference signature;
 iv) diagnosing the subject as being affected with a stroke based on the correlation of the signature with the reference signature, as detailed hereinabove; and
 v) treating the subject if said subject was diagnosed as being affected with a stroke in step iv).

In one embodiment, the method of treating a subject affected with a stroke comprises the steps of:
 i) providing a sample, preferably a bodily fluid sample, more preferably a blood sample, from said subject;
 ii) determining the signature in said sample, preferably by measuring the expression level of PTGS2, HMOX1, LDLR, HSPA1B, G0S2, BAG3, TM4SF1, DUSP1 and ADM;
 iii) comparing the signature determined in step ii) with a reference signature;
 iv) diagnosing the subject as being affected with a stroke based on the correlation of the signature with the reference signature, as detailed hereinabove; and v) treating the subject if said subject was diagnosed as being affected with a stroke in step iv).

In one embodiment, the reference signature is derived or obtained from a reference population, preferably a reference comprising at least one substantially healthy subject.

Examples of suitable treatments and therapies for subjects diagnosed as being affected with a stroke are well known in the art, and have been detailed hereinabove.

The invention will be further illustrated by the following example and figures. However, this example should not be interpreted in any way as limiting the scope of the present invention.

EXAMPLES

Figure 1A:
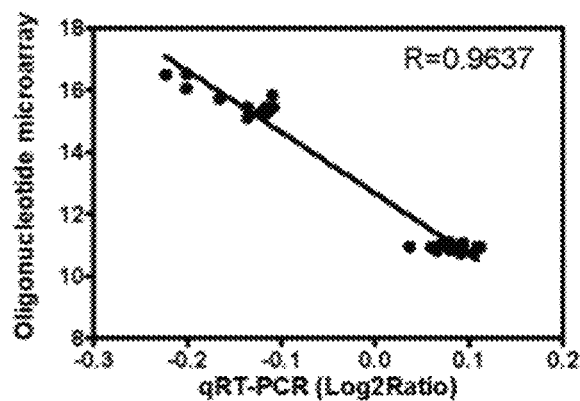
FIGS. 1A-1C are a set of 3 graphs showing the correlation between mRNA levels and microarray intensity values for (FIG. 1A) HSPA1B, (FIG. 1B) GADD45G and (FIG. 1C) CDKN1A by qRT-PCR. The x-axis shows the $\log_2$ ratio of qRT-PCR mRNA normalized for SMC2 and the y-axis shows the oligonucleotide microarray signal. P-value from Mann-Whitney U test.

The present invention is further illustrated by the following examples.

Example 1: Identification of a Common Signature Between the Ischemic Brain and the Blood in a Thrombotic Rhesus Macaque Model Methods
Animal Experiment Experiments were performed in 2 male rhesus macaques (*Macaca mulatta*) aged 12-13 years old, and with body weights ranging from 16.5 to 17.2 kg. In the following, these two monkeys will be noted S1 and S2.

An experimental protocol was submitted to the Regional Ethics Committee for Animal Experimentation (Normandy) and approval was granted to conduct the study (referral No. N/02-03-08/03/02-11). Experiments were performed by licensed investigators (C.O.) and in accordance with French and European ethical laws and guidelines for the care and use of laboratory animals (Directive 2010/63/EU of the European Parliament and of the Council of 22 Sep. 2010 on the protection of animals used for scientific purposes). During the course of the present studies, the monkeys were housed at the Cyceron Research Centre (Establishment for Animal Experimentation, agreement No. B14118001) in individual cages maintained at 24° C. with 50% relative humidity on a 12-hour/12-hour light/dark cycle and were fed with commercial chow supplemented with fresh fruits and water ad libitum. Throughout the duration of these studies, a veterinary surgeon was available to oversee the well-being of the animals.

Animal Model
Thrombotic Rhesus Macaque Model

Experiments were performed as previously described (Gauberti et al., 2012. *Cerebrovasc Dis.* 33(4):329-39).

Briefly, after general anaesthesia, following enucleation, the right middle cerebral artery (MCA) was exposed. Two sutures were positioned to isolate M1 branch into which the micropipette was inserted and human thrombin injected. About 600 μL of thrombin were injected at a concentration of 1 U/μL. A first injection of 100 μL was applied followed by 6 injection of 50 μL at 2 minutes of interval, and then the proximal suture was removed and the remaining thrombin was injected. The distal suture was then removed after 15 minutes.

The total procedure for thrombin injection took about 30 minutes.

Anaesthesia and Control of Physiologic Parameters

Animals were tranquilized with ketamine (0.1 mg/kg; IM; Imalgene®). Gaseous anaesthesia was induced by sevoflurane (2.5%; Sevorane®) in 100% oxygen. Muscular relaxation was obtained by atracurium (0.5 mg/kg; IV; Tracrium®) through a saphenous vein.

Monkeys were mechanically ventilated with positive intermittent pressure at a fixed respiratory frequency of 22 per minute. The tidal volume (VT) was adjusted to obtain a normocapnia ($Paco_2$=38-42 mmHg). Anaesthesia was maintained by sevoflurane with 66% of nitrous oxide.

During surgery, sevoflurane concentration was increased to 3% then decreased to 1.5-2% during magnetic resonance imaging (MRI) procedure. Intravenous atracurium perfusion was set at 0.75 mg/kg/h. The animals were positioned in a stereotactic frame before surgery.

In Vivo MRI Acquisition

Monkeys were studied in a 3T clinical MRI (Philips Sense Flex M).

Imaging was performed in the axial and coronal plane and included the following sequences: 3D-time-of-flight angiography, T2-weighted, fluid attenuation inversion recovery (FLAIR), diffusion-weighted imaging (DWI), and pre and post-contrast T1-weighted and perfusion-weighted imaging (PWI).

Blood Samples

Blood samples were obtained at $T_0$ before surgery but after general anaesthesia, and at $T_1$=+2 h, $T_2$=+3.5 h and $T_3$=+4.5 h after MCA occlusion.

For each blood sample, 2.5 mL were drawn for RNA. Blood samples were collected using PAXgenes Blood RNA tubes (PreAnalytix).

Brain Samples 12 brain samples were taken from each monkey. In each monkey, 6 samples were taken near the infarction site, and 6 samples were taken from the corresponding location in the other hemisphere. A total of 12 ischemic and 12 non-ischemic brain samples were thus analysed.

The two monkeys were operated and sacrificed about 5.5 hours after onset of occlusion (S1: 5 h12; S2: 5 h35). An MRI was performed between 3 and 4 hours after occlusion onset (S1: 3 h10; S2: 3 h05). Animals were infused by intra-cardiac injection after thoracotomy by about a total volume of 8 L of 4° C. saline serum. The brain was then removed after craniotomy and placed into a mold specifically designed for coronal brain slicing. Each cut of brain was further placed onto a grid to be able to identify x- and y-coordinates on the ischemic and contralateral hemisphere.

Arbitrarily on the grid, Roman numerals were for the right hemispheric ischemic side, and Arabic numerals for the left non-ischemic hemisphere side.

Ischemia was visible to the naked eye (data not shown) and confirmed by hypometabolic ischemic tissue treated by tetrazolium which appeared white as compared to the pinkish staining obtained in the non-ischemic contralateral hemisphere.

Three ischemic cortical samples per animal were prepared: one potentially corresponding to the core, and two from the edge, corresponding potentially to a penumbral region. Three homologous samples from the contralateral hemisphere per animal were also prepared.

TTC Staining

To evaluate metabolic activity and therefore ischemic tissue, brain samples adjacent tissue to be studied for transcriptomics were stained with 1% tetrazolium chloride (TTC).

Total RNA Extraction

Total RNA was isolated from cerebral cortex using the RNeasy Microarray Tissue kit following the manufacturer's instructions (Qiagen). RNA integrity was assessed with the Agilent 2100 BioAnalyzer (Agilent Technologies) by measuring the RIN (RNA integrity number) (Schroeder et al., 2006. BMC Mol Biol. 7:3). Measured RIN was between 6.3 and 8.8.

Total RNA was isolated from blood samples using the PAXgene Blood RNA Kit (PreAnalytix). Globin mRNA was removed from total RNA using the GlobinClear kit (Ambion). Measured RIN was between 7.8 and 10.

Macaca Expression Microarray and Choice of Samples

RNA from cerebral cortex (30 ng) and from blood sample (30 ng) were labelled using the Low Input Quick Amp WT Labeling kit (Agilent Technologies). RNA spike-in controls were used to adjust possible dye effects. RNA was converted to cDNA using reverse transcriptase and WT primers (T7 promoter primer and random primer with a T7 promoter). T7 RNA polymerase was used for the synthesis and labelling of cRNA with Cy3. The fluorescent-labelled cRNA probes were purified using the RNeasy mini kit (Qiagen).

An equal amount (3.75 µg) of Cy3 cRNA probes were hybridized on 4×44K Agilent DNA chip (catalogue number: G2519F, Macacca mulatta). Hybridization was performed for 17 hours, rotating at 10 rpm at 65° C. Then, samples were washed and dried according to the manufacturer's instructions.

Hybridization images were obtained using Agilent DNA microarray scanner and intensity data was extracted using Feature Extraction software (Agilent Technologies). This array contains 43803 rhesus macaque monkey probes. These probes are sourced from RefSeq (Release 37, October 2009), Unigene (Release 13, October 2009), UCSC MRNA (October 2009), Ensembl (Release 56, September 2009), UCSC RheMac2 (January 2006). Many probes are predicted based on orthologous human genes. Additionally, some probes are annotated only as Macaca mulatta cDNA, and other than what can be inferred from homology with human the functions are not known. Analysis was performed in collaboration with Genosplice (Evry, France), a company specialized in transcriptomic analysis.

Microarray analysis Differential expression analysis of the Agilent microarray expression data was performed using limma from the Bioconductor project (Smyth, 2004. Slat Appl Genet Mol Biol. 3:Article3). Raw data were normalized, first by performing background correction and then by normalizing between arrays for all brain and blood samples also using limma. Probes were annotated using Agilent's array information provided on Array Express (ebi.ac.uk/arrayexpress/arrays/A-GEOD-986 l/?page=71 & pagesize=100&sortby=organism&sortorder=descending) and gene information provided by Genosplice.

The limma package performs differential expression analysis by first fitting the expression data of each gene to a linear model. It then utilizes Empirical Bayes (eBayes) to borrow information across genes, which allows us to perform analysis across a small number of arrays.

All differential expression analyses of the brain microarray data were done using limma's eBayes method (Smyth, 2005. limma: Linear Models for Microarray Data. In: Gentleman et al. (Eds), Bioinformatics and Computational Biology Solutions Using R and Bioconductor. Statistics for Biology and Health. New York, N.Y.: Springer).

Statistics

Comparison of Highly Expressed Gene in the Brain

The two monkeys were analysed separately. Genes were labelled as "highly differentially expressed" if they had a fold change of more than 2 (i.e., a $log_2$ fold change greater than 1) in both monkeys when comparing ischemic and non-ischemic brain samples, and had a fold change of less than 2 when comparing ischemic samples between monkeys or when comparing non-ischemic samples between monkeys.

Comparison of Highly Expressed Gene in the Blood

Blood samples were analysed by comparing the pre-occlusion sample to each post-occlusion sample. The two monkeys were analysed separately. The time point with the largest fold change was selected for further analysis and called "S1 max blood" and "S2 max blood" (Table 1). Genes were labelled as "highly differentially expressed" if they had a fold change more than 1.5 in both monkeys when comparing the pre-occlusion sample to "51 max blood" and "S2 max blood".

Only highly differentially expressed genes in both ischemic brain and post-occlusion blood samples as defined above were compared and used to identify common highly differentially expressed genes.

Quality Control of Data

Internal Validation

A probe-specific two step TaqMan R Gene Expression Assay was used to validate microarray results (Applied Biosystems). Genes for validation were chosen based on ranking of differential expression and biological annotation relevant to ischemia. We chose SMC2 for normalization across target genes, for this gene showed a constant expression in ischemic and non-ischemic tissues samples. Gene Expression Assay probe IDs were as follows: HSPA1B (A 01 P010726), GADD45G (A 01 P018040), CDKN1A (A 01 P002585), SMC2 (A 01 P019124).

100 ng of total RNA of each sample was used to generate cDNA using the SuperScript® III First-Strand Synthesis Kit (ThermoFisher scientific) following the manufacturer's protocol. Real-time PCR reactions were carried out on the Roche LightCycler R480 System. Gene expressions were compared between ischemic and non-ischemic tissues using the comparative $C_T$ method ($\Delta\Delta C_T$ Method) with the Mann-Whitney U test (Wilcoxon), utilizing Prism software v6.0c (GraphPad, La Jolla, Calif.).

External Validation

We attempted to verify our results using data from a study by Cook et al. (2012. Nature. 483(7388):213-7). This study also examined stroke transcriptomics in gyrencephalic primate, however using cynomolgus macaques, a close relative of Macaca mulatta (Street et al., 2007. BMC Genomics. 8:480). In order to validate the results found in Macaca

*mulatta*, we analysed placebo and non-ischemic transcriptomic data from the Cook et al. study. The placebo ischemic and non-ischemic data was accessed from GEO (accession: GSE35589) and analysed using the methods described above.

Brain-Blood Gene Overlap

Significant overlap between brain and blood differential expression results was determined using the rank-rank hypergeometric overlap test (Plaisier et al., 2010. *Nucleic Acids Res.* 38(17):e169). This method performs a hypergeometric test on all possible overlaps of the sorted lists of genes in order to identify the cut-off at which the overlap between the two sets are most significant. The full gene lists were sorted by the average log fold change between the two monkeys. In order to examine specific genes whose expression changed in the brain and the blood, we produced a filtered list of highly differentially expressed genes in the brain (see methods above) and calculated the maximum fold change value for each of these genes in the blood.

Gene-Set Enrichment Analysis

Gene set enrichment analysis was performed using the GSEA command line tool (Subramanian et al., 2005. *Proc Natl Acad Sci USA.* 102(43):15545-50). This tool provides a predefined set of genes and determines whether each set is enriched near the top or bottom of the sorted experimental list, which is indicative of a phenotypic role. GSEA calculates an enrichment score (ES) for each gene set evaluated. This score indicates the degree to which the set is overrepresented at the top or bottom of the sorted experimental gene list. The normalized enrichment score (NES) is normalized by the size of the gene set.

Results from brain and blood differential expression analysis were sorted by log fold change. These lists were passed to GSEA pre-ranked function. The analysis was run using 100 permutations, and gene sets with fewer than 10 genes were excluded. The resulting gene sets were sorted by the NES. The GSEA ES indicates the degree to which a gene set is overrepresented at the top or bottom of the sorted gene list. The ES is calculated by moving down the list and increasing the score when a gene is present and decreasing when it is not. The magnitude by which the score is increased depends on the correlation of the gene with the phenotype (predefined gene set). The ES is the maximum deviation from 0 encountered when moving down the list. A positive ES indicates enrichment at the top of the list (in the upregulated genes), and a negative ES indicated enrichment at the bottom. The normalized ES accounts for differences in the size of the gene set and for correlations between gene sets and the expression data, allowing for comparisons between gene sets.

The interactions between genes in these gene sets were visualized using the STRING database (Szklarczyk et al., 2015. *Nucleic Acids Res.* 43(Database issue):D447-52). Genes were entered into STRING if they had a fold change of at least 2 in the brain, and 1.5 in the blood. The thickness of the lines indicates the confidence that a relationship exists and the large nodes indicate proteins for which there is information about the tertiary structure.

Results

Animals were sacrificed about 5.5 hours after ischemia onset. Axial MRI diffusion weighted image showed an MCA focal ischemia in both animals (data not shown). Analysis of the volume of ischemia in the two different animals showed that the volume of infarction was highly variable: S1 had a visibly larger infarction volume than S2. Superficial and deep infarctions were observed for animal S1 and S2. The infarction was also visible on T2 flair image in both animals. Willis Angio-MRI showed that MCA was proximally occluded for animal S1 while it was less clear for animal S2. Infarction was also visible on T1 sequence at the level of basal ganglia in animals S1 and S2.

Gene Expression Changes: Ischemic Versus Non-Ischemic Brain Tissue

In this study, changes in expression between ischemic and non-ischemic brain tissue was measured for individual genes, and the effect of these changes was examined at the level of gene sets. A differential expression analysis was performed comparing expression data from ischemic brain tissue to data from the corresponding region of the contralateral hemisphere, which did not undergo ischemia.

This analysis revealed that the expression patterns of ischemic and non-ischemic brain samples are visibly different (data not shown). Genes were considered highly differentially expressed if they had a fold change greater than 2 when comparing ischemic and non-ischemic brain samples within each monkey and these genes were not differentially expressed when comparing ischemic tissue between monkeys or non-ischemic tissue between monkeys (fold change <2). When hierarchical clustering was applied to these top differentially expressed genes (37 genes), the ischemic samples clearly cluster independently from the non-ischemic samples.

All of the highly differentially expressed genes were up-regulated (Table 1).

TABLE 1 the list of genes that were deemed highly differentially expressed in ischemic brain after extensive filtering.
The values show in columns "S1 brain" and "S2 brain" are the $\log_2$ fold change values of these genes in the brain of the two monkeys.
Columns "S1 max blood", "S1 timepoint", "S2 max blood" and "S2 timepoint" show data from the blood of the same two monkeys.
The time point with the maximum $\log_2$ fold change is shown for each.
Genes that are highly differentially expressed in the blood (fold change >|1.5|) appear in bold and greyed out.
HSPA1B and LOC720054 (HSPA1B) are replicate probes for different regions of the same gene.

| Gene symbol | S1 brain | S2 brain | S1 max blood | S1 time-point | S2 max blood | S2 time-point |
|---|---|---|---|---|---|---|
| HSPA1B | 4.67 | 5.40 | 1.86 | T0vs T3 | 0.99 | T0vs T1 |
| LOC720054 (HSPA1B) | 4.51 | 5.25 | 1.70 | $T_0$ vs $T_3$ | 0.53 | $T_0$ vs $T_1$ |
| NPAS4 | 3.57 | 2.65 | 0.05 | $T_0$ vs $T_2$ | 0.06 | $T_0$ vs $T_2$ |
| LOC718890 (DNAJB1) | 3.37 | 4.16 | 1.12 | $T_0$ vs $T_1$ | 0.22 | $T_0$ vs $T_1$ |
| ATF3 | 2.99 | 3.38 | 0.27 | $T_0$ vs $T_1$ | −0.04 | $T_0$ vs $T_1$ |
| HSPB1 | 2.85 | 3.30 | −0.63 | $T_0$ vs $T_2$ | −0.15 | $T_0$ vs $T_3$ |
| RRAD | 2.74 | 4.26 | 0.81 | $T_0$ vs $T_3$ | −0.03 | $T_0$ vs $T_1$ |
| NR4A1 | 2.72 | 2.88 | 0.03 | $T_0$ vs $T_1$ | −0.27 | $T_0$ vs $T_3$ |
| CYR61 | 2.61 | 2.34 | 0.11 | $T_0$ vs $T_2$ | 0.17 | $T_0$ vs $T_3$ |
| C-FOS | 2.53 | 3.77 | 0.17 | $T_0$ vs $T_2$ | 0.45 | $T_0$ vs $T_2$ |
| GADD45G | 2.25 | 2.04 | 0.44 | $T_0$ vs $T_3$ | 0.87 | $T_0$ vs $T_3$ |
| RGSI | 2.01 | 2.04 | 0.23 | $T_0$ vs $T_1$ | 0.57 | $T_0$ vs $T_2$ |
| LOC714407 (EGR4) | 1.84 | 1.76 | −0.19 | $T_0$ vs $T_2$ | 0.28 | $T_0$ vs $T_3$ |
| ARC | 1.84 | 1.90 | 0.27 | $T_0$ vs $T_3$ | 0.08 | $T_0$ vs $T_3$ |
| PTGS2 | 1.84 | 1.41 | 3.09 | T0vs T2 | 3.78 | T0vs T3 |
| RGS2 | 1.81 | 1.79 | 0.10 | $T_0$ vs $T_2$ | 0.81 | $T_0$ vs $T_2$ |
| CCL3 | 1.78 | 2.18 | −0.49 | $T_0$ vs $T_1$ | 0.00 | $T_0$ vs $T_3$ |
| BAG3 | 1.70 | 2.97 | 0.99 | T0vs T1 | 0.71 | T0vs T1 |
| HSPA4L | 1.68 | 1.64 | −0.13 | $T_0$ vs $T_1$ | 0.30 | $T_0$ vs $T_3$ |
| EGR2 | 1.68 | 2.09 | −0.12 | $T_0$ vs $T_2$ | −0.16 | $T_0$ vs $T_3$ |
| ADM | 1.66 | 2.59 | 2.60 | T0vs T3 | 0.86 | T0vs T3 |
| TM4SF1 | 1.61 | 2.42 | 0.65 | T0vs T3 | 1.01 | T0vs T3 |
| EGR1 | 1.56 | 2.10 | 0.22 | $T_0$ vs $T_1$ | 0.07 | $T_0$ vs $T_3$ |
| DUSP1 | 1.43 | 1.34 | 2.08 | T0vs T3 | 1.87 | T0vs T2 |
| BTG2 | 1.42 | 1.38 | 0.39 | $T_0$ vs $T_1$ | 0.14 | $T_0$ vs $T_2$ |
| LOC715456 | 1.36 | 1.14 | 1.33 | $T_0$ vs $T_1$ | 0.15 | $T_0$ vs $T_3$ |
| HMOX1 | 1.30 | 1.13 | 2.81 | T0vs T3 | 0.83 | T0vs T3 |

TABLE 1-continued the list of genes that were deemed highly differentially expressed in ischemic brain after extensive filtering.
The values show in columns "S1 brain" and "S2 brain" are the $\log_2$ fold change values of these genes in the brain of the two monkeys.
Columns "S1 max blood", "S1 timepoint", "S2 max blood" and "S2 timepoint" show data from the blood of the same two monkeys.
The time point with the maximum $\log_2$ fold change is shown for each.
Genes that are highly differentially expressed in the blood (fold change >|1.5|) appear in bold and greyed out.
HSPA1B and LOC720054 (HSPA1B) are replicate probes for different regions of the same gene.

| Gene symbol | S1 brain | S2 brain | S1 max blood | S1 timepoint | S2 max blood | S2 timepoint |
|---|---|---|---|---|---|---|
| highly similar to human LDLR [CN641580] | 1.29 | 1.12 | 2.60 | T0vs T1 | 1.56 | T0vs T1 |
| DNAJA4 | 1.28 | 1.65 | 0.56 | $T_0$ vs $T_3$ | −0.03 | $T_0$ vs $T_1$ |
| MCL1 | 1.24 | 1.52 | 0.56 | $T_0$ vs $T_3$ | 0.34 | $T_0$ vs $T_1$ |
| LOC720001 (HSPA6) | 1.20 | 1.07 | 0.31 | $T_0$ vs $T_1$ | 0.08 | $T_0$ vs $T_1$ |
| GADD45B | 1.08 | 2.17 | 0.46 | $T_0$ vs $T_2$ | 0.94 | $T_0$ vs $T_2$ |
| IL6 | 1.08 | 1.53 | −0.47 | $T_0$ vs $T_3$ | −0.10 | $T_0$ vs $T_2$ |
| ADFP | 1.08 | 1.25 | 0.61 | $T_0$ vs $T_1$ | 0.34 | $T_0$ vs $T_1$ |
| HES4 | 1.08 | 1.18 | −0.04 | $T_0$ vs $T_1$ | 0.13 | $T_0$ vs $T_1$ |
| DUSP 5 | 1.05 | 1.67 | −0.30 | $T_0$ vs $T_1$ | −0.78 | $T_0$ vs $T_1$ |
| GEM | 1.04 | 1.55 | 0.39 | $T_0$ vs $T_2$ | 0.19 | $T_0$ vs $T_1$ |
| LOC717581 (similar to G0S2) | 1.00 | 1.96 | 1.90 | T0vs T2 | 1.47 | T0vs T3 |

Internal Validation

Figure 1B:
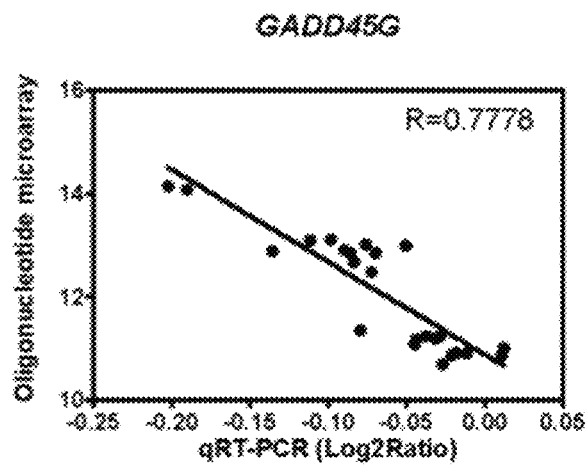
Figure 1C:
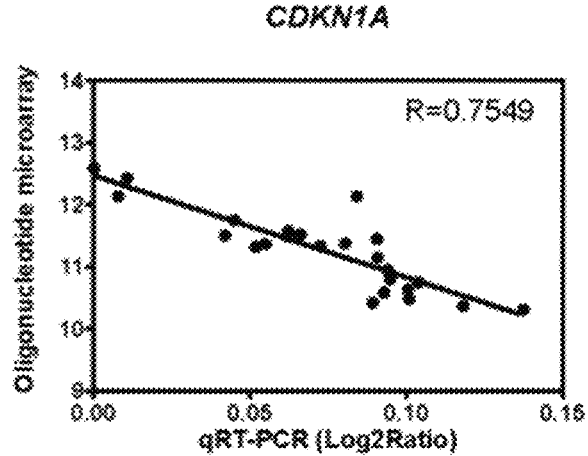

To confirm the robustness of the microarray results, mRNA levels of three ischemic-sensitive genes (HSPA1B, GADD45G, CDKN1A) were quantified by RT-qPCR using samples from the animals. SMC2, which was found to exhibit invariant expression level across all test samples, was used as internal reference (housekeeping). Three reverse transcriptions were performed for each RNA samples, followed by three independent qPCR runs, with replicate assay measurements for both target and reference genes. For all genes, the direction and magnitude of the change agreed well with the microarray data (FIGS. 1A-1C and Table 2).

TABLE 2 internal validation.

| | Microarray study | | qPCR validation | |
|---|---|---|---|---|
| Gene | Fold change | p-value | Fold change | p-value |
| HSPA1B | 32.78 | $3.80 \times 10^{-18}$ | 33.3 | *** |
| GADD45G | 4.41 | $9.40 \times 10^{-10}$ | 3.7 | ** |
| CDKNA1 | 2.05 | $1.49 \times 10^{-4}$ | 2.3 | ** |

Statistical significance: * $p < 0.05$;  $p < 0.01$; * $p < 0.001$. Results were normalized to SMC2.

External Validation

Analysis of transcriptome data from the Cook et al. study of stroke (2012. Nature. 483(7388):213-7) in Macaca fascicularis produced very different results than what has been described here. Whereas this analysis of Macaca mulatta revealed many up-regulated genes in the tissues affected by stroke, the data from Macaca fascicularis showed mainly down-regulated genes. This is mostly likely due to the very different method for inducing stroke in the primates. The study by Cook et al. used surgical middle cerebral artery occlusion (MCAO), which they acknowledged produces a more severe stroke than is usually observed in human. It is likely that this more severe stroke model caused massive cell death resulting in mainly down-regulated genes.

Gene Sets Enrichment

Gene sets that are enriched in ischemic brain tissue were identified using the Broad Institutes Gene Set Enrichment Analysis (GSEA) (Subramanian et al., 2005. Proc Natl Acad Sci USA. 102(43):15545-50). The top 5 enriched gene sets from GSEA's Hallmark gene sets were TNFA signalling via NFKB, apoptosis, P53 pathway, hypoxia, and UV response up, all of which were up-regulated (Table 3).

TABLE 3 the top 5 gene sets resulting from GSEA analysis differential expression results in the brain.

| Gene Set Name | Set size | Genes present (percentage) | NES |
|---|---|---|---|
| TNFA signalling via NFKB | 108 | 60 (55.56%) | 2.9935637 |
| Apoptosis | 98 | 26 (26.53%) | 2.5899184 |
| P53 pathway | 112 | 28 (25%) | 2.5179965 |
| Hypoxia | 118 | 33 (27.97%) | 2.455276 |
| UV response up | 96 | 31 (32.29%) | 2.3801901 |

60 out of the set of 108 genes had a core enrichment in the TNFA signalling via NFKB gene set (NES=2.96). Almost all genes in this set for which we have data are up-regulated, none are significantly down-regulated genes: 15 genes only are slightly down-regulated with a maximum fold change of 1.17.

In the apoptosis gene set, 26 out of 98 genes have core enrichment (NES=2.57).

In the hypoxia gene set, 33 out of 118 genes had core enrichment (NES=2.38).

The UV response up gene set had 31 out of 96 genes with core enrichment (NES=2.3).

The most significantly enriched down-regulated gene set was oxidative phosphorylation. 84 of these genes, out of 120, had core enrichment (NES=−2.57).

Interaction of Gene Products

The STRING database (Szklarczyk et al., 2015. Nucleic Acids Res. 43(Database issue):D447-52) was used in order to visualize the interaction of the gene products of genes that are highly differentially expressed in the brain and blood within the top gene sets of the brain (fold change ≥2 in the brain, fold change ≥1.5 in the blood) (data not shown).

It was noted that IL-6 is a highly connected member in the networks representing TNFA signalling via NFKB, apoptosis, and hypoxia. Additionally, CDKN1A appears in all four of these networks. The interaction of CDKN1A with HMOX1 is observed in the network of apoptosis-, p53 pathway-, and hypoxia-related genes. The gene ATF3 also appears in all four networks, and it interacts with IL-6 in the three mentioned above. The 5th ranking gene set in the brain (Table 3), UV response up, is not shown because none of the top differentially expressed genes in this set have any known interactions.

Gene Expression Changes: Pre-Occlusion Versus Post-Occlusion Blood Samples

Differentially expressed genes in the blood during cerebral ischemia were identified by comparing all pre-occlusion blood samples to all post-occlusion blood samples. When hierarchical clustering was applied to the top differentially expressed genes, pre-occlusion and post-occlusion samples cluster separately (data not shown). There also appears to be differing expression patterns in the blood of the two macaques based on this gene clustering. Monkey S1 has a more profound upregulation of these genes than monkey S2.

This separation of the two monkeys is not apparent in the expression patterns of the brain (data not shown).

As with the brain samples, gene set enrichment of the blood differential expression results was analysed. The top 5 enriched gene sets are TNFA signalling via NFKB, hypoxia, hedgehog signalling, inflammatory response, and angiogenesis (Table 4).

TABLE 4 the top 5 gene sets resulting from GSEA analysis differential expression results in the blood.

| Gene set name | Set size | Genes present (percentage) | NES |
|---|---|---|---|
| TNFA signalling via NFKB | 108 | 37 (34.36%) | 1.9190117 |
| Hypoxia | 118 | 42 (25.59%) | 1.9131837 |
| Hedgehog signalling | 24 | 10 (41.67%) | 1.779471 |
| Inflammatory response | 110 | 35 (31.82%) | 1.7678385 |
| Angiogenesis | 20 | 9 (45%) | 1.7562431 |

The TNFA signalling via NFKB and hypoxia gene sets also appeared in the top 5 gene sets for the brain (Table 4).

37 out of 108 genes in the TNFA signalling via NFKB gene set had core enrichment (NES=1.92).

42 out of 118 genes in the hypoxia gene set had core enrichment (NES=1.91).

10 out of 24 genes in the hedgehog signalling gene set had a core enrichment (NES=1.77).

35 out of 110 genes in the inflammatory response gene set had core enrichment (NES=1.77).

9 out of 20 genes in the angiogenesis gene set had core enrichment (NES=1.76).

Differentially Expressed Genes Common Between the Brain and the Blood

Figure 2:
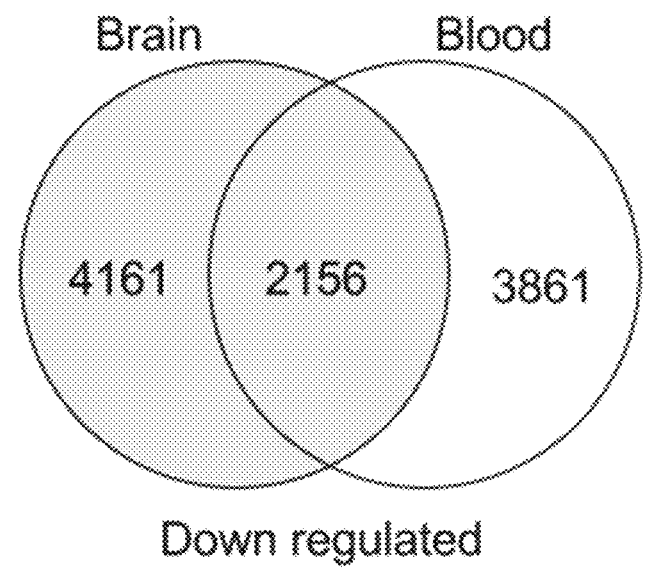
FIG. 2 is a set of two Venn diagrams of the most significant overlap between the two sets of genes differentially expressed in the brain and in the blood. Upper panel shows down-regulated genes; lower panel shows up-regulated genes.
Figure 2:
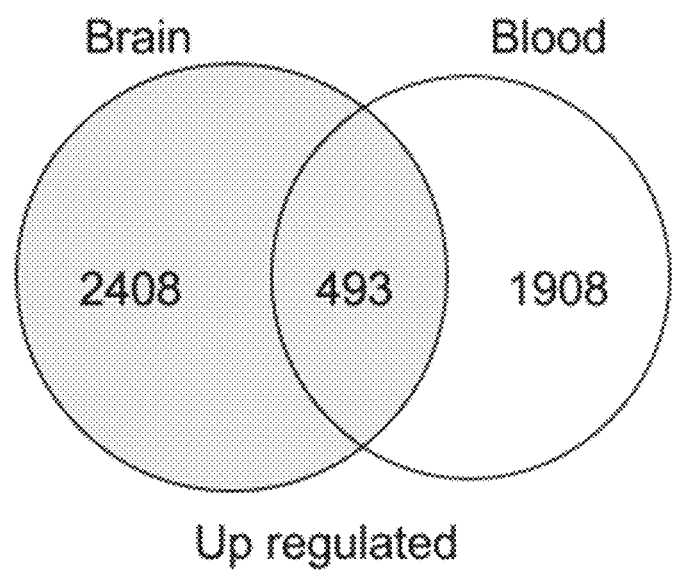

Differential expression results from the brain and blood were examined for significant overlap when genes were sorted by fold change. We show that the two sorted gene sets are highly similar, particularly at the two extremes: the most upregulated and most downregulated genes during ischemia. We also showed the overlapping genes from the heatmap that are most significant: 2156 down regulated genes significantly overlap between brain and blood samples, and 493 up-regulated genes significantly overlap (FIG. 2). The majority of these genes have a relatively low expression fold-change, however the overlap of differentially expressed genes is very high between brain and blood samples.

Figure 3:
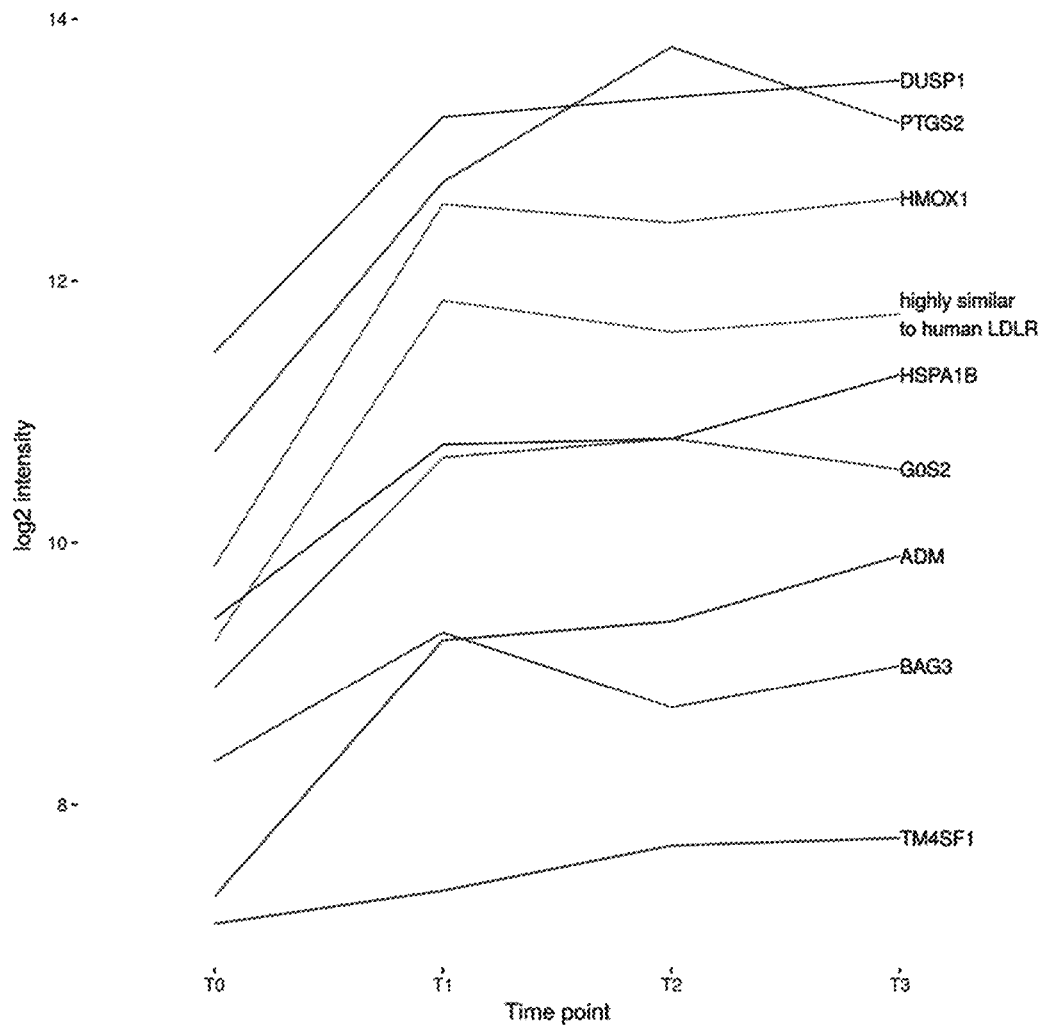
FIG. 3 illustrates the blood gene intensity kinetic in the blood for the 9 top differentially expressed genes in the male rhesus macaque S1 between different time points: before ($T_0$) and after ($T_1$, $T_2$, $T_3$) ischemia.
Figure 4:
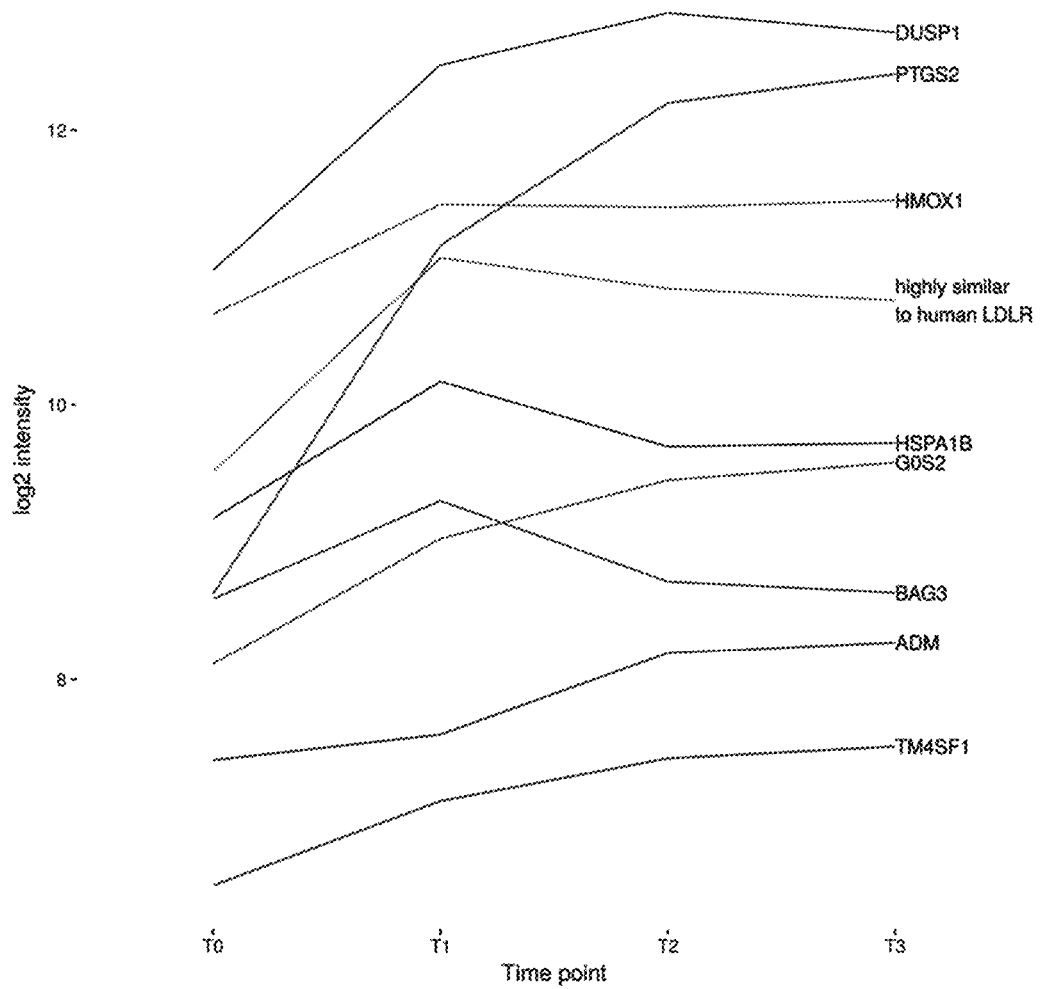
FIG. 4 illustrates the blood gene intensity kinetic in the blood for the 9 top differentially expressed genes in the male rhesus macaque S2 between different time points: before ($T_0$) and after ($T_1$, $T_2$, $T_3$) ischemia.

Although many genes in these overlapping sets were not highly differentially expressed, some were, and it is those with a very high change in expression in the brain that we were most interested in. Of the genes identified as highly differentially expressed in the brain, 9 were also differentially expressed in the blood (fold change ≥1.5; Table 1, highlighted in bold). All 9 of these genes occur within the most significant hypergeometric overlap (bolded). These genes are PTGS2, G0S2-like, DUSP1, LDLR-like, HMOX1, HSPA1B, BAG3, ADM, and TM4SF1. The majority of these genes have a sharp increase in expression in the blood, which levels off over time (FIGS. 3 and 4).

Discussion

A non-human primate model (Gauberti et al., 2012. Cerebrovasc Dis. 33(4):329-39) with human thrombin injection in the MCA artery was used to study patterns of gene expression changes during ischemic cerebral stroke. This is an embolic model of focal ischemia with a partial MCA ischemia. A time frame of 6 hours was used, because this is the window of time where therapeutic interventions are possible in human (thrombolysis up to 4 h30; thrombectomy up to 6 h after onset).

Our study of macaque microarray expression data from brain and blood revealed that ischemic and non-ischemic samples can be distinguished based on their expression profiles, and the majority of highly differentially expressed genes are up-regulated in the ischemic scenario 6 hours after ischemia. Many of these up-regulated genes belong to pathways involved in cell death and DNA damage repair. A comparison of genes differentially expressed in the brain and the blood revealed a significant overlap of gene expression patterns.

These results indicate the potential to identify ischemic stroke through transcriptomics in the brain and the blood.

Gene Expression in Ischemic Brain

Quality of the data was confirmed by PCA analysis showing that it was possible to differentiate both monkeys and ischemia from non-ischemia by gene expression. Furthermore, internal validation further supported generated results.

Hierarchical clustering of *Macaca mulatta* brain expression data revealed strong independent clustering of ischemic and non-ischemic brain samples (data not shown). These results indicated a potential for identifying ischemic brain tissue based on expression profiles. The most significantly differentially expressed genes were up-regulated, which is consistent with many previous studies of ischemia in mouse (Buttner et al., 2009. *Brain Res.* 1252:1-14; Hori et al., 2012. *Dis Model Mech.* 5(2):270-83). This study defined highly differentially expressed genes in the brain as genes that have a minimum fold change of 2 in both monkeys, and the genes are not differentially expressed when comparing non-ischemic samples between monkeys or when comparing ischemic samples between monkeys (fold change <2). The results of our analysis found that 37 genes were up-regulated and none were down-regulated in the brain. These results are similar to those of Buttner et al. which found 115 up-regulated and 19 down-regulated genes after 6 hours (Buttner et al., 2009. *Brain Res.* 1252:1-14). The larger number of genes identified by Buttner et al. can be explained by the larger expression profile array used and expression differences between species.

All highly differentially expressed genes in ischemic brain tissue were up-regulated. Many of these genes have been previously identified as up-regulated genes in ischemic stroke for a variety of functions, notably stress response, apoptosis, and signal transduction.

Among the up-regulated stress response genes were 7 heat shock proteins HSPA1B (Hsp70), HSP40, HSPB1, HSPA4L, and DNAJA4 (Hsp40-like) (Table 1). Numerous studies have identified heat shock proteins as highly up-regulated in ischemia (Schmidt-Kastner et al., 2002. *Brain Res Mol Brain Res.* 108(1-2): 81-93; Buttner et al., 2009. *Brain Res.* 1252:1-14; Kawahara et al., 2004. *J Cereb Blood Flow Metab.* 24(2):212-23; Tang et al., 2002. *Eur J Neurosci.* 15(12):1937-52). The human ortholog of this gene is well characterized as a stress-induced gene that stabilizes proteins against aggregation, and is involved in the ubiquitin-proteasome pathway (NCBI, Accession: NM_005346.5). Hsp70 is the most commonly reported up-regulated heat shock protein in ischemic stroke (Cox-Limpens et al., 2014. *Brain Res.* 1564:85-100). In *Macaca mulatta*, Heat Shock Protein Family A (Hsp70) Member 1B (HSPA1B) is the most up-regulated gene in ischemic brain tissue. Knockout studies of HSPA1B in mice showed that cardiac cells lacking this gene are more susceptible to damage by ischemia (Kim et al., 2006. *Circulation.* 113(22): 2589-97). Studies of cerebral ischemia showed hsp70 knockout mice experienced a greater infarction volume than wild type mice (Lee et al., 2004. *Stroke.* 35(9):2195-9), and mice that over-express Hsp70 exhibited a decreased infarct size and improved neurological function (Zheng et al., 2008. *J Cereb Blood Flow Metab.* 28(1):53-63). The high level of differential expression of HSPA1B in macaque indicates it may also be playing a neuro-protective role in primate brains undergoing ischemia. It is also interesting to note that one of the most differentially expressed gene from these microarrays is DNAJB1, a heat shock protein homologue.

NPAS4 is another highly differentially expressed stress response gene that is also known to be a neuroprotectant (Choy et al., 2015. *Int J Mol Sci.* 16(12):29011-28). This transcription factor is expressed in the neurons of the brain, and plays a role in early response in excitatory and inhibitory neurons. Its expression is induced by a variety of situations that put neuronal cells under stress. In our study, NPAS4 had a $\log_2$ fold change of 3.57 in 51 and 2.65 in S2 (Table 1). The gene C-FOS, which is controlled by NPAS4 (Ramamoorthi et al., 2011. *Science.* 334(6063):1669-75), is also highly differentially expressed in our study with a $\log_2$ fold change of 2.53 in 51 and 3.77 in S2. C-FOS is commonly found to be up-regulated in the presence of cerebral ischemia (Cox-Limpens et al., 2014. *Brain Res.* 1564:85-100).

The gene Activating Transcription Factor 3 (ATF3) is the next most differentially expressed gene. ATF3 encodes a member of the cAMP responsive element-binding (CREB) family of transcription factors. It is involved in cellular stress response. ATF3 underwent a $\log_2$ fold change of 2.99 in 51 and 3.38 in S2 (Table 1). Additionally, this gene is a highly connected member within the top GSEA gene sets (data not shown).

Previous experiments on mice found that ATF3 knockouts have a larger infarction volume and worsened neurological function after brain ischemia (Wang et al., 2012. *Neuroscience.* 220:100-8).

Other important stress response genes which were upregulated in ischemic brain tissue are two damage-inducible genes, GADD45G and GADD45B (Growth Arrest and DNA-Damage inducible 45). GADD45 genes have been implicated in DNA repair. GADD45G underwent a $\log_2$ expression fold change of 2.25 in S1 and 2.04 in S2, for GADD45B this was 1.08 and 2.17, respectively. Like heat shock proteins the Gadd45 family of genes have been reported as up-regulated by a number of rodent studies examining cerebral ischemia (Schmidt-Kastner et al., 2002. *Brain Res Mol Brain Res.* 108(1-2): 81-93; 7-9, 20). A previous analysis of rat brain during ischemia revealed that expression of these genes is induced by transient global ischemia (Chen et al., 1998. *J Cereb Blood Flow Metab.* 18(6):646-57). These researchers concluded that this could indicate a neuroprotective role for these genes. Our results show this increased expression during ischemia also exists in primates, further implicating its role in ischemic cellular response.

The apoptotic gene BAG3 was also significantly upregulated in ischemic brain tissue, with a $\log_2$ fold change of 1.7 in S1 and 2.97 in S2. An expression study of cerebral ischemia in rats also reported this gene as highly upregulated (Schmidt-Kastner et al., 2002. *Brain Res Mol Brain Res.* 108(1-2):81-93). The dissolution of cytoskeleton proteins is known to occur after ischemia (Lipton, 1999. *Physiol Rev.* 79(4):1431-568), and interestingly, we observed that the gene activity-regulated cytoskeleton-associated protein (ARC) is up-regulated in ischemic brain tissue ($\log_2$ fold change of 1.84 in S1 and 1.9 in S2). Up-regulation of ARC has been observed in previous studies of cerebral ischemia in rat (Buttner et al., 2009. *Brain Res.* 1252:1-14).

Another class of genes that have been implicated in cerebral ischemia is dual-specific phosphatases (Dusp) (Wang et al., 2011. *Brain Res.* 1372:13-21). Their protein products are able to inactivate MAPK proteins. Two Dusp genes were highly up-regulated in our study, DUSP1 ($\log_2$ fold change of 1.43 in S1 and 1.43 in S2) and DUSP5 ($\log_2$ fold change of 1.05 in S1 and 1.67 in S2). Interestingly, Dusp5 has been suggested to be a target of p53 (Ueda et al., 2003. *Oncogene.* 22(36):5586-91).

Gene Expression Changes in the Blood

The expression patterns observed in the blood were similar to that of the brain, however there were some limitations in this study regarding the blood transcriptomics. Due to the relatively small number of samples (1 sample per time point for each monkey), time course analysis was not feasible. In lieu of a time course analysis, samples collected before occlusion were compared to each post-occlusion sample in a pairwise manner. In order to perform gene set analysis, the differential expression results from the comparison that yielded the largest change in expression was used with GSEA. The gene sets implicated by this analysis showed a strong correlation with expression patterns in the brain.

Hierarchical clustering of blood expression levels revealed that pre- and post-occlusion samples cluster independently (data not shown). Although the separation is not as stark as it is for the brain samples, there is still a clear difference in gene expression between pre- and post-occlusion. These results suggest that further experiments could reveal a panel of blood biomarkers which may be used for the diagnosis of stroke. Due to the small number of samples and individuals in this study, it would be difficult to specify a subset of genes that may be used for diagnosis, however the distinct expression pattern suggests that with a larger sample size, this would be possible.

Our analysis of differentially expressed genes in the blood of macaques undergoing cerebral ischemia revealed that, like the brain, the majority of transcripts in the blood are up-regulated. When samples are pooled between monkeys, and all post-occlusion samples are pooled, 651 genes have a high level of differential expression (fold change more than 2), out of which 513 are up-regulated.

Notable among these differentially expressed genes are four S100 genes: S100A8, S100A12, S100P, and S100A9. S100 are calcium-binding proteins from glial cells. The most highly differentially expressed of this group is S100A8 ($\log_2$ fold change of 3.29, p=0.027; data not shown), which is strongly associated with pro-inflammatory functions (Sedaghat & Notopoulos, 2008. *Hippokratia.* 12(4):198-204).

Gene Sets Implicated in Cerebral Ischemia

Brain

Gene set enrichment analysis of brain expression data revealed several gene sets involved in DNA repair and apoptosis that are up-regulated in the ischemic brain samples. The top 5 enriched gene sets were TNFA signalling via NFKB, apoptosis, p53 pathway, hypoxia, and UV response up. Some of these pathways have been described as related to cerebral ischemia in previous studies.

The most enriched gene set in the brain is tumor necrosis factor alpha (TNFA) signalling via NF-κB. The TNFA cytokine activates NFKB, which is involved in inflammatory response. A number of previous studies have reported up-regulation of pro-inflammatory cytokines (Schmidt- Kastner et al., 2002. *Brain Res Mol Brain Res.* 108(1-2): 81-93; Lu et al., 2004. *J Neurosci Res.* 77(6):843-57; Broughton et al., 2009. *Stroke.* 40(5):e331-9).

Also, up-regulated were gene sets involved in apoptosis and the p53 pathway. These pathways are activated in the event of DNA damage or cell stress, and previous studies have noted up-regulation of various pro-apoptotic factors (Buttner et al., 2009. *Brain Res.* 1252:1-14).

Additionally, the pathways of NFKB and p53 have been shown to contribute to neuroprotection (Zhang et al., 2005. *J Cereb Blood Flow Metab.* 25(1):30-40; Chen et al., 2011. *Antioxid Redox Signal.* 14(8):1505-17).

It is interesting to note that the gene IL-6 is a highly connected member of the TNFA signalling, apoptosis, and hypoxia pathways (data not shown). This gene has a $\log_2$ fold increase in expression of 1.08 and 1.53 in S1 and S2 brain samples, respectively. The HMOX1-CDKN1A interaction is also common across several gene sets (apoptosis, p53, and hypoxia), and the up-regulation of HMOX1 is also significant.

Blood

Gene set enrichment analysis of the differential expression results from the blood revealed pathways involved in signalling, hypoxia, and inflammatory response. The top 5 gene sets enriched ischemic blood samples were TNFA signalling via NFKB, hypoxia, hedgehog signalling, inflammatory response, and angiogenesis.

Interestingly, two of the most enriched gene sets in brain are also enriched in the blood: TNFA signalling via NFKB and hypoxia response. Both of these pathways fit well into the model of ischemia response. 37 out of the 108 genes in the TNFA signalling via NFKB gene set have core enrichment in the blood (NES=1.92), and 42 out of 118 genes in the hypoxia response gene set have core enrichment (NES=1.91). The gene set TNFA signalling via NFKB appears to be the pathway most involved in ischemia, with over 50% of the set having core enrichment in brain and over 30% in the blood.

Common Expression Between Brain and Blood

In order to compare brain and blood differential expression, all genes were sorted by fold change and every possible hypergeometric overlap was tested, which revealed that there was a significant overlap of both up- and down-regulated genes in the gene lists. Our analysis of the most significant hypergeometric overlap of up- and down-regulated genes revealed that the intersections contains 493 and 2156 genes, respectively (FIG. 2).

An additional, more stringent, analysis of blood expression data was also performed where pre- and post-occlusion samples in each monkey were compared separately, and only the time point resulting in the largest fold change was kept. These results were merged with the brain expression data and genes were filtered for high differential expression in both brain (fold change ≥2) and blood (fold change ≥1.5). 9 genes were identified as highly differentially expressed in both the brain and the blood (Table 1). All 9 of these genes appear in the most significant hypergeometric overlap described above.

These top 9 genes are HSPA1B, PTGS2, BAG3, ADM, TM4SF1, DUSP1, HMOX1, LDLR-like, and G0S2. HSPA1B, BAG3, and DUSP1 have been discussed in previous sections. The majority of these genes have a sharp increase in expression, which levels off over time (FIGS. 3 and 4).

Prostaglandin-Endoperoxide Synthase 2 (PTGS2/COX2) is an enzyme that plays a role in prostaglandin biosynthesis. This gene is known to become up-regulated during inflammation, and is a target of aspirin. Aspirin suppresses the production of prostaglandins and some dosages reduce the risk of stroke (Tohgi et al., 1992. *Stroke.* 23(10):1400-3; Eikelboom et al., 2002. *Circulation.* 105(14):1650-5).

Adrenomedullin (ADM) gene expression levels in the blood have been shown to be associated with the severity of ischemic stroke (Liu et al., 2014. *Int J Neurosci.* 124(4): 271-80). Liu et al. suggests that ADM expression levels in peripheral blood leukocytes could indicate the severity of tissue damage. This hypothesis is also implicated in our results as monkey S1 has a larger infarction volume, as shown by the MRI (data not shown), and it also has a higher level of expression of ADM in the blood than S2. Although this expression pattern is inverted in the brain.

Heme oxygenase 1 (HMOX1) is a member of the heat shock family of proteins we have discussed previously. It is believed to be part of the cellular defence system for oxidative stress-mediated injury, like stroke (Chen & Maines, 2000. *Cell Mol Biol* (Noisy-le-grand). 46(3):609-17). Additionally, previous studies have found HMOX1 to be up-regulated in the brain after cerebral ischemia (Zhao et al., 2017. *J Stroke Cerebrovasc Dis.* 26(7):1622-1634).

Conclusions

Our data showed that there is a common signature between the ischemic brain and the blood, and support the development of blood transcriptomics as a tool for biopsy transcriptome expression profiling, to characterize patients with ischemic stroke and/or to develop a companion biomarker for the assessment of neuroprotection drugs in patients with ischemic stroke.

Although it is known that plasma extracellular noncoding RNAs (ex-RNAs) are a class of circulating RNA molecules that directly modulate networks of gene expression in target tissues (Mick et al., 2017. *Stroke.* 48(4):828-834), it was quite unexpected to identify common profile of RNA coding sequence in the brain and blood. This pattern of expression of ischemia-related genes being observed in the blood of patients with cerebral ischemia has been noted before in study by Moore et al. (2005. *Circulation.* 111(2):212-21). They found genes related to hypoxia in PBMC even though the PBMC itself was not hypoxic, though the brain was. Our results further Moore et al.'s conclusion that blood could be used as a diagnostic tool for confirming ischemic stroke.

Example 2: Clinical Study Protocol

We used a non-human primate model (Gauberti et al., 2012. *Cerebrovasc Dis.* 33(4):329-39), with human thrombin injection in the MCA artery. Our study revealed that ischemic and non-ischemic samples can be distinguished based on their expression profiles 6 hours after ischemia. Identified upregulated genes belong to pathways involved in cell death and DNA damage repair. Comparison of genes differentially expressed in the brain and the blood revealed a significant overlap of gene expression patterns.

Together, these results indicated the potential to identify ischemic stroke through transcriptomic profile in the brain and the blood.

Nine most significantly overlapping up-regulated genes in brain and blood were identified and are used further in a human study.

We propose to translate the data generated from monkeys to humans. Up-regulated genes identified both in ischemic brain and in peripheral blood in the primate model of ischemic stroke are studied in samples from 20 ischemic patients, 20 haemorrhagic patients and matched controls. We then look to the corresponding proteins in order to be able to potentially develop a rapid detection test as already performed in other cardiovascular diseases.

Pilot Case-Control Study

Case-control study with cases being first ever ischemic stroke paired for age, sex and cardiovascular risk measured by a score (European Heart Score) before the index stroke in patients.

Ischemic cases are recruited from the Brest stroke registry. The registry includes 900 patients per year. The control group is recruited from one centre (Brest University hospital).

Primary Objective:

To determine an RNA blood biomarker test based on genes identified whose expression is significantly increased.

Design of the Study:

Case-control study with case being first ever ischemic stroke paired for age, sex and cardiovascular risk measured by a score (European Heart Score) before the index stroke in patients.

Primary Endpoint:

Expression (measured in $\log_2$) of each of the genes identified 6 hours after ischemia onset.

Primary Statistical Analysis:

The expression of each candidate genes is compared in case and controls with a student test for paired data.

Secondary Statistical Analysis:

The expression of each gene is compared for cases between the acute phase of ischemic stroke and 3 months after.

Sample Size Estimation for the Full Study:

The difference between case and controls is set at 1.5-fold for cases compared to controls (Fold Change FC=1.5 and log 2FC=0.585), for a standard deviation of $\log_2$ expression intensity inferior to 1 (personal data).

With these hypotheses (difference=0.585 and standard deviation=1), a power of 90% and a Bonferroni correction for tests multiplicity, the estimation of the number of required subjects is 110 cases and 110 controls. This calculation does not take in account the effect of the possible increase of power provided by pairing, since the correlation level of the response is unknown.

Inclusion Criteria

For Patients:

Age >18-year-old; carotid ischemic stroke onset inferior to 6 hours; ability to have the $T_1$ blood sample before 6 hours; eligibility to thrombolysis or thrombectomy.

Initial NIHSS score >0; patients with CT or MRI imaging compatible with an ischemic stroke; patients with multimodal imaging allowing to analyse penumbra either through MRI or CT perfusion and vessels supra-aortic vessels and intra-cerebral vessels (Willis circle) imaging.

Exclusion criteria includes patients with intracerebral haemorrhage.

For Controls:

Age >18-year-old; stroke-free standardized questionnaire; high risk cardiovascular subjects without cardiovascular disease and no stroke.

Case Report Form (CRF):

For each patient and control, demographic and clinical characteristics, cardiovascular risk factors and current treatment are recorded using the standardized report form of the Brest Stroke registry.

Cerebral Imaging:

At the acute phase, perfusion MRI or CT and angio-MR or angio-scan

Clinical and Imaging Follow-Up:

For patients, rankin scores at 3 months±15 days and cerebral MRI at 3 months±15 days.

Number of Samples Per Patients:

42 mL of blood are drawn from 6 different times: <6 hours, 12 hours±2, 24 hours±4, 48 hours±4, 7 days±2 days, and at 3 months±15 days after stroke onset.

Number of Samples Per Control:

42 mL of blood are drawn once for each control.

Number of Patients and Controls:

20 patients for ischemic cases; 20 controls matched with ischemic cases for age, sex and European Heart score.

Hemorrhagic Patients

The haemorrhagic cases are recruited from the Brest stroke registry as a different group with the same number of samples per patient as in the ischemic group.

Inclusion Criteria

For Patients:

Age >18-year-old; intracerebral haemorrhage with onset inferior to 6 hours; ability to have the $T_1$ blood sample before 6 hours.

Initial NIHSS score >0; patients with $C_T$ or MRI imaging compatible with a haemorrhagic stroke.

Exclusion criteria includes patients with traumatic intracerebral haemorrhage and patients with ischemic stroke.

Number of Patients 20 patients for haemorrhagic cases.

Ethical Aspects:

The project is conducted in accordance to the Declaration of Helsinki principles and Good Clinical Practice (GCP-ICHE6). It is submitted for approval to a Human Research Ethics Committee in accordance with French regulation for clinical trial. Written informed consent is collected from each participant.

Data Management and Biobanking:

Data entry is performed by data manager into a database managed by the software Clinsight (Capture system). The biobank is stored in Brest University Hospital's centre for biological resources (CRB—Centre de Ressources Biologiques) certified NFS 96-900.

Recruitment of Patients and Controls

Recruitment Centers:

Patients and control phenotype as well as blood collection are implemented via the CHRU of Brest.

Imaging Characterization and Centralized Post-Processing of Data

The aim of the initial functional imaging (CT or MRI perfusion) is to map the core of the infarction and its penumbra, and to follow the evolution of both zones at 3 months on MRI. The initial imaging takes into account vessel patency. A software allows a standardized perfusion analysis for MRI and CT scan. Another software allows the estimation of final volume on MRI and the comparison with the penumbra evaluated on the first imaging.

Imaging Platforms:

A 64-row (or more) multi-detector CT scan or a 1.5 Tesla MRI or 3.0 Tesla MRI scanners is used with contrast media for initial imaging.

Methods of Data Acquisition:

Either of:

CT non-contrast head; CT brain perfusion; Computed Tomography Angiography (CTA) head and neck; or Brain MR including Diffusion-Weighted Imaging (DWI), FLuid Attenuated Inversion Recovery (FLAIR), and Gradient Recalled Echo (GRE), Magnetic Resonance Angiography (MRA) of the head using Time Of Flight, MR brain perfusion using Dynamic Susceptibility Contrast (DSC), Gadolinium MRA of the aortic arch and cervical arteries.

In the CT group, the ischemic core is evaluated either by relative cerebral blood flow or cerebral blood volume (CBV). In the MR group of patients, the ischemic core (tissue considered irreversibly injured) is evaluated based on an apparent diffusion coefficient (ADC) threshold.

Critically hypoperfused tissue is evaluated for MR and CT group based on time to maximum signal of a deconvolved signal intensity curve ($T_{max}$) threshold of >6 seconds. The DWI lesion volume or CT Alberta Stroke Program Early CT Score (ASPECTS) is recorded for MRI or CT, respectively. The location of the occlusion (internal carotid artery (ICA), M1, M2, basilar, or no occlusion) is recorded.

At 3 months, brain MR including DWI, 3D T2-FLAIR and 3D T1 Gradient Echo, T2(GRE), MRA of the head using TOF.

Post-Imaging Processing

Raw DICOM data of perfusion imaging (CT and MRI) are post-processed using perfusion mismatch analyser software. The final infarct volume is measured on the T2 FLAIR according to segmentation methods. Engineers from the Laboratory of Medical Information Processing (LaTIM—INSERM UMR 1101 Brest) participate to the study.

---

The invention claimed is:

1. A method for eliminating or reducing the symptoms of a stroke, for slowing or eliminating the progression of a stroke, and/or for delaying the initial occurrence or the reoccurrence of a stroke, in a human or a non-human primate subject identified as being affected by stroke or as being at risk of having a stroke, comprising:
   a. identifying the subject as being affected with a stroke or as being at risk of having a stroke by:
   i) determining a signature in a sample obtained from the subject by measuring the expression levels of at least three biomarkers selected from the group consisting of PTGS2, HMOX1, LDLR, HSPA1B, G0S2, BAG3, TM4SF1, DUSP1 and ADM wherein the sample is a blood sample, a plasma sample, a serum sample, or a saliva sample;
   ii) comparing the signature determined in step i) with a reference signature;
   iii) identifying the subject with the expression levels of the at least three biomarkers in the signature are higher than the expression levels of the same at least three biomarkers in the reference signature as being affected with a stroke or as being at risk of having a stroke; and
   b. administering thrombectomy, antithrombotic agents, anticoagulants, antiplatelet drugs, thrombolytic drugs, a neuroprotective agent, hypothermia, or a combination thereof, to treating or preventing the stroke in the subject identified as being affected with a stroke or as being at risk of having a stroke.

2. The method according to claim 1, wherein step i) comprises measuring the expression levels of PTGS2, HMOX1, LDLR, HSPA1B, G0S2, BAG3, TM4SF1, DUSP1 and ADM.

3. The method according to claim 1, wherein the reference signature is obtained by measuring the expression levels of the biomarkers in a reference population of substantially healthy subjects.

4. The method according to claim 1, wherein stroke is ischemic stroke, transient ischemic attack or a hemorrhagic stroke.

5. The method according to claim 1, wherein the subject has experienced a stroke and is at risk of having a recurrent stroke.

6. The method according to claim 1, wherein the signature enables for distinguishing a stroke from a stroke mimic.

* * * * *